(12) United States Patent
Jeong

(10) Patent No.: US 10,961,258 B2
(45) Date of Patent: Mar. 30, 2021

(54) HETEROCYCLIC AMIDES AS KINASE INHIBITORS

(71) Applicant: GLAXOSMITHKLINE INTELLECTUAL PROPERTY DEVELOPMENT LIMITED, Middlesex (GB)

(72) Inventor: Jae U. Jeong, Collegeville, PA (US)

(73) Assignee: GLAXOSMITHKLINE INTELLECTUAL PROPERTY DEVELOPMENT LIMITED, Brentford (GB)

(*) Notice: Subject to any disclaimer, the term of this patent is extended or adjusted under 35 U.S.C. 154(b) by 302 days.

(21) Appl. No.: 16/061,497

(22) PCT Filed: Dec. 21, 2016

(86) PCT No.: PCT/IB2016/057884
§ 371 (c)(1),
(2) Date: Jun. 12, 2018

(87) PCT Pub. No.: WO2017/109724
PCT Pub. Date: Jun. 29, 2017

(65) Prior Publication Data
US 2020/0270273 A1    Aug. 27, 2020

Related U.S. Application Data

(60) Provisional application No. 62/270,075, filed on Dec. 21, 2015.

(51) Int. Cl.

| | | |
|---|---|---|
| *C07D 471/04* | (2006.01) | |
| *C07D 491/048* | (2006.01) | |
| *C07D 495/04* | (2006.01) | |
| *C07D 513/04* | (2006.01) | |
| *A61K 9/06* | (2006.01) | |
| *A61K 9/08* | (2006.01) | |
| *A61K 9/20* | (2006.01) | |
| *A61K 9/48* | (2006.01) | |
| *A61K 47/06* | (2006.01) | |
| *C07D 487/04* | (2006.01) | |

(52) U.S. Cl.
CPC .............. *C07D 513/04* (2013.01); *A61K 9/06* (2013.01); *A61K 9/08* (2013.01); *A61K 9/2013* (2013.01); *A61K 9/2018* (2013.01); *A61K 9/2054* (2013.01); *A61K 9/2059* (2013.01); *A61K 9/4858* (2013.01); *A61K 9/4866* (2013.01); *A61K 47/06* (2013.01); *C07D 487/04* (2013.01); *C07D 491/048* (2013.01); *C07D 495/04* (2013.01)

(58) Field of Classification Search
CPC .......................... C07D 471/04; C07D 491/048; C07D 495/04; C07D 513/04
See application file for complete search history.

(56) References Cited

U.S. PATENT DOCUMENTS

2017/0226127 A1    8/2017    Estrada et al.

FOREIGN PATENT DOCUMENTS

| CA | 3002543 | 4/2017 |
|---|---|---|
| WO | WO 2014/125444 A1 | 8/2014 |
| WO | WO 2017/004500 A1 | 1/2017 |
| WO | WO 2018/073193 | 4/2018 |

*Primary Examiner* — Bruck Kifle
(74) *Attorney, Agent, or Firm* — Nora L. Stein; Fang Qian; Kathryn Lutomski

(57) ABSTRACT

Disclosed are compounds having Formula (I):

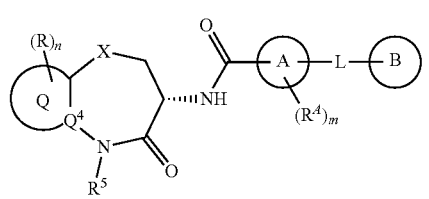

wherein Q, X, A, L, B, $Q^4$, R, $R^4$, $R^5$, n and m are as defined herein, and methods of making and using the same.

3 Claims, No Drawings

HETEROCYCLIC AMIDES AS KINASE INHIBITORS

This application is a § 371 of International Application No. PCT/IB2016/057884, filed 21 Dec. 2016, which claims the benefit of U.S. Provisional Application No. 62/270,075, filed 21 Dec. 2015.

FIELD OF THE INVENTION

The present invention relates to heterocyclic amides that inhibit RIP1 kinase and methods of making and using the same.

BACKGROUND OF THE INVENTION

Receptor-interacting protein-1 (RIP1) kinase, originally referred to as RIP, is a TKL family serine/threonine protein kinase involved in innate immune signaling. RIP1 kinase is a RHIM domain containing protein, with an N-terminal kinase domain and a C-terminal death domain ((2005) Trends Biochem. Sci. 30, 151-159). The death domain of RIP1 mediates interaction with other death domain containing proteins including Fas and TNFR-1 ((1995) Cell 81 513-523), TRAIL-R1 and TRAIL-R2 ((1997) Immunity 7, 821-830) and TRADD ((1996) Immunity 4, 387-396), while the RHIM domain is crucial for binding other RHIM domain containing proteins such as TRIF ((2004) Nat Immunol. 5, 503-507), DAI ((2009) EMBO Rep. 10, 916-922) and RIP3 ((1999) J. Biol. Chem. 274, 16871-16875); (1999) Curr. Biol. 9, 539-542) and exerts many of its effects through these interactions. RIP1 is a central regulator of cell signaling, and is involved in mediating both pro-survival and programmed cell death pathways which will be discussed below.

The role for RIP1 in cell signaling has been assessed under various conditions [including TLR3 ((2004) Nat Immunol. 5, 503-507), TLR4 ((2005) J. Biol. Chem. 280, 36560-36566), TRAIL (Cell Signal. 2015 February; 27(2): 306-14), FAS ((2004) J. Biol. Chem. 279, 7925-7933)], but is best understood in the context of mediating signals downstream of the death receptor TNFR1 ((2003) Cell 114, 181-190). Engagement of the TNFR by TNF leads to its oligomerization, and the recruitment of multiple proteins, including linear K63-linked polyubiquitinated RIP1 ((2006) Mol. Cell 22, 245-257), TRAF2/5 ((2010) J. Mol. Biol. 396, 528-539), TRADD ((2008) Nat. Immunol. 9, 1037-1046) and cIAPs ((2008) Proc. Natl. Acad. Sci. USA. 105, 11778-11783), to the cytoplasmic tail of the receptor. This complex which is dependent on RIP1 as a scaffolding protein (i.e. kinase independent), termed complex I, provides a platform for pro-survival signaling through the activation of the NFκB and MAP kinases pathways ((2010) Sci. Signal. 115, re4). Alternatively, binding of TNF to its receptor under conditions promoting the deubiquitination of RIP1 (by proteins such as A20 and CYLD or inhibition of the cIAPs) results in receptor internalization and the formation of complex II or DISC (death-inducing signaling complex) ((2011) Cell Death Dis. 2, e230). Formation of the DISC, which contains RIP1, TRADD, FADD and caspase 8, results in the activation of caspase 8 and the onset of programmed apoptotic cell death also in a RIP1 kinase independent fashion ((2012) FEBS J 278, 877-887). Apoptosis is largely a quiescent form of cell death, and is involved in routine processes such as development and cellular homeostasis.

Under conditions where the DISC forms and RIP3 is expressed, but apoptosis is inhibited (such as FADD/caspase 8 deletion, caspase inhibition or viral infection), a third RIP1 kinase-dependent possibility exists. RIP3 can now enter this complex, become phosphorylated by RIP1 and initiate a caspase-independent programmed necrotic cell death through the activation of MLKL and PGAM5 ((2012) Cell 148, 213-227); ((2012) Cell 148, 228-243); ((2012) Proc. Natl. Acad. Sci. USA. 109, 5322-5327). As opposed to apoptosis, programmed necrosis (not to be confused with passive necrosis which is not programmed) results in the release of danger associated molecular patterns (DAMPs) from the cell. These DAMPs are capable of providing a "danger signal" to surrounding cells and tissues, eliciting proinflammatory responses including inflammasome activation, cytokine production and cellular recruitment ((2008) Nat. Rev. Immunol 8, 279-289).

Dysregulation of RIP1 kinase-mediated programmed cell death has been linked to various inflammatory diseases, as demonstrated by use of the RIP3 knockout mouse (where RIP1-mediated programmed necrosis is completely blocked) and by Necrostatin-1 (a tool inhibitor of RIP1 kinase activity with poor oral bioavailability). The RIP3 knockout mouse has been shown to be protective in inflammatory bowel disease (including Ulcerative colitis and Crohn's disease) ((2011) Nature 477, 330-334), Psoriasis ((2011) Immunity 35, 572-582), retinal-detachment-induced photoreceptor necrosis ((2010) PNAS 107, 21695-21700), retinitis pigmentosa ((2012) Proc. Natl. Acad. Sci., 109:36, 14598-14603), cerulein-induced acute pancreatitis ((2009) Cell 137, 1100-1111) and Sepsis/systemic inflammatory response syndrome (SIRS) ((2011) Immunity 35, 908-918). Necrostatin-1 has been shown to be effective in alleviating ischemic brain injury ((2005) Nat. Chem. Biol. 1, 112-119), retinal ischemia/reperfusion injury ((2010) J. Neurosci. Res. 88, 1569-1576), Huntington's disease ((2011) Cell Death Dis. 2 e115), renal ischemia reperfusion injury ((2012) Kidney Int. 81, 751-761), cisplatin induced kidney injury ((2012) Ren. Fail. 34, 373-377) and traumatic brain injury ((2012) Neurochem. Res. 37, 1849-1858). Other diseases or disorders regulated at least in part by RIP1-dependent apoptosis, necrosis or cytokine production include hematological and solid organ malignancies ((2013) Genes Dev. 27: 1640-1649), bacterial infections and viral infections ((2014) Cell Host & Microbe 15, 23-35) (including, but not limited to, tuberculosis and influenza ((2013) Cell 153, 1-14)) and Lysosomal storage diseases (particularly, Gaucher Disease, Nature Medicine Advance Online Publication, 19 Jan. 2014, doi:10.1038/nm.3449).

A potent, selective, small molecule inhibitor of RIP1 kinase activity would block RIP1-dependent cellular necrosis and thereby provide a therapeutic benefit in diseases or events associated with DAMPs, cell death, and/or inflammation.

SUMMARY OF THE INVENTION

The invention is directed to compounds according to Formula (I):

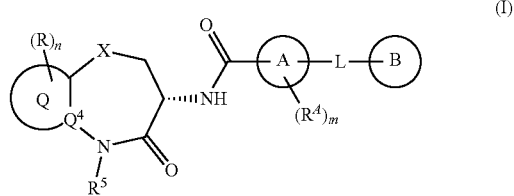

wherein:

X is O, S, SO, $SO_2$, NH, CO, $CH_2$, $CF_2$, $CH(CH_3)$, CH(OH), or $N(CH_3)$;

Q is a 5-membered heteroaryl ring moiety, wherein the heteroaryl ring moiety contains one nitrogen, oxygen, or sulfur ring heteroatom, and optionally contains 1, 2, or 3 additional nitrogen ring atoms;

$Q^4$ is N or C;

n is 0-3;

each R is independently selected from halogen, cyano, $(C_1-C_6)$alkyl, halo$(C_1-C_4)$alkyl, $(C_1-C_6)$alkoxy, halo$(C_1-C_4)$alkoxy, hydroxyl, —COOH, $(C_1-C_4)$alkoxy$(C_1-C_4)$alkoxy-, $(C_1-C_4)$alkylSO$_2$-, $(C_1-C_4)$alkylSO$_2$NHC(O)—, $(C_1-C_4)$alkylC(O)NH—, $((C_1-C_4)$alkyl$)((C_1-C_4)$alkyl)NC(O)—, $(C_1-C_4)$alkylC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkylSO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, and an optionally substituted 3-6 membered cycloalkyl, $(C_3-C_6)$cycloalkyl-C(O)—, phenyl, phenyl-C(O)—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, 5-6 membered heteroaryl-C(O)—, or 5-6 membered heteroaryl-C(O)NH— group, wherein any of said optionally substituted 3-6 membered cycloalkyl, phenyl, 5-6 membered heterocycloalkyl and 5-6 membered heteroaryl (including the optionally substituted cycloalkyl, phenyl, 5-6 membered heterocycloalkyl and 5-6 membered heteroaryl moieties of the $(C_3-C_6)$cycloalkyl-C(O)—, phenyl-C(O)—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl-C(O)—, or 5-6 membered heteroaryl-C(O)NH— groups) are optionally substituted by 1-3 substituents each independently selected from the group consisting of halogen, cyano, $(C_1-C_6)$alkyl, halo$(C_1-C_4)$alkyl, $(C_1-C_6)$alkoxy, halo$(C_1-C_4)$alkoxy, hydroxyl, —COOH, $(C_1-C_4)$alkoxy$(C_1-C_4)$alkoxy-, $(C_1-C_4)$alkylSO$_2$-, $(C_1-C_4)$alkylSO$_2$NHC(O)—, $(C_1-C_4)$alkylC(O)NH—, $((C_1-C_4)$alkyl$)((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkylSO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, —NH$_2$, —NH$((C_1-C_4)$alkyl), and —N$((C_1-C_4)$alkyl$)((C_1-C_4)$alkyl);

or two R groups, taken together with the atoms through which they are connected form an optionally substituted 5-7 membered carbocyclic or heterocyclic ring, wherein the optionally substituted 5-7 membered carbocyclic or heterocyclic ring is optionally substituted by 1-3 substituents each independently selected from the group consisting of halogen, cyano, $(C_1-C_6)$alkyl, halo$(C_1-C_4)$alkyl, $(C_1-C_6)$alkoxy, halo$(C_1-C_4)$alkoxy, hydroxyl, —COOH, $(C_1-C_4)$alkoxy$(C_1-C_4)$alkoxy-, $(C_1-C_4)$alkylSO$_2$-, $(C_1-C_4)$alkylSO$_2$NHC(O)—, $(C_1-C_4)$alkylC(O)NH—, $((C_1-C_4)$alkyl$)((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkylSO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, —NH$_2$, —NH$((C_1-C_4)$alkyl), and —N$((C_1-C_4)$alkyl$)((C_1-C_4)$alkyl), and the 5-6 heterocyclic ring contains one N or O atom;

$R^5$ is H or methyl;

A is phenyl, 5-6 membered heteroaryl, or 5-6 membered heterocycloalkyl, wherein the carbonyl moiety and L are substituted 1,3 on ring A;

m is 0 or m is 1 and $R^4$ is $(C_1-C_4)$alkyl; and

L is O, S, NH, $N(CH_3)$, $CH_2$, $CH_2CH_2$, $CH(CH_3)$, CHF, $CF_2$, $CH_2O$, $CH_2N(CH_3)$, $CH_2NH$, or CH(OH);

B is an optionally substituted $(C_3-C_6)$cycloalkyl, phenyl, 5-6 membered heteroaryl, or 5-6 membered heterocycloalkyl;

wherein said $(C_3-C_6)$cycloalkyl, phenyl, 5-6 membered heteroaryl, or 5-6 membered heterocycloalkyl is unsubstituted or is substituted by one or two substituents each independently selected from halogen, $(C_1-C_4)$alkyl, halo$(C_1-C_4)$alkyl, $(C_1-C_4)$alkoxy, halo$(C_1-C_4)$alkoxy, nitro, and $(C_1-C_4)$alkylC(O)—;

or the moiety-L-B is $(C_3-C_6)$alkyl, $(C_3-C_6)$alkoxy, halo$(C_3-C_6)$alkoxy, $(C_3-C_6)$alkenyl, or $(C_3-C_6)$alkenyloxy;

or a salt, particularly a pharmaceutically acceptable salt, thereof.

Accordingly, the present invention is also directed to a method of inhibiting RIP1 kinase which method comprises contacting a cell with a compound according to Formula (I), or a salt, particularly a pharmaceutically acceptable salt, thereof.

The invention is further directed to a method of treating a RIP1 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Such RIP1 kinase-mediated diseases or disorders include inflammatory bowel disease (including Crohn's disease and ulcerative colitis), psoriasis, retinal detachment, retinitis pigmentosa, arthritis (including rheumatoid arthritis, spondyloarthritis, gout, and systemic onset juvenile idiopathic arthritis (SoJIA)), transplant rejection, ischemia reperfusion injury of solid organs, multiple sclerosis, and tumor necrosis factor receptor associated periodic syndrome.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP1 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

As used herein, the term "alkyl" represents a saturated, straight or branched hydrocarbon group having the specified number of carbon atoms. The term "$(C_1-C_4)$alkyl" refers to an alkyl moiety containing from 1 to 4 carbon atoms. Exemplary alkyls include, but are not limited to, methyl, ethyl, n-propyl, isopropyl, n-butyl, isobutyl, s-butyl, and t-butyl.

When a substituent term such as "alkyl" is used in combination with another substituent term, for example as in "hydroxy$(C_1-C_4)$alkyl", the linking substituent term (e.g., alkyl) is intended to encompass a divalent moiety, wherein the point of attachment is through that linking substituent. Examples of "hydroxy$(C_1-C_4)$alkyl" groups include, but are not limited to, hydroxymethyl, hydroxyethyl, and hydroxyisopropyl.

The term "halo$(C_1-C_4)$alkyl" represents a group having one or more halogen atoms, which may be the same or different, at one or more carbon atoms of an alkyl moiety containing from 1 to 4 carbon atoms. Examples of "halo$(C_1-C_4)$alkyl" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkoxy" refers to an "alkyl-oxy-" group, containing an alkyl moiety attached through an oxygen linking atom. For example, the term "$(C_1-C_4)$alkoxy" represents a saturated, straight or branched hydrocarbon moiety having at least 1 and up to 4 carbon atoms attached through an oxygen linking atom. Exemplary "$(C_1-C_4)$alkoxy" groups include, but are not limited to, methoxy, ethoxy, n-propoxy, isopropoxy, n-butoxy, s-butoxy, and t-butoxy.

The term "halo$(C_1-C_4)$alkoxy" refers to a "haloalkyl-oxy-" group, containing a "halo$(C_1-C_4)$alkyl" moiety attached through an oxygen linking atom, which halo$(C_1-C_4)$alkyl" refers to a moiety having one or more halogen atoms, which may be the same or different, at one or more carbon atoms of an alkyl moiety containing from 1 to 4 carbon atoms. Exemplary "halo$(C_1-C_4)$alkoxy" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

A carbocyclic group is a cyclic group in which all of the ring members are carbon atoms, which may be saturated, partially unsaturated (non-aromatic) or fully unsaturated (aromatic).

"Cycloalkyl" refers to a non-aromatic, saturated, cyclic hydrocarbon group containing the specified number of carbon atoms. For example, the term "$(C_3-C_6)$cycloalkyl" refers to a non-aromatic cyclic hydrocarbon ring having from three to six ring carbon atoms. Exemplary "$(C_3-C_6)$cycloalkyl" groups include cyclopropyl, cyclobutyl, cyclopentyl, and cyclohexyl.

A heterocyclic group is a cyclic group having, as ring members, atoms of at least two different elements, which cyclic group may be saturated, partially unsaturated (non-aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N-oxide, such as oxo-pyridyl (pyridyl-N-oxide).

"Heterocycloalkyl" refers to a non-aromatic, monocyclic or bicyclic group containing 3-10 ring atoms, being saturated or having one or more degrees of unsaturation and containing one or two heteroatom substitutions independently selected from oxygen, sulfur, and nitrogen. Examples of "heterocycloalkyl" groups include, but are not limited to, (3-membered) aziridinyl, thiiranyl, oxiranyl, (4-membered) azetidinyl, oxetanyl, thietanyl, (5-membered) pyrrolidinyl, tetrahydrofuranyl, tetrahydrothienyl, (6-membered), piperidinyl (piperidyl), piperazinyl, tetrahydropyranyl, tetrahydrothiopyranyl, 1,4-dioxanyl, 1,4-oxathianyl, 1,4-dithianyl, morpholinyl, thiomorpholinyl, (7-membered and larger) hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl, and 1,5,9-triazacyclododecyl.

A 5-membered heterocycloalkyl group is a non-aromatic, monocyclic group, containing 5 ring atoms, which includes one heteroatom selected independently from oxygen, sulfur, and nitrogen. A 6-membered heterocycloalkyl group is a non aromatic, monocyclic group, containing 6 ring atoms, which includes one or two heteroatoms selected independently from oxygen, sulfur, and nitrogen.

"Alkoxy" refers to an "alkyl-oxy-" group, containing an alkyl moiety attached through an oxygen linking atom. For example, the term "$(C_1-C_4)$alkoxy" represents a saturated, straight or branched hydrocarbon moiety having at least 1 and up to 4 carbon atoms attached through an oxygen linking atom. Exemplary "$(C_1-C_4)$alkoxy" groups include, but are not limited to, methoxy, ethoxy, n-propoxy, isopropoxy, n-butoxy, s-butoxy, and t-butoxy.

"Heteroaryl" represents a group or moiety comprising an aromatic monocyclic or bicyclic radical, containing 5 to 10 ring atoms, including 1 to 4 heteroatoms independently selected from nitrogen, oxygen and sulfur. This term also encompasses bicyclic groups containing either a phenyl ring moiety fused to a heterocycloalkyl ring moiety or a heteroaryl ring moiety fused to a cycloalkyl ring moiety.

Illustrative examples of heteroaryls include, but are not limited to, (5-membered) furyl (furanyl), thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, (6-membered) pyridinyl (pyridyl), oxo-pyridyl (pyridyl-N-oxide), pyridazinyl, pyrazinyl, pyrimidinyl, triazinyl, (9-membered) benzofuranyl, isobenzofuryl, 2,3-dihydrobenzofuryl, 1,3-benzodioxolyl, benzothienyl, indolizinyl, indolyl, isoindolyl, dihydroindolyl (indolinyl), isoindolinyl, benzimidazolyl, benzoxazolyl, benzothiazolyl, benzoisothiazolyl, benzoxadiazolyl, benzothiadiazolyl, indazolyl, imidazopyridinyl, pyrazolopyridinyl, benzotriazolyl, triazolopyridinyl, purinyl, (10-membered heteroaryl) quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, "5-6-membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms.

Bicyclic heteroaryl groups include 6,5-fused heteroaryl (9-membered heteroaryl) and 6,6-fused heteroaryl (10-membered heteroaryl) groups. This term encompasses bicyclic groups containing either a phenyl ring moiety fused to a 5-6 membered heterocycloalkyl ring moiety or a 5-6 membered heteroaryl ring moiety fused to a 5-6 membered cycloalkyl ring moiety.

Unless otherwise specified, all bicyclic ring systems may be attached at any suitable position on either ring.

The terms "halogen" and "halo" represent chloro, fluoro, bromo, or iodo substituents.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of this invention contain one or more asymmetric centers (also referred to as a chiral center), such as a chiral carbon. The stereochemistry of the chiral carbon center present in compounds of this invention is generally represented in the compound names and/or in the chemical structures illustrated herein. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

Individual stereoisomers of a compound described herein may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

In one embodiment of the compounds of this invention, X is O, S, SO, $SO_2$, NH, CO, $CH_2$, $CF_2$, $CH(CH_3)$, $N(CH_3)$, or CH(OH). In a specific embodiment, X is O, S, SO, $SO_2$, NH, CO, $CH_2$, or $N(CH_3)$. In another embodiment, X is S, SO, $SO_2$, or CO. In yet another embodiment, X is $CF_2$, $CH(CH_3)$, or CH(OH). In selected embodiments, X is NH or $N(CH_3)$. In selected embodiments, X is NH. In other selected embodiments, X is O or $CH_2$. In selected embodiments, X is S or $CH_2$. In other selected embodiments, X is S. In still other selected embodiments, X is $CH_2$.

In one embodiment of the compounds of this invention, n is 0 (and ring Q is unsubstituted). In another embodiment, n is 1 (and ring Q contains 1 R substituent). In another embodiment, n is 2 (and ring Q contains 2 independently selected R substituents).

In the compounds of Formula (I), n is 1 or 2 and each R independently selected from halogen, cyano, $(C_1-C_6)$alkyl, halo$(C_1-C_4)$alkyl, $(C_1-C_6)$alkoxy, halo$(C_1-C_4)$alkoxy, hydroxyl, —COOH, $(C_1-C_4)$alkoxy$(C_1-C_4)$alkoxy, $(C_1-C_4)$alkyl$SO_2$-, $(C_1-C_4)$alkyl$SO_2$NHC(O)—, $(C_1-C_4)$alkylC(O)NH—, $((C_1-C_4)$alkyl$)((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkyl$SO_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 3-6 membered cycloalkyl, 5-6 membered heteroaryl, and 5-6 membered heteroaryl-C(O)NH, wherein said 3-6 membered cycloalkyl, 5-6 membered heterocycloalkyl and 5-6 membered heteroaryl are optionally substituted by 1 or 2 substituents each independently selected from the group consisting of $(C_1-C_4)$alkyl and —$(C_1-C_4)$alkyl-CN.

In the compounds of Formula (I), n is 1 or 2 and each R independently selected from halogen, cyano, $(C_1-C_6)$alkyl, $(C_1-C_6)$alkoxy, halo$(C_1-C_4)$alkoxy, hydroxyl, —COOH, $(C_1-C_4)$alkoxy$(C_1-C_4)$alkoxy, 3-5 membered cycloalkyl, and 5-6 membered heteroaryl, wherein said 3-5 membered cycloalkyl or 5-6 membered heteroaryl is optionally substituted by a $(C_1-C_3)$alkyl substituent.

In the compounds of Formula (I), n is 1 or 2 and each R independently selected from halogen, cyano, $(C_1-C_6)$alkyl, hydroxyl, —COOH, $(C_1-C_4)$alkoxy$(C_1-C_4)$alkoxy, and 5-6 membered heteroaryl, wherein said 5-6 membered heteroaryl is optionally substituted by a $(C_1-C_3)$alkyl substituent.

In the compounds of Formula (I), n is 1 or 2 and each R independently selected from halogen, $(C_1-C_6)$alkyl, halo$(C_1-C_4)$alkyl, $(C_1-C_6)$alkoxy, halo$(C_1-C_6)$alkoxy, —COOH, $(C_1-C_4)$alkyl$SO_2$-, $(C_1-C_4)$alkyl$SO_2$NHC(O)—, $(C_1-C_4)$alkylC(O)NH—, $((C_1-C_4)$alkyl$)((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkoxy$(C_2-C_4)$alkylNHC(O)NH—, $(C_1-C_4)$alkyl$SO_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, and 5-6 membered heteroaryl-C(O)NH, herein said 5-6 membered heterocycloalkyl and 5-6 membered heteroaryl are optionally substituted by $(C_1-C_3)$alkyl or —$(C_1-C_3)$alkyl-CN.

In the compounds of Formula (I), n is 1 or 2 and each R independently selected from cyano, $(C_1-C_6)$alkyl, and a 5-6 membered heteroaryl, optionally substituted by a $(C_1-C_3)$ alkyl substituent.

In another embodiment, n is 1 or 2 and each R independently $(C_1-C_6)$alkyl. In another embodiment, n is 1 or 2 and each R is methyl. In another embodiment, n is 0.

In another embodiment, two R groups, taken together with the atoms through which they are connected, form an optionally substituted 5-7 membered carbocyclic or heterocyclic ring, wherein the optionally substituted 5-7 membered carbocyclic or heterocyclic ring is optionally substituted by $(C_1-C_6)$alkyl or halo$(C_1-C_4)$alkyl, and the 5-7 heterocyclic ring contains one N or O atom. In another embodiment, two R groups, taken together with the atoms through which they are connected form an optionally substituted 5-7 membered carbocyclic ring. In another embodiment, two R groups, taken together with the atoms through which they are connected form an unsubstituted 5-7 membered carbocyclic ring. In another embodiment, two R groups, taken together with the atoms through which they are connected form an unsubstituted 5-6 membered carbocyclic ring.

In specific embodiments, two R groups, taken together with the atoms through which they are connected form an unsubstituted 6 membered carbocyclic ring. In specific embodiments, two R groups, taken together with the atoms through which they are connected form an unsubstituted 6 membered aromatic (benzo) ring or an unsubstituted non-aromatic (cyclohexylenyl) ring.

In one embodiment, the invention is directed to compounds according to Formula (II):

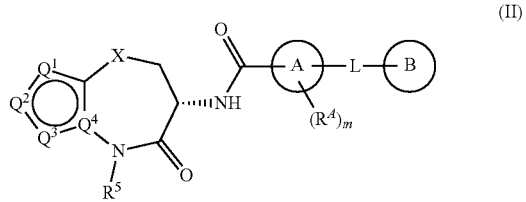

(II)

wherein:
X, $R^5$, $R^A$, m, A, L, and B are as defined herein,
$Q^1$ is N, $NR^z$, O, S, or $CR^1$;
$Q^2$ is N, $NR^z$, O, S, or $CR^2$;
$Q^3$ is N, $NR^z$, O, S, or $CR^3$;
$Q^4$ is N or C;
wherein at least one of $Q^1$, $Q^2$, $Q^3$, and $Q^4$ is N, $NR^z$, O, or S;

each $R^z$ is independently selected from H, $(C_1$-$C_4)$alkyl, —$CO(C_1$-$C_6)$alkyl, —CO—$(C_3$-$C_6)$cycloalkyl, optionally substituted phenyl, optionally substituted 5-6 membered heteroaryl, optionally substituted —CO-5-6 membered heterocycloalkyl, and optionally substituted —CO-5-6 membered heteroaryl, wherein said optionally substituted phenyl and optionally substituted 5-6 membered heteroaryl (including the optionally substituted 5-6 membered heteroaryl moiety of —CO-5-6 membered heteroaryl) is optionally substituted by 1-3 substituents each independently selected from halogen, cyano, $(C_1$-$C_6)$alkyl, halo$(C_1$-$C_4)$alkyl, $(C_1$-$C_6)$alkoxy, halo$(C_1$-$C_4)$alkoxy, hydroxyl, —COOH, $(C_1$-$C_4)$alkoxy$(C_1$-$C_4)$alkoxy, $(C_1$-$C_4)$alkylSO$_2$-, $(C_1$-$C_4)$alkylSO$_2$NHC(O)—, $(C_1$-$C_4)$alkylC(O)NH—, $((C_1$-$C_4)$alkyl)$((C_1$-$C_4)$alkyl)NC(O)—, $(C_1$-$C_4)$alkylOC(O)—, $(C_1$-$C_4)$alkylC(O)N$(C_1$-$C_4)$alkyl)-, $(C_1$-$C_4)$alkylNHC(O)—, $(C_1$-$C_4)$alkoxy$(C_2$-$C_4)$alkylNHC(O)—, $(C_1$-$C_4)$alkoxy$(C_2$-$C_4)$alkylC(O)NH—, $(C_1$-$C_4)$alkoxy$(C_2$-$C_4)$alkylNHC(O)NH—, $(C_1$-$C_4)$alkylSO$_2$$(C_2$-$C_4)$alkylNHC(O)—, $(C_1$-$C_4)$alkylNHC(O)NH—, $(C_1$-$C_4)$alkylOC(O)NH—, hydroxy$(C_1$-$C_4)$alkylOC(O)NH—, —NH$_2$, —NH$((C_1$-$C_4)$alkyl), and —N$((C_1$-$C_4)$alkyl)$((C_1$-$C_4)$alkyl);

$R^1$, $R^2$ and $R^3$ is independently selected from H, halogen, cyano, $(C_1$-$C_6)$alkyl, halo$(C_1$-$C_4)$alkyl, $(C_1$-$C_6)$alkoxy, halo$(C_1$-$C_4)$alkoxy, hydroxyl, —COOH, $(C_1$-$C_4)$alkoxy$(C_1$-$C_4)$alkoxy, $(C_1$-$C_4)$alkylSO$_2$-, $(C_1$-$C_4)$alkylSO$_2$NHC(O)—, $(C_1$-$C_4)$alkylC(O)NH—, $((C_1$-$C_4)$alkyl)$((C_1$-$C_4)$alkyl)NC(O)—, $(C_1$-$C_4)$alkylOC(O)—, $(C_1$-$C_4)$alkylC(O)N$(C_1$-$C_4)$alkyl)-, $(C_1$-$C_4)$alkylNHC(O)—, $(C_1$-$C_4)$alkoxy$(C_2$-$C_4)$alkylNHC(O)—, $(C_1$-$C_4)$alkoxy$(C_2$-$C_4)$alkylC(O)NH—, $(C_1$-$C_4)$alkoxy$(C_2$-$C_4)$alkylNHC(O)NH—, $(C_1$-$C_4)$alkylSO$_2$$(C_2$-$C_4)$alkylNHC(O)—, $(C_1$-$C_4)$alkylNHC(O)NH—, $(C_1$-$C_4)$alkylOC(O)NH—, hydroxy$(C_1$-$C_4)$alkylOC(O)NH—, 5-6 membered heterocycloalkyl-C(O)—, 5-6 membered heterocycloalkyl-$(C_1$-$C_4)$alkyl-NHC(O)—, 5-6 membered heterocycloalkyl-$(C_1$-$C_4)$alkoxy-, 3-6 membered cycloalkyl, 5-6 membered heteroaryl, or 5-6 membered heteroaryl-C(O)NH, wherein said 3-6 membered cycloalkyl, 5-6 membered heterocycloalkyl and 5-6 membered heteroaryl are optionally substituted by 1 or 2 substituents each independently selected from the group consisting of $(C_1$-$C_4)$alkyl and —$(C_1$-$C_4)$alkyl-CN;

or $R^2$ and $R^3$, or $R^z$ and $R^3$, or $R^z$ and $R^2$, taken together with the atoms through which they are connected form an optionally substituted 5-7 membered carbocyclic or heterocyclic ring, wherein the optionally substituted 5-7 membered carbocyclic or heterocyclic ring is optionally substituted by $(C_1$-$C_6)$alkyl or halo$(C_1$-$C_4)$alkyl, and the 5-6 heterocyclic ring contains one N or O atom;

or a salt, particularly a pharmaceutically acceptable salt, thereof.

In another embodiment, $Q^1$ is $NR^z$, and $Q^2$ is $CR^2$, $Q^3$ is $CR^3$, and $Q^4$ is C. In another embodiment, $Q^1$ is S, and $Q^2$ is $CR^2$, $Q^3$ is $CR^3$, and $Q^4$ is C. In another embodiment, $Q^1$ is O, and $Q^2$ is $CR^2$, $Q^3$ is $CR^3$, and $Q^4$ is C.

In another embodiment, $Q^1$ is N or $NR^z$, and $Q^2$ is $CR^2$, $Q^3$ is $NR^z$ or N, and $Q^4$ is C. In another embodiment, $Q^1$ is N, and $Q^2$ is $CR^2$, $Q^3$ is S, and $Q^4$ is C. In another embodiment, $Q^1$ is N, and $Q^2$ is $CR^2$, $Q^3$ is O, and $Q^4$ is C.

In another embodiment, $Q^1$ is $CR^1$, and $Q^2$ is $NR^z$, $Q^3$ is $CR^3$, and $Q^4$ is C. In another embodiment, $Q^1$ is $CR^1$, and $Q^2$ is S, $Q^3$ is $CR^3$, and $Q^4$ is C. In another embodiment, $Q^1$ is $CR^1$, and $Q^2$ is O, $Q^3$ is $CR^3$, and $Q^4$ is C.

In another embodiment, $Q^1$ is N or $NR^z$, and $Q^2$ is $NR^z$ or N, $Q^3$ is $CR^3$, and $Q^4$ is C. In another embodiment, $Q^1$ is S, and $Q^2$ is N, $Q^3$ is $CR^3$, and $Q^4$ is C. In another embodiment, $Q^1$ is O, and $Q^2$ is N, $Q^3$ is $CR^3$, and $Q^4$ is C.

In another embodiment, Q is $CR^1$, and $Q^2$ is N or $NR^z$, $Q^3$ is $NR^z$ or N, and $Q^4$ is C. In another embodiment, $Q^1$ is $CR^1$, and $Q^2$ is N, $Q^3$ is O, and $Q^4$ is C. In another embodiment, $Q^1$ is $CR^1$, and $Q^2$ is N, $Q^3$ is S, and $Q^4$ is C. In another embodiment, $Q^1$ is N, and $Q^2$ is S, $Q^3$ is N, and $Q^4$ is C. In another embodiment, $Q^1$ is N, and $Q^2$ is O, $Q^3$ is N, and $Q^4$ is C. In another embodiment, $Q^1$ is N, and $Q^2$ is $NR^z$, $Q^3$ is N, and $Q^4$ is C. In another embodiment, $Q^1$ is $NR^z$, and $Q^2$ is N, $Q^3$ is N, and $Q^4$ is C. In another embodiment, $Q^1$ is N, and $Q^2$ is N, $Q^3$ is $NR^z$, and $Q^4$ is C.

In one embodiment of the compounds this invention, $Q^1$ is $CR^1$, $Q^2$ is $CR^2$, $Q^3$ is $CR^3$, and $Q^4$ is N. In one embodiment of the compounds this invention, $Q^1$, $Q^2$, and $Q^3$ are each CH and $Q^4$ is N.

In the compounds of Formula (II), 1 or 2 of any of $R^1$, $R^2$, and $R^3$, respectively, is H, halogen, cyano, $(C_1$-$C_6)$alkyl, halo$(C_1$-$C_4)$alkyl, $(C_1$-$C_6)$alkoxy, halo$(C_1$-$C_4)$alkoxy, hydroxyl, —COOH, $(C_1$-$C_4)$alkoxy$(C_1$-$C_4)$alkoxy, $(C_1$-$C_4)$alkylSO$_2$-, $(C_1$-$C_4)$alkylSO$_2$NHC(O)—, $(C_1$-$C_4)$alkylC(O)NH—, $((C_1$-$C_4)$alkyl)$((C_1$-$C_4)$alkyl)NC(O)—, $(C_1$-$C_4)$alkylOC(O)—, $(C_1$-$C_4)$alkylC(O)N$(C_1$-$C_4)$alkyl)-, $(C_1$-$C_4)$alkylNHC(O)—, $(C_1$-$C_4)$alkoxy$(C_2$-$C_4)$alkylNHC(O)—, $(C_1$-$C_4)$alkoxy$(C_2$-$C_4)$alkylC(O)NH—, $(C_1$-$C_4)$alkoxy$(C_2$-$C_4)$alkylNHC(O)NH—, $(C_1$-$C_4)$alkylSO$_2$$(C_2$-$C_4)$alkylNHC(O)—, $(C_1$-$C_4)$alkylNHC(O)NH—, $(C_1$-$C_4)$alkylOC(O)NH—, hydroxy$(C_1$-$C_4)$alkylOC(O)NH—, 5-6 membered heterocycloalkyl-C(O)—, 5-6 membered heterocycloalkyl-$(C_1$-$C_4)$alkyl-NHC(O)—, 5-6 membered heterocycloalkyl-$(C_1$-$C_4)$alkoxy-, 3-6 membered cycloalkyl, 5-6 membered heteroaryl, or 5-6 membered heteroaryl-C(O)NH, wherein said 3-6 membered cycloalkyl, 5-6 membered heterocycloalkyl and 5-6 membered heteroaryl are optionally substituted by 1 or 2 substituents each independently selected from the group consisting of $(C_1$-$C_4)$alkyl and —$(C_1$-$C_4)$alkyl-CN.

In the compounds of Formula (II), 1 or 2 of any of $R^1$, $R^2$, and $R^3$, respectively, is H, halogen, cyano, $(C_1$-$C_6)$alkyl, $(C_1$-$C_6)$alkoxy, halo$(C_1$-$C_4)$alkoxy, hydroxyl, —COOH, $(C_1$-$C_4)$alkoxy$(C_1$-$C_4)$alkoxy, 3-5 membered cycloalkyl, or 5-6 membered heteroaryl, wherein said 3-5 membered cycloalkyl or 5-6 membered heteroaryl is optionally substituted by a $(C_1-C_3)$alkyl substituent.

In the compounds of Formula (II), 1 or 2 of any of $R^1$, $R^2$, and $R^3$, respectively, is H, halogen, cyano, $(C_1-C_6)$alkyl, hydroxyl, —COOH, $(C_1-C_4)$alkoxy$(C_1-C_4)$alkoxy, or 5-6 membered heteroaryl, wherein said 5-6 membered heteroaryl is optionally substituted by a $(C_1-C_3)$alkyl substituent.

In the compounds of Formula (II), 1 or 2 of any of $R^1$, $R^2$, and $R^3$, respectively, is H, halogen, $(C_1-C_6)$alkyl, halo$(C_1-C_4)$alkyl, $(C_1-C_6)$alkoxy, halo$(C_1-C_6)$alkoxy, —COOH, $(C_1-C_4)$alkylSO$_2$-, $(C_1-C_4)$alkylSO$_2$NHC(O)—, $(C_1-C_4)$alkylC(O)NH—, $((C_1-C_4)$alkyl$)((C_1-C_4)$alkyl$)$NC(O)—, $(C_1-C_4)$alkylOC(O)—, $(C_1-C_4)$alkylC(O)N$(C_1-C_4)$alkyl)-, $(C_1-C_4)$alkoxy$(C_2-C_4)$alkylNHC(O)NH—, $(C_1-C_4)$alkylSO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, or 5-6 membered heteroaryl-C(O)NH, herein said 5-6 membered heterocycloalkyl and 5-6 membered heteroaryl are optionally substituted by $(C_1-C_3)$alkyl or —$(C_1-C_3)$alkyl-CN.

In the compounds of Formula (II), 1 or 2 of any of $R^1$, $R^2$, and $R^3$, respectively, is H, cyano, $(C_1-C_6)$alkyl, or a 5-6 membered heteroaryl, optionally substituted by a $(C_1-C_3)$ alkyl substituent.

In another embodiment, one or two of any of $R^1$, $R^2$ and $R^3$ is $(C_1-C_6)$alkyl and the remaining $R^1$, $R^2$ and $R^3$ are H. In another embodiment, one or two of any of $R^1$, $R^2$ and $R^3$ is methyl and the remaining $R^1$, $R^2$ and $R^3$ are H. In another embodiment, each $R^1$, $R^2$ and $R^3$ is H.

In another embodiment, $R^2$ and $R^3$, or $R^z$ and $R^3$, or $R^z$ and $R^2$, taken together with the atoms through which they are connected form an optionally substituted 5-7 membered carbocyclic or heterocyclic ring, wherein the optionally substituted 5-7 membered carbocyclic or heterocyclic ring is optionally substituted by $(C_1-C_6)$alkyl or halo$(C_1-C_4)$alkyl, and the 5-7 heterocyclic ring contains one N or O atom. In another embodiment, $R^2$ and $R^3$, taken together with the atoms through which they are connected form an optionally substituted 5-7 membered carbocyclic ring. In another embodiment, $R^2$ and $R^3$, taken together with the atoms through which they are connected form an unsubstituted 5-7 membered carbocyclic ring. In another embodiment, $R^2$ and $R^3$, taken together with the atoms through which they are connected form an unsubstituted 5-6 membered carbocyclic ring.

In specific embodiments, $R^2$ and $R^3$, taken together with the atoms through which they are connected form an unsubstituted 6 membered carbocyclic ring. In specific embodiments, $R^2$ and $R^3$, taken together with the atoms through which they are connected form an unsubstituted 6 membered aromatic (benzo) ring or an unsubstituted non-aromatic (cyclohexylenyl) ring.

In one embodiment of the compounds of this invention, $R^5$ is H. In another embodiment, $R^5$ is methyl.

In one embodiment of the compounds of this invention, A is phenyl, 5-6 membered heteroaryl, or 5-6 membered heterocycloalkyl, wherein the carbonyl moiety and L are substituted 1,3 on ring A.

In another embodiment, A is a 5 membered heteroaryl containing one oxygen or sulfur atom and optionally containing one or two nitrogen atoms; specifically A is furyl, thienyl, oxazolyl, isoxazolyl, thiazolyl, or oxadiazolyl (more specifically, 1, 2, 4-oxadiazolyl or 1, 3, 4-oxadiazolyl). In another embodiment, A is a 5 membered heteroaryl containing one nitrogen atom and optionally containing one, two or three additional nitrogen atoms, specifically; A is pyrrolyl, pyrazolyl, imidazolyl, triazolyl (more specifically, 1, 2, 3-triazolyl or 1, 2, 4-triazolyl) or tetrazolyl. In selected embodiments, A is triazolyl. In yet embodiment of this invention, A is a 5 or 6 membered heterocycloalkyl specifically, A is piperidinyl or pyrrolidinyl. In a further embodiment of this invention, A is a 6 membered aromatic group selected from phenyl and pyridyl.

In selected embodiments of the compounds of this invention:

X is NH, S, or CH$_2$;

Q is N or NR$^z$, and Q$^2$ is CR$^2$, Q$^3$ is NR$^z$ or N, and Q$^4$ is C; or

Q is N, and Q$^2$ is CR$^2$, Q$^3$ is S, and Q$^4$ is C; or

Q$^1$ is N, and Q$^2$ is CR$^2$, Q$^3$ is O, and Q$^4$ is C; or

Q is S, and Q$^2$ is N, Q$^3$ is CR$^3$, and Q$^4$ is C; or

Q is CR$^1$, and Q$^2$ is N, Q$^3$ is O, and Q$^4$ is C; or

Q is CR$^1$, Q$^2$ is CR$^2$, Q$^3$ is CR$^3$, and Q$^4$ is N;

each $R^1$, $R^2$ and $R^3$ is H; or one or two of any of $R^1$, $R^2$ and $R^3$ is methyl and the remaining $R^1$, $R^2$ and $R^3$ are H; or $R^2$ and $R^3$, taken together with the atoms through which they are connected form an unsubstituted 6 membered aromatic ring or an unsubstituted non-aromatic ring; A is triazolyl; and m is 0.

Another embodiment of this invention is directed to a compound according to Formula (III):

(III)

wherein:

$A^1$ is C, $A^4$ is C or N, and $A^2$, $A^3$, and $A^5$ are each independently selected from CH, CR$^A$, O, S, N, NH and NR$^A$ to form a furyl, thienyl, oxazolyl, isoxazolyl, thiazolyl, oxadiazolyl, pyrrolyl, pyrazolyl, imidazolyl, triazolyl or tetrazolyl ring moiety, wherein said ring moiety contains 0 or 1 of CR$^A$ and NR$^A$;

wherein ring Q, Q$^4$, R and n are as defined herein, and specifically as defined in Formula (I); and X, $R^5$, L, and B are as defined herein, or a salt, particularly a pharmaceutically acceptable salt, thereof.

In selected embodiments, $A^1$ is C, $A^4$ is C or N, and $A^2$, $A^3$, and $A^5$ are each independently selected from CH, O, N, and NH to form an oxazolyl, isoxazolyl, oxadiazolyl, pyrrolyl, pyrazolyl, imidazolyl, triazolyl or tetrazolyl ring moiety.

In other selected embodiments, $A^1$ and $A^4$ are each C, and $A^2$, $A^3$ and $A^5$ are each independently selected from N and NH to form a triazolyl ring moiety.

Another embodiment of this invention, wherein A is piperidinyl or pyrrolidinyl, may be represented by Formula (IV):

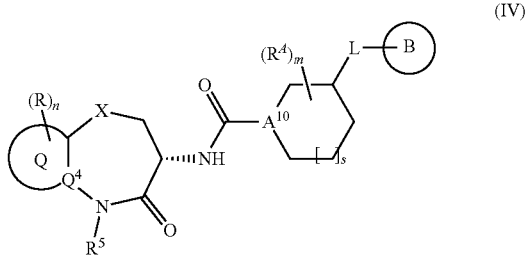

(IV)

wherein s is 0 or 1, $A^{10}$ is N, ring Q, $Q^4$, R and n are as defined herein, and specifically as defined in Formula (I); and X, $R^5$, $R^A$, m, L, and B are as defined herein. In specific embodiments, m is 0 and A is an unsubstituted piperidinyl or pyrrolidinyl moiety.

In one embodiment of the compounds of this invention, m is 0. In another embodiment, m is 1 and $R^A$ is $(C_1-C_4)$alkyl, specifically $R^A$ is $(C_1-C_2)$alkyl. In selected embodiments, $R^A$ is methyl.

A further embodiment of this invention, wherein A is phenyl, pyridinyl, or pyridinyl-N-oxide, may be represented by Formula (V):

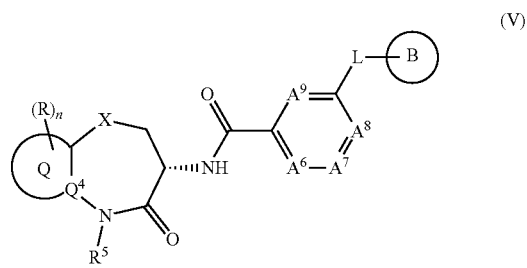

(V)

wherein:
$A^6$, $A^7$, $A^8$, and $A^9$ are each CH;
one of $A^6$, $A^7$, $A^8$, and $A^9$ is $CR^A$ and the others of $A^6$, $A^7$, $A^8$, and $A^9$ are CH;
one of $A^6$, $A^7$, $A^8$, and $A^9$ is N and the others of $A^6$, $A^7$, $A^8$, and $A^9$ are CH;
one of $A^6$, $A^7$, $A^8$, and $A^9$ is N—O and the other of $A^6$, $A^7$, $A^8$, and $A^9$ are CH;
ring Q, $Q^4$, R and n are as defined herein, and specifically as defined in Formula (I);
and X, $R^5$, L, and B are as defined herein.

In one embodiment of the compounds of this invention, L is O, S, NH, N(CH$_3$), CH$_2$, CH$_2$CH$_2$, CH(CH$_3$), CHF, CF$_2$, CH$_2$O, CH$_2$N(CH$_3$), CH$_2$NH, or CH(OH). In another embodiment, L is O, S, N(CH$_3$), CH$_2$, CH$_2$CH$_2$, CH(CH$_3$), CF$_2$, CH$_2$O, CH$_2$N(CH$_3$), or CH(OH). In another embodiment, L is CH$_2$O, CH$_2$CH$_2$, CH$_2$NH, or CH$_2$N(CH$_3$). In a further embodiment, L is N(CH$_3$), CH(CH$_3$), or CH(OH). In another further embodiment, L is -(R)CH(CH$_3$). In a still further embodiment, L is O, CH$_2$, or NH. In one selected embodiment, L is O. In another selected embodiment, L is CH$_2$.

In one embodiment of the compounds of this invention, B is an optionally substituted $(C_3-C_6)$cycloalkyl, phenyl, 5-6 membered heteroaryl, or 5-6 membered heterocycloalkyl; wherein said $(C_3-C_6)$cycloalkyl, phenyl, 5-6 membered heteroaryl, or 5-6 membered heterocycloalkyl is unsubstituted or is substituted by one or two substituents each independently selected from halogen, $(C_1-C_4)$alkyl, halo$(C_1-C_4)$alkyl, $(C_1-C_4)$alkoxy, halo$(C_1-C_4)$alkoxy, nitro, and $(C_1-C_4)$alkylC(O)—. In one embodiment of the compounds of this invention, B is an optionally substituted 5-6 membered heteroaryl or 5-6 membered heterocycloalkyl. In one embodiment, B is an optionally substituted pyrazolyl, thienyl, pyridinyl (pyridyl), oxo-pyridyl, pyrimidinyl, isoxazolyl, morpholinyl, tetrahydropyranyl or tetrahydrofuranyl, wherein the pyrazolyl, thienyl, pyridinyl (pyridyl), oxo-pyridyl, pyrimidinyl, isoxazolyl, morpholinyl, tetrahydropyranyl or tetrahydrofuranyl is optionally substituted by one or two independently selected $(C_1-C_4)$alkyl substituents. In another embodiment, B is an optionally substituted pyrazolyl, thienyl, pyridinyl (pyridyl), oxo-pyridyl, pyrimidinyl, isoxazolyl, morpholinyl, or tetrahydrofuranyl, wherein the pyrazolyl, thienyl, pyridinyl (pyridyl), oxo-pyridyl, pyrimidinyl, isoxazolyl, morpholinyl, or tetrahydrofuranyl is optionally substituted by one or two independently selected $(C_1-C_4)$alkyl substituents.

In another embodiment of the compounds of this invention, B is unsubstituted $(C_3-C_6)$cycloalkyl or phenyl. In a selected embodiment of this invention, B is unsubstituted cyclopropyl, cyclobutyl, cyclopentyl or cyclohexyl. In a specific embodiment, B is unsubstituted cyclopentyl or cyclohexyl. In another selected embodiment of the compounds of this invention, B is unsubstituted phenyl.

In another selected embodiment, B is substituted phenyl. In one embodiment, B is phenyl, substituted by 1 or 2 substituents independently selected from halogen, $(C_1-C_4)$alkyl, halo$(C_1-C_4)$alkyl, $(C_1-C_4)$alkoxy, halo$(C_1-C_4)$alkoxy, nitro, and $(C_1-C_4)$alkylC(O)—. In other embodiments, B is phenyl, substituted by 1 or 2 substituents independently selected from halogen, $(C_1-C_3)$alkyl and $(C_1-C_3)$alkoxy. In specific embodiments, B is phenyl, substituted by 1 or 2 substituents independently selected from iodo, fluoro, chloro, bromo, methyl and methoxy.

In one selected embodiment, B is phenyl, substituted by 1 or 2 substituents independently selected from fluoro, chloro, bromo, and methyl, specifically B is phenyl, substituted by 1 or 2 fluoro substituents.

In one embodiment of the compounds of this invention, the moiety -L-B is $(C_3-C_6)$alkyl, $(C_3-C_6)$alkoxy, halo$(C_3-C_6)$alkoxy, $(C_3-C_6)$alkenyl, or $(C_3-C_6)$alkenyloxy. In another embodiment, the moiety -L-B is $(C_3-C_6)$alkyl, $(C_3-C_6)$alkoxy, or $(C_3-C_5)$alkenyloxy.

In one embodiment, the compounds of this invention is selected from: 5-benzyl-N-(6,8-dimethyl-2-oxo-2,3,4,5-tetrahydro-1H-thieno[3,4-b]azepin-3-yl)-4H-1,2,4-triazole-3-carboxamide; 5-benzyl-N-(5-oxo-5,6,7,8-tetrahydro-4H-thieno[3,2-b]azepin-6-yl)-4H-1,2,4-triazole-3-carboxamide; 5-benzyl-N-(2-methyl-5-oxo-5,6,7,8-tetrahydro-4H-thieno[3,2-b]azepin-6-yl)-4H-1,2,4-triazole-3-carboxamide; 5-benzyl-N-(1-methyl-5-oxo-1,4,5,6,7,8-hexahydropyrrolo[3,2-b]azepin-6-yl)-4H-1,2,4-triazole-3-carboxamide; 5-benzyl-N-(1,3-dimethyl-5-oxo-1,4,5,6,7,8-hexahydropyrrolo[3,2-b]azepin-6-yl)-4H-1,2,4-triazole-3-carboxamide; 5-benzyl-N-(2-oxo-1,2,3,4,5,6-hexahydroazepino[3,2-b]indol-3-yl)-4H-1,2,4-triazole-3-carboxamide; (S)-5-benzyl-N-(3,4-dimethyl-5-oxo-5,6,7,8-tetrahydro-4H-isothiazolo[4,5-b][1,4]diazepin-6-yl)-4H-1,2,4-triazole-3-carboxamide; (R)-5-benzyl-N-(4-oxo-2,3,4,5-tetrahydropyrrolo[2,1-b][1,3,4]thiadiazepin-3-yl)-4H-1,2,4-triazole-3-carboxamide; (R)-5-benzyl-N-(5-methyl-4-oxo-2,3,4,5-tetra hydropyrrolo[2,1-b][1,3,4]thiadiazepin-3-yl)-4H-1,2,4-triazole-3-carboxamide; and 5-benzyl-N-(2-oxo-2,3,4,5,7,8,9,10-octahydro-1H-benzofuro[3,2-b]azepin-3-yl)-4H-1,2,4-triazole-3-carboxamide; or a tautomer thereof.

Representative compounds of this invention include the compounds in Examples 1-10.
Compounds considered part of the invention include:
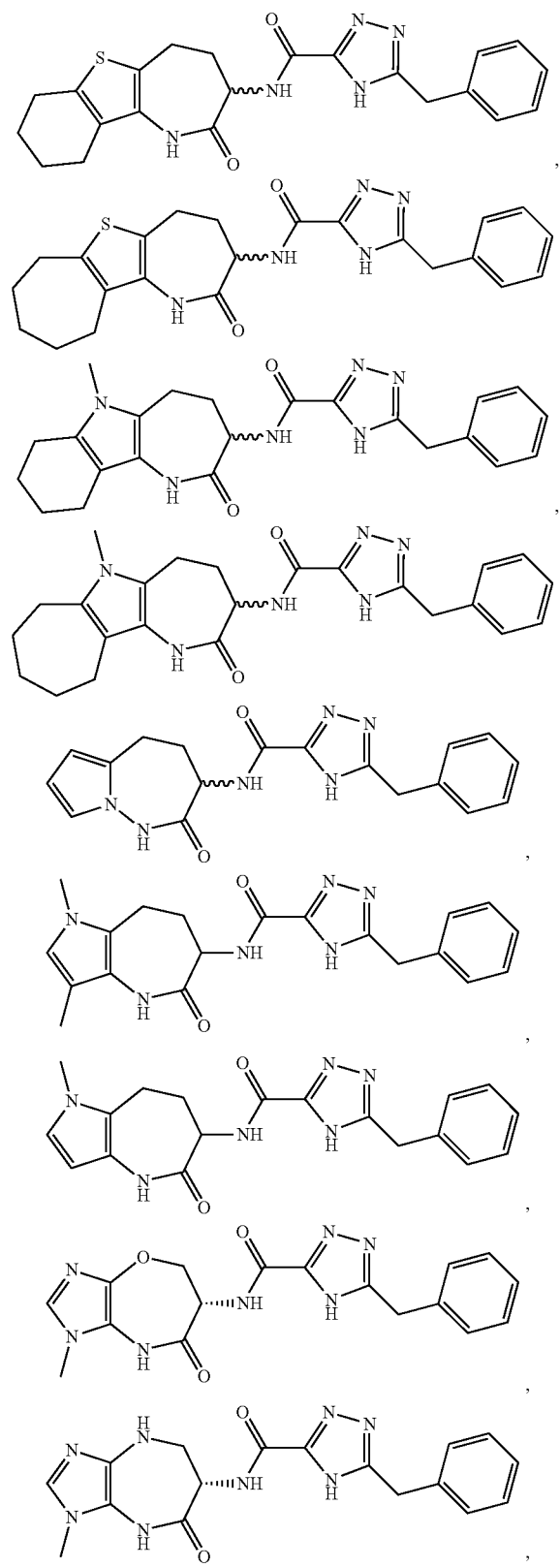
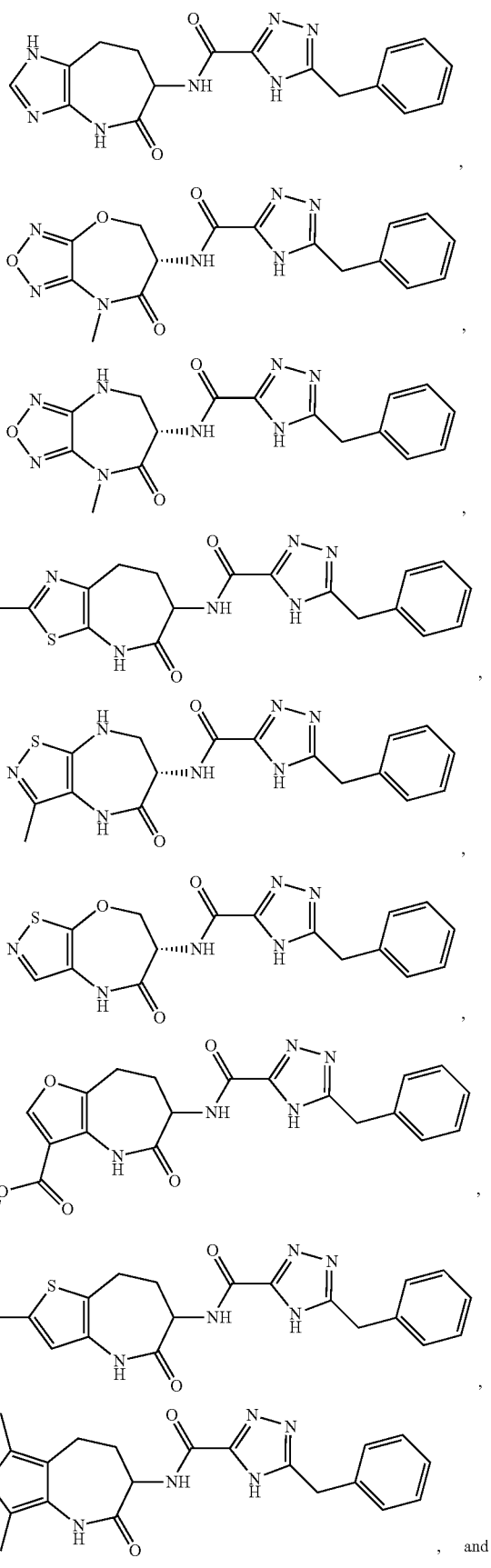
, and

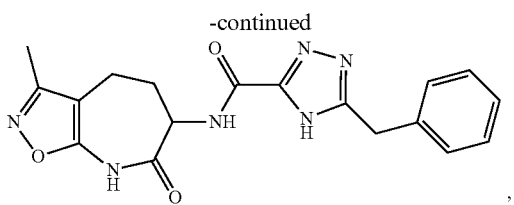

or a tautomer thereof.

In specific embodiments, the compounds of this invention include:

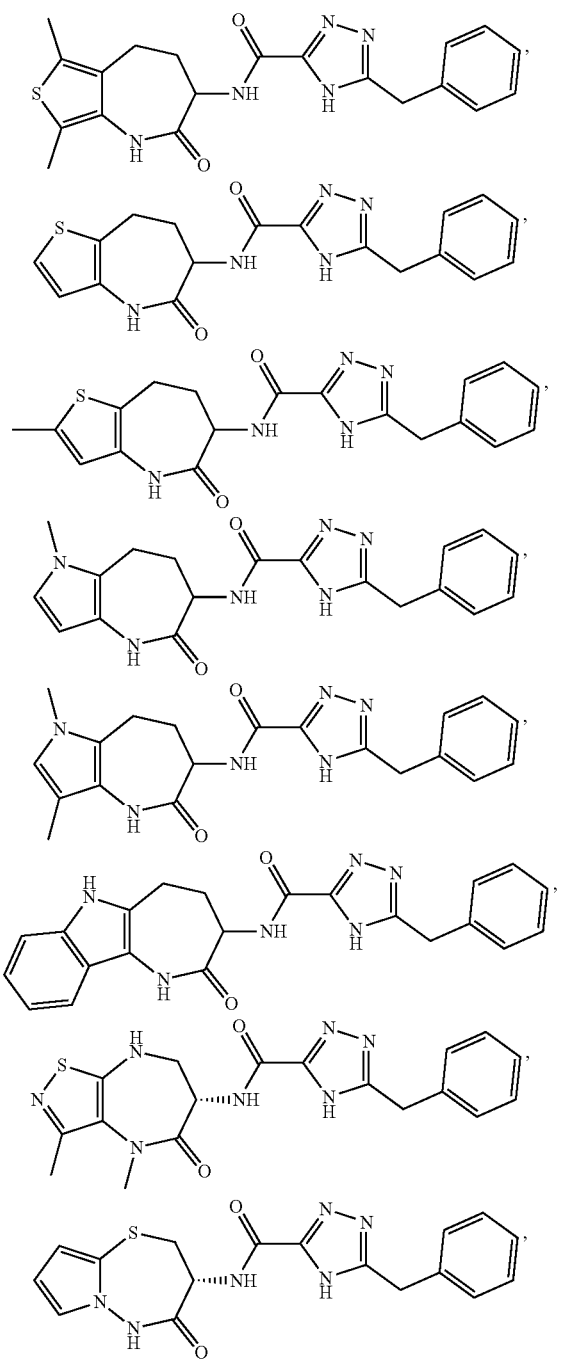

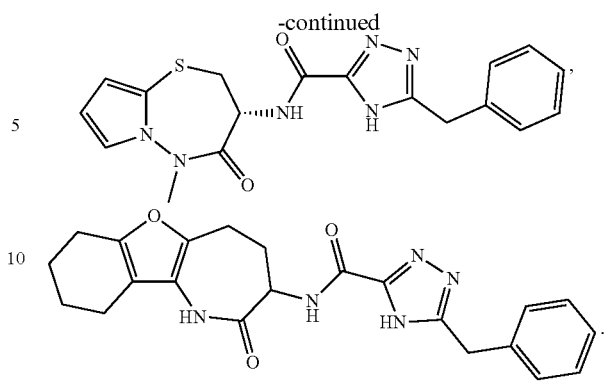

or a tautomer thereof.

It will be appreciated that the present invention encompasses compounds of Formula (I), more specifically, the compounds of Formulas (I), (II), (III), (IV), and (V), as the free base and as salts thereof, for example as a pharmaceutically acceptable salt thereof. In one embodiment the invention relates to compounds of Formula (I), in the form of a free base. In another embodiment the invention relates to compounds of Formula (I), in the form of a salt, particularly, a pharmaceutically acceptable salt. It will be further appreciated that, in one embodiment, the invention relates to compounds of the Examples in the form of a free base. In another embodiment the invention relates to compounds of the Examples in the form of a salt, particularly, a pharmaceutically acceptable salt.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). For example, commercially available deuterated starting materials may be employed in the preparation of deuterated analogs of the compounds of Formula (I), or they may be synthesized using conventional techniques employing deuterated reagents (e.g. by reduction using lithium aluminum deuteride or sodium borodeuteride or by metal-halogen exchange followed by quenching with $D_2O$ or methanol-$d_3$).

The skilled artisan will appreciate that solvates (particularly, hydrates) of a compound of Formula (I), including solvates of salts of a compound of Formula (I), may be formed when solvent molecules are incorporated into the crystalline lattice during crystallization. The present invention includes within its scope all possible stoichiometric and non-stoichiometric salt and/or hydrate forms.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

It is well known and understood to those skilled in the art that the apparatus employed, humidity, temperature, orientation of the powder crystals, and other parameters involved in obtaining a powder X-ray diffraction (PXRD) pattern may cause some variability in the appearance, intensities, and positions of the lines in the diffraction pattern. A person skilled in the art is capable of determining if a sample of a crystalline compound has the same form as, or a different form from, a known form by comparison of their PXRD patterns. For example, one skilled in the art can overlay a PXRD pattern of a test sample of a crystalline form with the PXRD pattern of a known form, and using expertise and knowledge in the art, readily determine whether the PXRD pattern of the sample is substantially in accordance with the PXRD pattern of the known form. If the PXRD pattern is substantially in accordance with the known form, the sample form can be readily and accurately identified as having the same form as the known crystalline form. Similarly, a person skilled in the art is capable of determining if a given diffraction angle (expressed in °2θ) obtained from a PXRD pattern is at about the same position as a recited value.

Because of their potential use in medicine, the salts of the compounds of Formula (I) are preferably pharmaceutically acceptable. Suitable pharmaceutically acceptable salts can include acid or base addition salts.

As used herein, the term "pharmaceutically acceptable" means a compound which is suitable for pharmaceutical use. Salts and solvates (e.g. hydrates and hydrates of salts) of the compounds of Formula (I) which are suitable for use in medicine are those wherein the counterion or associated solvent is pharmaceutically acceptable.

Salts and solvates having non-pharmaceutically acceptable counterions or associated solvents are within the scope of the present invention, for example, for use as intermediates in the preparation of other compounds of Formula (I) and their salts and solvates.

Salts may be prepared in situ during the final isolation and purification of a compound of Formula (I), more specifically, a compound of Formulas (I), (II), (III), (IV), and (V). If a basic compound of Formula (I) is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a disclosed compound containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound. This invention also provides for the conversion of one salt of a compound of this invention, e.g., a hydrochloride salt, into another salt of a compound of this invention, e.g., a sulfate salt.

Salts of the compounds of Formula (I) containing a basic amine or other basic functional group may be prepared by any suitable method known in the art, such as treatment of the free base with an acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, proprionate, pyroglutamate, salicylate, sebacate, stearate, succinate, sulfate, tartrate, thiocyanate, p-toluenesulfonate (tosylate), undecylenate, 1-hydroxy-2-naphthoate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N-bisdehydroabietylamine, glucamine, N methylglucamine, collidine, choline, quinine, quinoline, and basic amino acids such as lysine and arginine.

It will be understood that if a compound of Formula (I) contained two or more basic moieties, the stoichiometry of salt formation may include 1, 2 or more equivalents of acid. Such salts would contain 1, 2 or more acid counterions, for example, a diacetate or a dihydrochloride salt.

Because the compounds of Formula (I), or a pharmaceutically acceptable salt thereof, are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of this invention may be particularly useful for the treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit.

In this invention, RIP1 kinase-mediated diseases or disorders are diseases or disorders that are mediated by activation of RIP1 kinase, and as such, are diseases or disorders where inhibition of RIP1 kinase would provide benefit. Such RIP1 kinase-mediated diseases or disorders are diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment (and degeneration), retinitis pigmentosa, macular degeneration, pancreatitis, atopic dermatitis, arthritis (including rheumatoid arthritis, spondyloarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)) Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), neontal hypoxic brain injury, allergic diseases (including asthma and atopic dermatitis), burns, multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, peridontitis, NEMO-mutations (mutations of NF-kappa-B essential modulator gene (also known as IKK gamma or IKKG)), particularly, NEMO-deficiency syndrome, HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as influenza, staphylococcus, and mycobacterium (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), Stevens-Johnson syndrome, toxic epidermal necrolysis, or for the treatment of cells ex vivo to preserve vitality and function.

The compounds of the invention, particularly the compounds of Formula (I), more specifically, the compounds of Formulas (I), or a pharmaceutically acceptable salt thereof, may be particularly useful for the treatment of the following RIP1 kinase-mediated diseases or disorders, that is, diseases/disorders which are likely to be regulated at least in part by RIP1 kinase activity, particularly inflammatory bowel disease (including Crohn's disease and ulcerative colitis), rheumatoid arthritis, chronic obstructive pulmonary disease (COPD), asthma, cigarette smoke-induced damage, cystic fibrosis, psoriasis, retinal detachment and degeneration, retinitis pigmentosa, macular degeneration, atopic dermatitis, burn injury, periodontitis, a bacterial or viral infection (an infection with a pathogen including but not limited to influenza, staphylococcus, and/or mycobacterium (tuberculosis), systemic scleroderma (particularly, topical treatment of hardened and/or tightened skin areas), and/or ischemia reperfusion injury of solid organs/transplant rejection (particularly, topical treatment of donor organ (particularly kidney, liver, and heart and/or lung transplants), infusion of organ recipient), and topical treatment of bowels.

The compounds of the invention, particularly the compounds of Formula (I), more specifically, the compounds of Formulas (I), or a pharmaceutically acceptable salt thereof, may be particularly useful for the treatment of the following RIP1 kinase-mediated disease or disorder: rheumatoid arthritis, inflammatory bowel disease (including Crohn's disease and ulcerative colitis), and psoriasis.

The compounds of the invention, particularly the compounds of Formula (I), more specifically, the compounds of Formulas (I), or a pharmaceutically acceptable salt thereof, may be particularly useful for the treatment of the following RIP1 kinase-mediated disease or disorder: Crohn's disease, ulcerative colitis, psoriasis, rheumatoid arthritis, spondyloarthritis, systemic onset juvenile idiopathic arthritis, psoriatic arthritis, osteoarthritis, ischemia reperfusion injury of solid organs, sepsis, systemic inflammatory response syndrome, multiple sclerosis, or a solid organ malignancy.

The treatment of the above-noted diseases/disorders may concern, more specifically, the amelioration of organ injury or damage sustained as a result of the noted diseases/disorders. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis, or overdose of acetaminophen.

The compounds of this invention may be particularly useful for amelioration of solid organ tissue (particularly kidney, liver, and heart and/or lung) injury or damage following transplant or the administration of nephrotoxic drugs or substances e.g. cisplatin. It will be understood that amelioration of such tissue damage may be achieved where possible, by pre-treatment with a compound of Formula (I), or a pharmaceutically acceptable salt thereof; for example, by pre-treatment of a patient prior to administration of cisplatin or pre-treatment of an organ or the organ recipient prior to transplant surgery. Amelioration of such tissue damage may be achieved by treatment with a compound of Formula (I) or a pharmaceutically acceptable salt thereof, during transplant surgery. Amelioration of such tissue damage may also be achieved by short-term treatment of a patient with a compound of Formula (I), or a pharmaceutically acceptable salt thereof, after transplant surgery.

Treatment of RIP1-mediated disease conditions may be achieved using a compound of the invention, particularly a compound of Formula (I), or a pharmaceutically acceptable salt thereof, of as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of the invention, particularly the compounds of Formula (I), or a pharmaceutically acceptable salt thereof, may be employed alone or in combination with one or more other therapeutically active agents, e.g., pharmaceutically active compounds or biologic products (e.g., monoclonal antibodies). Combination therapies according to the present invention thus comprise the administration of at least one compound of the invention, particularly a compound of Formula (I), or a pharmaceutically acceptable salt thereof, and at least one other therapeutically active agent. Preferably, combination therapies according to the present invention comprise the administration of at least one compound of the invention, particularly a compound of Formula (I), or a pharmaceutically acceptable salt thereof, and at least one other therapeutically active agent, specifically one or two other therapeutically active agents, more specifically one other therapeutically active agent.

For example, amelioration of tissue damage may be achieved by treatment with a compound of Formula (I), or a pharmaceutically acceptable salt thereof, and at least one other therapeutically active agent during transplant surgery. Amelioration of tissue damage may also be achieved by short-term treatment of a patient with a compound of Formula (I), or a pharmaceutically acceptable salt thereof, and at least one other therapeutically active agent after transplant surgery. Amelioration of tissue damage ex vivo, that is ex vivo preservation of tissues, organs and cells may also be achieved by short-term treatment of tissues, organs and cells with a compound of Formula (I), or a pharmaceutically acceptable salt thereof, and at least one other therapeutically active agent, prior to or during transplant surgery.

The compound(s) of the invention, particularly the compounds of Formula (I), or pharmaceutically acceptable salts thereof, and the other therapeutically active agent(s) may be administered together in a single pharmaceutical composition or separately and, when administered separately this may occur simultaneously or sequentially in any order. The amounts of the compound(s) of the invention, particularly a compound of Formula (I), or pharmaceutically acceptable salts thereof, and the other therapeutically active agent(s) and the relative timings of administration will be selected in order to achieve the desired combined therapeutic effect. Thus in a further aspect, there is provided a combination comprising a compound of the invention, particularly a compound of Formula (I) or a pharmaceutically acceptable salt thereof, together with at least one other therapeutically active agent, specifically one or two other therapeutically active agents, more specifically one other therapeutically active agent.

Thus, in one aspect of this invention, a compound of the invention, particularly a compound of Formula (I), or a pharmaceutically acceptable salt thereof, or a pharmaceutical composition comprising a compound of the invention, particularly a compound of Formula (I), or a pharmaceutically acceptable salt thereof, may be used in combination with or include at least one other therapeutically active agent, for example an anti-inflammatory agent and/or an anti-TNF agent.

The pharmaceutical compositions of the invention typically contain one compound of the invention. However, in certain embodiments, the pharmaceutical compositions of the invention contain more than one compound of the invention. In other embodiments, the pharmaceutical compositions of the invention may comprise at least one other therapeutically active agent, specifically one or two other therapeutically active agents, more specifically one other therapeutically active agent.

A compound that inhibits RIP1 kinase, particularly a compound of Formula (I) or a pharmaceutically acceptable salt thereof, may be administered in combination with other anti-inflammatory agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL17 biologics, anti-CD22, anti-integrin agents, anti-IFNa, anti-CD20 or CD4 biologics and other cytokine inhibitors or biologics to T-cell or B-cell receptors or interleukins.

In the treatment of CVA, a compound that inhibits RIP1 kinase, particularly a compound of Formula (I) or a pharmaceutically acceptable salt thereof, may be administered to in combination with a thrombolytic agent (such as tissue plasminogen activator (TPA®), Activase®, Lanoteplase®, Reteplase®, Staphylokinase®, Streptokinase®, Tenecteplase®, Urokinase®, an anticoagulant (such as heparin, coumadin, clopidrogel (Plavix®), and a platelet aggregation inhibitor (such as dipyridamole (Persantine®), ticlopidine HCL (Ticlid®), eptifibatide (Integrillin®), and/or aspirin).

In the treatment of SIRS, a compound that inhibits RIP1 kinase, particularly a compound of Formula (I) or a pharmaceutically acceptable salt thereof, may be administered in combination with a broad-spectrum antibiotic (such as vacomycin) or other anti-MRSA therapy (cefeprime (Maxipime®), piperacillin/tazobactam (Zosyn®), carbapenem (imipenem, meropenem, doripenem), quinolones (ciprofloxacin, levofloxacin, ofloxacin, moxifloxacin, etc.), and low dose steroids such as hydrocortisones.

In the treatment of inflammatory bowel disease (particularly, Crohn's disease and/or ulcerative colitis), a compound that inhibits RIP1 kinase, particularly a compound of Formula (I) or a pharmaceutically acceptable salt thereof, may be administered in combination with vedolizumab (Entyvio®), alicaforsen, or remestemcel-L (Prochymal®).

In the treatment of psoriasis, a compound that inhibits RIP1 kinase, particularly a compound of Formula (I) or a pharmaceutically acceptable salt thereof, may be administered in combination with ixekizumab, tildrakizumab (MK-3222), or secukinumab (AIN457).

In the treatment of periodonitis, a compound that inhibits RIP1 kinase, particularly a compound of Formula (I) or a pharmaceutically acceptable salt thereof, may be administered in combination with an antimicrobial agent, (such as chlorhexidine (Peridex®, PerioChip®, PerioGard®, etc.)) or an antibiotic (such as doxycycline (Vibrox®, Periostat®, Monodox®, Oracea®, Doryx®, etc.) or minocycline (Dynacin®, Minocin®, Arestin®, Dynacin®, etc.).

In the treatment of asthma, a compound that inhibits RIP1 kinase, particularly a compound of Formula (I) or a pharmaceutically acceptable salt thereof, may be administered in combination with an inhaled corticosteroid ((ICS) such as fluticasone proprionate (Flovent®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-dur®, Uniphyl®), a mast cell inhibitor (such as cromulyn sodium (Nasalcrom®) and nedocromil sodium (Tilade®), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta® Neohaler®), an epinephrine inhalation aerosol (E004), fluticasone furoate/fluticasone proprionate, vinanterol inhalation/fluticasone furoate powder (Relovair™), fluticasone propionate/eformoterol fumarate dehydrate (Flutiform®), reslizumab, salbutamol dry-powder inhalation, tiotropium bromide (Spiriva®HandiHaler®), formoterol/budesonide (Symbicort®SMART®@), fluticasone furoate (Veramyst®), Vectura's VR506, lebrikizumab (RG3637), a combination phosphodiesterase (PDE)-3 and (PDE)-4 inhibitor (RPL554).

In the treatment of COPD, a compound that inhibits RIP1 kinase, particularly a compound of Formula (I) or a pharmaceutically acceptable salt thereof, may be administered in combination with a LABA (such as salmeterol xinafoate (Serevent), umeclidinium/vilanterol (Anuro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate (ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In the treatment of a mycobacterium infection (tuberculosis), a compound that inhibits RIP1 kinase, particularly a compound of Formula (I) or a pharmaceutically acceptable salt thereof, may be administered in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), or delamanid (OPC-67683).

In the treatment of systemic scleroderma, a compound that inhibits RIP1 kinase, particularly a compound of Formula (I) or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®)), diltaizem (Cardizem®, Cardizem SR®, Cardizem CD®, Cardia®, Dilacor®, Tiazac)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (KMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In the treatment of cystic fibrosis, a compound that inhibits RIP1 kinase, particularly a compound of Formula (I) or a pharmaceutically acceptable salt thereof, may be administered in combination with a cystic fibrosis transmembrane conductance regulator (CFTR) potentiator (ivacftor (Kalydeco®)) a mucolytic agent (such as dornase alpha (Pulmozyme®)), pancreatic enzymes (such as Pancrelipase (Creon®, Pancreaze®, Ultresa®, Zenpep®)), a bronchodilator (such as albuterol (AccuNeb®, ProAir®, Proventil HFA®, VoSpire ER®, Ventolin HFA®)), an antibiotic (including inhaled, oral or parenteral, such as tobramycin solution for inhalation (TOBI®, Bethkis®, TOBI Podhaler®), aztreonam inhalation (Azactam®, Cayston®), colistimethate sodium (Coly-Mycin®), cephalosporins (cefadroxil monohydrate (Duricef®), cefazolin (Kefzol®), cephalexin (Keflex®), cefazolin (Ancef®, etc.), fluoroquinolones (moxifloxacin, levofloxacin, gemifloxacin, etc), azithromycin (Zithromax®), gentamicin (Garamycin®), piperacillin/tazobacam (Zosyn®), cephalexin (Keflex), ceftazidime (Fortaz, Tazicef), ciprofloxin (Cipro XR, Proquin XR), trimethoprim/sulfamethoxazole (Bactrim DS, Septra DS), chloramphenicol)), or ivacftor (Kalydeco®)/lumacaftor (VX-809), ataluren (Translarna®), or with tiopropium bromide (Spiriva® Handihaler®) as add on to standard therapy.

In the treatment of retinitis pigmentosa, a compound that inhibits RIP1 kinase, particularly a compound of Formula (I) or a pharmaceutically acceptable salt thereof, may be administered in combination with a ciliary neurtrophic growth factor (NT-501-CNTF) or gene transfer agent, UshStat®.

In the treatment of macular degeneration, a compound that inhibits RIP1 kinase, particularly a compound of Formula (I) or a pharmaceutically acceptable salt thereof, may be administered in combination with opthalmalic intravitreal injections (afibercept (Eylea®)) or with an anti-vascular endothelial growth factor (VEGF) inhibitor (such as ranibizumab (Lucentis®) or pegaptanib sodium (Macugen®)), a ciliary neurotrophic growth factor agent (NT501), iSONEP®, or bevacizumab (Avastin®).

In the treatment of influenza, a compound that inhibits RIP1 kinase, particularly a compound of Formula (I) or a pharmaceutically acceptable salt thereof, may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®

In the treatment of a staphylococcus infection, a compound that inhibits RIP1 kinase, particularly a compound of Formula (I) or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In the treatment of transplant rejection, a compound that inhibits RIP1 kinase, particularly a compound of Formula (I) or a pharmaceutically acceptable salt thereof, may be administered in combination with a high-dose corticosteroid (such as prednisone (Deltasone®), methylprednisolone (SoluMedrol®) etc.) a calcineurin inhibitor (such as cyclosporine (Sandimmune®, Neoral®, Gengraf®), tacrolimus (Prograf®, Astragraf XL®)), an mTor inhibitor (such as sirolimus (Rapamune®) or everolimus (Afinitor®)), an antiproliferative agent (such as azathioprine (Imuran®, Azasan®), mycophenolate mofetil (CellCept®), or mycophenolate sodium (Myfortic®)), a monoclonal antibody (such as muromonab-CD3 (Orthoclone OKT3®)), an interleukine-2 receptor antagonist ((Basiliximab®, Simulect®), daclizumab (Zenapax®), or rituximab (Rituxan®)), a polyclonal anti-T-cell antibody (such as anti-thymocyte gamma globulin-equine (Atgam®), or antithymocyte globulin-rabbit (Thymoglobulin®)) an anti-CD40 antagonist (ASKP-1240), a JAK inhibitor (ASP015K), or an anti-TCR murine mAb (TOL101).

In the treatment of atopic dermatitis, a compound that inhibits RIP1 kinase, particularly a compound of Formula (I) or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®)), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), anon-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

In one embodiment of this invention, the at least one other therapeutically active agent is selected from a thrombolytic agent, a tissue plasminogen activator, an anticoagulant, and a platelet aggregation inhibitor. In another embodiment, the at least one other therapeutically active agent is selected from heparin, coumadin, clopidrogel, dipyridamole, ticlopidine HCL, eptifibatide, and aspirin. In one embodiment, the RIP1 kinase-mediated disease or disorder treated with these agents is a cerebrovascular accident.

In one embodiment of this invention, the at least one other therapeutically active agent is selected from broad-spectrum antibiotic, anti-MRSA therapy and a low dose steroid. In another embodiment, the at least one other therapeutically active agent is selected from vacomycin, cefeprime, a combination of piperacillin and tazobactam, imipenem, meropenem, doripenem, ciprofloxacin, levofloxacin, ofloxacin, moxifloxacin, and hydrocortisone. In one embodiment, the RIP1 kinase-mediated disease or disorder treated with these agents is systemic inflammatory response syndrome.

In one embodiment of this invention, the at least one other therapeutically active agent is alicaforse or remestemcel-L. In one embodiment, the RIP1 kinase-mediated disease or disorder treated with these agents is Crohn's disease or ulcerative colitis.

In one embodiment of this invention, the at least one other therapeutically active agent is ixekizumab, or tildrakizumab. In one embodiment, the RIP1 kinase-mediated disease or disorder treated with these agents is psoriasis.

In one embodiment of this invention, the at least one other therapeutically active agent is an antimicrobial agent or an antibiotic. In another embodiment, the at least one other therapeutically active agent is selected from chlorhexidine, doxycycline and minocycline. In one embodiment, the RIP1 kinase-mediated disease or disorder treated with these agents is periodontitis.

In one embodiment of this invention, the at least one other therapeutically active agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. In another embodiment, the at least one other therapeutically active agent is selected from fluticasone proprionate, beclomethasone dipropionate, budesonide, trimcinolone acetonide, flunisolide, mometasone fuorate, or ciclesonide, formoterol fumarate, salmeterol xinafoate, a combination of fluticasone furoate and vilanterol, a combination of formoterol and budesonide inhalation, a combination of beclomethasone dipropionate and formoterol, a combination of fluticasone propionate and salmeterol, albuterol sulfate, levalbuterol tartrate, a combination of ipratropium bromide and albuterol, ipratropium bromide, montelukast sodium, zafirlukast, zileuton, omalizumab theophylline, cromulyn sodium, nedocromil sodium, and a combination of mometasone furoate and formoterol fumarate dihydrate. In another embodiment, the at least one other therapeutically active agent is selected from protein tyrosine kinase inhibitor, a CRTH2/D-prostanoid receptor antagonist, an epinephrine inhalation aerosol, and a combination of a phosphodiesterase-3 inhibitor and a phosphodiesterase-4 inhibitor. In another embodiment, the at least one other therapeutically active agent is selected from masitinib, AMG 853, indacaterol, E004, a combination of fluticasone furoate and fluticasone proprionate, a combination of vinanterol fluticasone furoate, a combination of fluticasone propionate and eformoterol fumarate dehydrate, reslizumab, salbutamol, tiotropium bromide, a combination of formoterol and budesonide, fluticasone furoate, VR506, lebrikizumab, and RPL554. In one embodiment, the RIP1 kinase-mediated disease or disorder treated with these agents is asthma.

In one embodiment of this invention, the at least one other therapeutically active agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. In another embodiment, the at least one other therapeutically active agent is selected from salmeterol xinafoate, a combination of umeclidinium and vilanterol, umeclidinium, aformoterol tartrate, formoterol fumarate, indacterol maleate, a combination of fluticasone propionate and eformoterol fumarate dehydrate, tiotropium bromide, aclidinium bromide, roflumilast, a combination of fluticasone furoate and vilanterol, a combination of fluticasone propionate and salmeterol, a combination of budesonide and formoterol, a combination of mometasone and formoterol, a combination of ipratropium bromide and albuterol sulfate, a combination of albuterol and ipratropium, ipratropium bromide, albuterol sulfate, budesonide, fluticasone propionate, and beclometasone dipropionate. In another embodiment, the at least one other therapeutically active agent is selected from SCH527123, glycoprronium bromide, a combination of glycopyrronium bromide and indacaterol maleate, a combination of glycopyrrolate and formoterol fumarate, indacaterol maleate, olodaterol, tiotropium, olodaterol, and a combination of aclidinium and formoterol. In one embodiment, the RIP1 kinase-mediated disease or disorder treated with these agents is COPD.

In one embodiment of this invention, the at least one other therapeutically active agent is an antimycobacterial agent or a bactericidal antibiotic. In another embodiment, the at least one other therapeutically active agent is selected from isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, and delamanid. In one embodiment, the RIP1 kinase-mediated disease or disorder treated with these agents is a mycobacterium infection.

In one embodiment of this invention, the at least one other therapeutically active agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. In another embodiment, the at least one other therapeutically active agent is selected from prednisolone, anti-thymocyte globulin, FK506 (tacrolimus), thalidomide, chlorambucil, nifedipine, nicardipine, nitroglycerin ointment, lisinopril, diltaizem, fluoxetine, bosentan, epoprostenol, colchicines, para-aminobenzoic acid, dimethyl sulfoxide, D-penicillamine, interferon alpha, interferon gamma (INF-g)), omeprazole, metoclopramide, lansoprazole, esomeprazole, pantoprazole, rabeprazole, imatinib, ARG201, and tocilizumab. In one embodiment, the RIP1 kinase-mediated disease or disorder treated with these agents is systemic scleroderma.

In one embodiment of this invention, the at least one other therapeutically active agent is selected from a cystic fibrosis transmembrane conductance regulator potentiator, a mucolytic agent, pancreatic enzymes, a bronchodilator, an antibiotic, or ivacftor/lumacaftor, ataluren, and tiopropium bromide. In another embodiment, the at least one other therapeutically active agent is selected from ivacftor, dornase alpha, pancrelipase, albuterol, tobramycin, aztreonam, colistimethate sodium, cefadroxil monohydrate, cefazolin, cephalexin, cefazolin, moxifloxacin, levofloxacin, gemifloxacin, azithromycin, gentamicin, piperacillin/tazobacam, ceftazidime, ciprofloxin, trimethoprim/sulfamethoxazole, chloramphenicol, or ivacftor/lumacaftor, ataluren, and tiopropium bromide. In one embodiment, the RIP1 kinase-mediated disease or disorder treated with these agents is cystic fibrosis.

In one embodiment of this invention, the at least one other therapeutically active agent is a ciliary neurtotrophic growth factor or a gene transfer agent. In another embodiment, the at least one other therapeutically active agent is NT-501-CNTF or a gene transfer agent encoding myosin VIIA (MY07A). In one embodiment, the RIP1 kinase-mediated disease or disorder treated with these agents is retinitis pigmentosa.

In one embodiment of this invention, the at least one other therapeutically active agent is selected from opthalmalic intravitreal injections, an anti-vascular endothelial growth factor inhibitor, and a ciliary neurotrophic growth factor agent. In another embodiment, the at least one other therapeutically active agent is selected from afibercept, ranibizumab, pegaptanib sodium, NT501, humanized sphingomab, and bevacizumab. In one embodiment, the RIP1 kinase-mediated disease or disorder treated with these agents is macular degeneration.

In one embodiment of this invention, the at least one other therapeutically active agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. In another embodiment, the at least one other therapeutically active agent is selected from oseltamivir, zanamivir, rimantadine, or amantadine. In one embodiment, the RIP1 kinase-mediated disease or disorder treated with these agents is influenza.

In one embodiment of this invention, the at least one other therapeutically active agent is selected from a β-Lactam, nafcillin, sulfamethoxazolem, trimethoprim, sulfasalazine, acetyl sulfisoxazole, and vancomycin. In one embodiment, the RIP1 kinase-mediated disease or disorder treated with these agents is a staphylococcus infection.

In one embodiment of this invention, the at least one other therapeutically active agent is selected from a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb. In another embodiment, the at least one other therapeutically active agent is selected from muromonab-CD3, ASKP-1240, ASP015K, and TOL101. In one embodiment, the RIP1 kinase-mediated disease or disorder treated with these agents is transplant rejection.

In one embodiment of this invention, the at least one other therapeutically active agent is selected from a topical immunomodulator or calcineurin inhibitor, a topical corticosteroid, an oral corticosteroid, an interferon gamma, an antihistamine, or an antibiotic. In another embodiment, the at least one other therapeutically active agent is selected from pimecrolimus, tacrolimus, hydrocortizone, betamethasone, flurandrenolide, fluticasone, triamcinolone, fluocinonide, clobetasol, hydrocortisone, methylprednisolone, prednisolone, an interferon alpha protein, a recombinant synthetic type I interferon, interferon alpha-2a, interferon alpha-2b, hydroxyzine, diphenhydramine, flucloxacillin, dicloxacillin, and erythromycin. In one embodiment, the RIP1 kinase-mediated disease or disorder treated with these agents is atopic dermatitis.

Accordingly, one embodiment of this invention is directed to a method of inhibiting RIP1 kinase comprising contacting a cell with a compound of the invention. Another embodiment of this invention is a method of inhibiting RIP1 kinase comprising contacting a cell with a compound of Formula (I), or a salt, particularly a pharmaceutically acceptable salt, thereof. A particular embodiment of this invention is to a method of inhibiting RIP1 kinase comprising contacting a cell with a compound of Formula (I), or a salt, particularly a pharmaceutically acceptable salt, thereof.

In another embodiment, the invention is directed to a method of treating a RIP1 kinase-mediated disease or disorder (for example, a disease or disorder recited herein) comprising administering a therapeutically effective amount of a compound of Formula (I), or a salt, particularly a pharmaceutically acceptable salt thereof, to a human in need thereof. In a particular embodiment, the invention is directed to a method of treating a RIP1 kinase-mediated disease or disorder (for example, a disease or disorder recited herein) comprising administering a therapeutically effective amount of a compound described herein, or a salt, particularly a pharmaceutically acceptable salt thereof, to a human in need thereof.

This invention also provides a compound of Formula (I), or a pharmaceutically acceptable salt thereof, for use in therapy. This invention provides a compound of Formula (I), or a pharmaceutically acceptable salt thereof, for use in the treatment of a RIP1 kinase-mediated disease or disorder (for example, a disease or disorder recited herein). Specifically, this invention provides a compound described herein, or a pharmaceutically acceptable salt thereof, for use in therapy.

In another embodiment, this invention provides a compound of the invention for use in the treatment of a RIP1 kinase-mediated disease or disorder, specifically, a disease or disorder recited herein. This invention provides a compound described herein, or a pharmaceutically acceptable salt thereof, for use in the treatment of a RIP1 kinase-mediated disease or disorder, specifically, a disease or disorder recited herein.

This invention specifically provides for the use of a compound of Formula (I), or a pharmaceutically acceptable salt thereof, as an active therapeutic substance. More specifically, this provides for the use of the compounds described herein for the treatment of a RIP1 kinase-mediated disease or disorder, specifically, a disease or disorder recited herein. Accordingly, the invention provides for the use of a compound of Formula (I), as an active therapeutic substance in the treatment of a human in need thereof with a RIP1 kinase-mediated disease or disorder, specifically, a disease or disorder recited herein.

The invention further provides for the use of a compound of Formula (I), or a salt thereof, particularly a pharmaceutically acceptable salt thereof, in the manufacture of a medicament for use in the treatment of a RIP1 kinase-mediated disease or disorder, for example the diseases and disorders recited herein. Specifically, the invention also provides for the use of a compound described herein, or a pharmaceutically acceptable salt thereof, in the manufacture of a medicament for use in the treatment of a RIP1 kinase-mediated disease or disorder, for example the diseases and disorders recited herein.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate and/or inhibit the activity of RIP1 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a RIP1 kinase mediated disease or disorder, as described hereinabove.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients. The invention is directed to a pharmaceutical composition comprising a compound of Formula (I), or a pharmaceutically acceptable salt thereof, and one or more pharmaceutically acceptable excipients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. A dose of the pharmaceutical composition contains at least a therapeutically effective amount of a compound of this invention (i.e., a compound of Formula (I), or a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP1 kinase-mediated disease or disorder.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms suitable for use with the compounds of this invention include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company). Accordingly, another embodiment of this invention is a method of preparing a pharmaceutical composition comprising the step of admixing a compound of Formula (I), or a pharmaceutically acceptable salt, thereof, with one or more pharmaceutically acceptable excipients.

In one aspect, the invention is directed to a topical dosage form such as a cream, ointment, lotion, paste, or gel comprising an effective amount of a compound of the invention and one or more pharmaceutically acceptable excipients. Lipophilic formulations, such as anhydrous creams and ointments, generally will have a base derived from fatty alcohols, and polyethylene glycols. Additional additives include alcohols, non-ionic surfactants, and antioxidants. For ointments, the base normally will be an oil or mixture of oil and wax, e.g., petrolatum. Also, an antioxidant normally will be included in minor amounts. Because the compositions are applied topically and the effective dosage can be controlled by the total composition applied, the percentage of active ingredient in the composition can vary widely. Convenient concentrations range from 0.5% to 20%.

Topically applied gels can also be a foamable suspension gel comprising a compound of the invention, as an active agent, one or more thickening agents, and optionally, a dispersing/wetting agent, a pH-adjusting agent, a surfactant, a propellant, an antioxidant, an additional foaming agent, a chelating/sequestering agent, a solvent, a fragrance, a coloring agent, a preservative, wherein the gel is aqueous and forms a homogenous foam.

In one aspect, the invention is directed to a topical dosage form that can be administered by inhalation, that is, by intranasal and oral inhalation administration. Appropriate dosage forms for such administration, such as an aerosol formulation or a metered dose inhaler, may be prepared by conventional techniques. Intranasal sprays may be formulated with aqueous or non-aqueous vehicles with the addition of agents such as thickening agents, buffer salts or acid or alkali to adjust the pH, isotonicity adjusting agents or anti-oxidants. Solutions for inhalation by nebulization may be formulated with an aqueous vehicle with the addition of agents such as acid or alkali, buffer salts, isotonicity adjusting agents or antimicrobials.

Formulations for administration by inhalation or foamable gel often require the use of a suitable propellant. Capsules and cartridges of e.g. gelatin for use in an inhaler or insufflator may be formulated using a suitable powder base such as lactose or starch.

In another aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The compounds of this invention may be made by a variety of methods, including well-known standard synthetic methods. The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The reactions described herein are applicable for producing compounds of Formulas (I), (II), (III), (IV) and (V) having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, N Y, 1999.

Names for the intermediate and final compounds described herein were generated using the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com).

It will be appreciated by those skilled in the art that in certain instances these programs may name a structurally depicted compound as a tautomer of that compound. It is to be understood that any reference to a named compound or a structurally depicted compound is intended to encompass all tautomers of such compounds and any mixtures of tautomers thereof.

In the following examples and experimental descriptions, the following abbreviations may be used:

| Abbreviation | Meaning |
|---|---|
| aq. | aqueous |
| ACN | acetonitrile |
| Boc | tert-butoxycarbonyl |
| Cbz | benzyloxycarbonyl |
| CDI | 1,1'-carbonyldiimidazole |
| $CH_2Cl_2$ or DCM | methylene chloride |
| $CH_3CN$ or MeCN | acetonitrile |
| DCC | N,N'-dicyclohexylcarbodiimide |
| DIPEA | N',N'-diisopropylethylamine |
| DMAP | 4-dimethylaminopyidine |
| DMSO | dimethylsulfoxide |
| EtOAc | ethyl acetate |
| g | gram(s) |
| GCMS | gas chromatography-mass spectrometry |
| h, hr | hour(s) |
| HATU | O-(7-Azabenzotriazol-1yl)-N,N,N',N'-tetramethylyronium hexafluorophosphate |
| HPLC | high performance liquid chromatography |
| Hunig's Base or DIPEA | N',N'-diisopropylethylamine |
| i-$Pr_2$NEt | N',N'-diisopropylethylamine |
| KSCN | potassium thiocyanate |
| LCMS | liquid chromatography-mass spectroscopy |
| Me | methyl |
| MeOH or $CH_3OH$ | methanol |
| min | minute(s) |
| MS | mass spectrum |
| $PPh_3$ | triphenylphosine |
| Pd/C | palladium on carbon |
| rt | room temperature |
| TFA | trifluoroacetic acid |
| TFAA | trifluoroacetic anhydride |
| THF | tetrahydrofuran |
| TMSI | Iodotrimethylsilane |
| $T_3P$ | 2,4,6-tripropyl-1,3,5,2,4,6-trioxatriphosphinane 2,4,6-trioxide |
| Ts | p-toluenesulfonyl |
| TsCl | p-toluenesulfonyl chloride |
| wt. | weight |

$^1$H NMR spectra were recorded in either $CDCl_3$, DMSO-$d_6$, or DMSO-$d_6$, $D_2O$ exchange on either a Bruker DPX 400, Bruker Advance DRX, Varian Unity 400 spectrometer or JEOL Delta all working at 400 MHz. The internal standard used was either tetramethylsilane or the residual protonated solvent at 7.25 ppm for $CDCl_3$ or 2.50 ppm for DMSO-$d_6$. Chemical shifts are reported in parts per million (ppm). Abbreviations for NMR data are as follows: s=singlet, d=doublet, t=triplet, m=multiplet, br s=broad singlet, br d=broad doublet, br t=broad triplet, br m=broad multiplet, dd=doublet of doublets, dt=doublet of triplets, tt=triplet of triplets, ddd=doublet of doublet of doublets. J indicates the $^1$H NMR coupling constant measured in Hertz.

Mass spectrum was recorded on a Waters ZQ mass spectrometer using alternative-scan positive and negative mode electrospray ionisation. Cone voltage: 20 or 5V.

Scheme 1

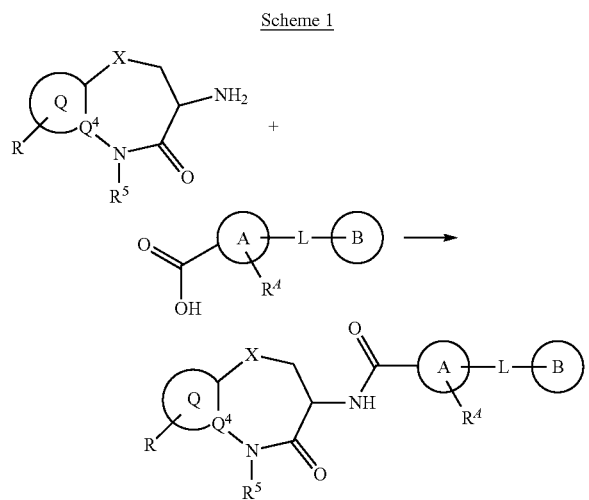

The compounds of this invention may be prepared using synthetic procedures illustrated in Scheme I and/or by drawing on the knowledge of a skilled organic chemist. The synthesis provided in this Scheme is applicable for producing compounds of the invention having a variety of different R/R$^4$ groups employing appropriate precursors, which are suitably protected if needed, to achieve compatibility with the reactions outlined herein. Subsequent deprotection, where needed, affords compounds of the nature generally disclosed. The Scheme provided is illustrative of processes that may be used to make the compounds of the invention. Azepine amines can be coupled to an appropriate acid using an amide coupling agent. Azepine amines suitable for use in this invention are commercially available, are known in the art (e.g., EP0599444 B1), or may be prepared by methods analogous to those known in the art (e.g. WO2014125444). Acids suitable for use in this invention are disclosed in WO2014125444, the disclosure of which is incorporated by reference herein.

Scheme 2

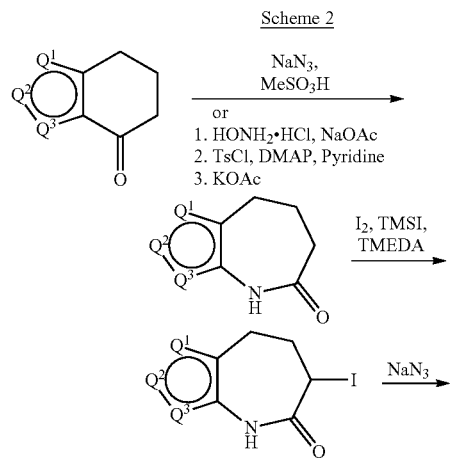

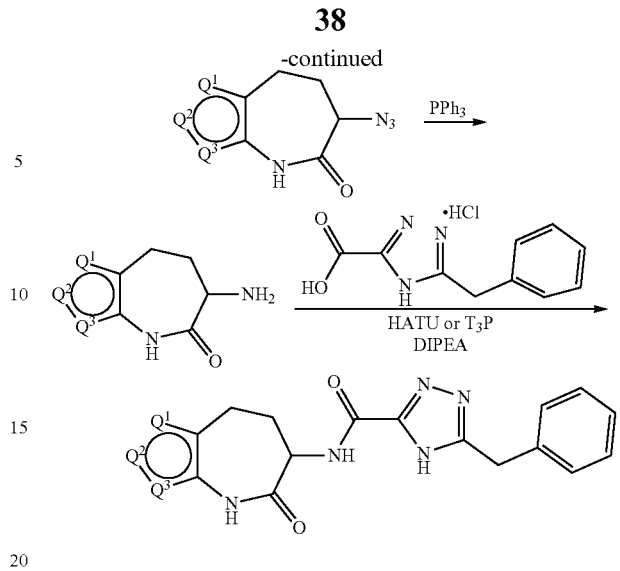

5-7 Membered heteroaryl carboxamides was prepared via the general method outlined in Scheme 2. The appropriately substituted 5-6 membered heteroaryl ketone was converted to a 5-7 membered heteroaryl amide via an acid-mediated Schmidt reaction with sodium azide or Beckmann rearrangement of the corresponding ketoximes formed from reaction with hydroxylamine. The 5-7 membered heteroaryl amide was converted to an α-iodolactam by iodotrimethylsilane-mediate iodination, subsequently converted to an α-azidolactam with sodium azide, and followed by the Staudinger reduction with triphenylphosphine to provide an α-aminolactam. This amine was coupled with an appropriate acid using an amide coupling agent, such as HATU or T$_3$P.

Alternatively, the amine was protected with a Boc protecting group, the lactam nitrogen was methylated with methyl iodide, and the amine was deprotected using acidic conditions. The resulting free amine was coupled with an appropriate acid using an amide coupling agent, such as HATU or T$_3$P.

Scheme 3

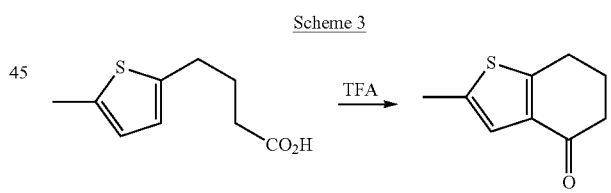

2-Methyl-6,7-dihydrobenzo[b]thiophen-4(5H)-one was prepared from the commercially available 4-(5-methylthiophen-2-yl)butanoic acid in trifluoroacetic acid (TFA) as shown in scheme 3. 2-Methyl-6,7-dihydrobenzo[b]thiophen-4(5H)-one was then used in the synthesis of the final heteroaryl carboxamide as shown in scheme 2.

Scheme 4

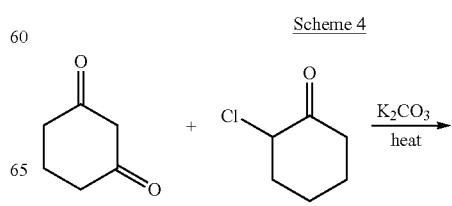

-continued

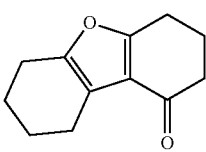

3,4,6,7,8,9-Hexahydrodibenzo[b,d]furan-1(2H)-one was prepared via the condensation reaction of cyclohexane-1,3-dione and 2-chlorocyclohexanone in the presence of K2CO₃ and heat, as shown in scheme 4. 3,4,6,7,8,9-Hexahydrodibenzo[b,d]furan-1(2H)-one was then used in the synthesis of the final heteroaryl carboxamid as shown in scheme 2.

(S)-5-Benzyl-N-(3,4-dimethyl-5-oxo-5,6,7,8-tetra hydro-4H-isothiazolo[4,5-b][1,4]diazepin-6-yl)-4H-1,2,4-triazole-3-carboxamide was prepared from the coupling reaction of (S)-6-amino-3,4-dimethyl-7,8-dihydro-4H-isothiazolo[4,5-b][1,4]diazepin-5(6H)-one hydrochloride and 5-benzyl-4H-1,2,4-triazole-3-carboxylic acid using HATU in the presence of DIPEA. (S)-6-Amino-3,4-dimethyl-7,8-dihydro-4H-isothiazolo[4,5-b][1,4]diazepin-5(6H)-one was prepared from the commercially available 5-bromo-3-methyl-4-nitroisothiazole and (S)-3-amino-2-((tert-butoxycarbonyl)amino)propanoic acid in 5 steps as shown in Scheme 5.

Scheme 5

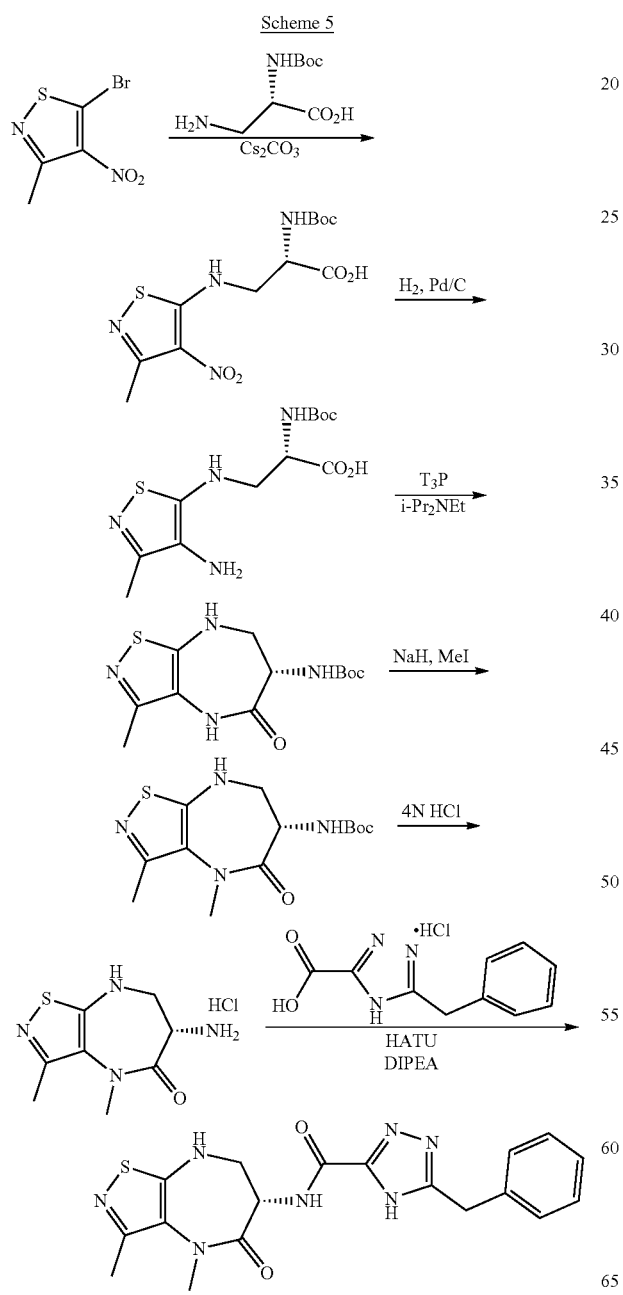

Scheme 6

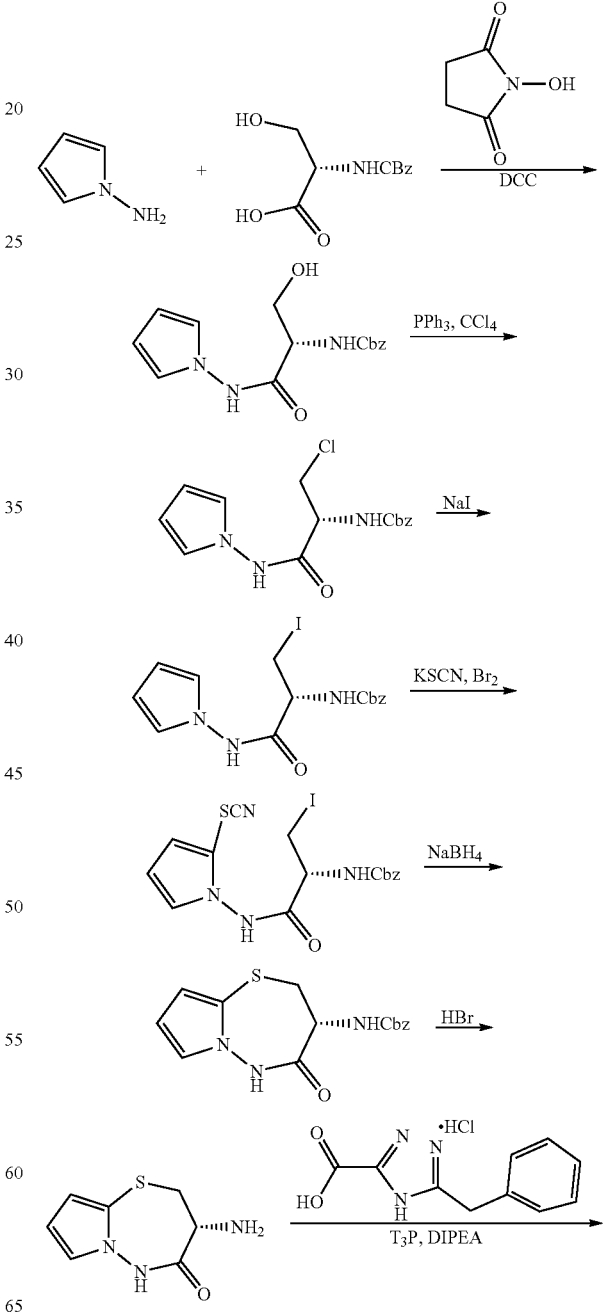

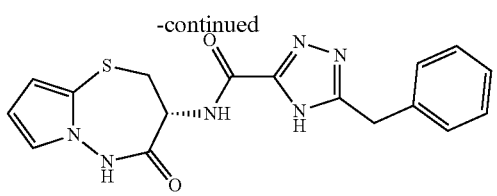

(R)-5-Benzyl-N-(4-oxo-2,3,4,5-tetrahydropyrrolo[2,1-b][1,3,4]thiadiazepin-3-yl)-4H-1,2,4-triazole-3-carboxamide was prepared from the coupling reaction of (R)-3-amino-2,3-dihydropyrrolo[2,1-b][1,3,4]thiadiazepin-4(5H)-one and 5-benzyl-4H-1,2,4-triazole-3-carboxylic acid using T$_3$P in the presence of DIPEA. (R)-3-Amino-2,3-dihydropyrrolo[2,1-b][1,3,4]thiadiazepin-4(5H)-one was prepared from the commercially available 1H-pyrrol-1-amine and (S)-2-(((benzyloxy)carbonyl)amino)-3-hydroxypropanoic acid in 6 steps as shown in scheme 6. Alternatively, the Cbz protected amine was methylated at the lactam nitrogen with methyl iodide, followed by deprotection of Cbz using acidic conditions. The resulting free amine was coupled with the appropriate acid using an amide coupling agent T$_3$P.

Preparation 1

6,8-Dimethyl-4,5-dihydro-1H-thieno[3,4-b]azepin-2(3H)-one

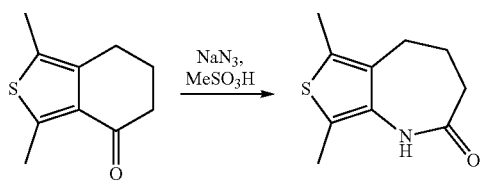

To a solution of 1,3-dimethyl-6,7-dihydrobenzo[c]thiophen-4(5H)-one (550 mg, 3.05 mmol) in methanesulfonic acid (5.5 ml, 85 mmol) at 0° C. (ice bath) was added sodium azide (218 mg, 3.36 mmol). The reaction mixture was stirred at 25° C. for 1 hr. The reaction mixture was poured in ice water (50 ml) and stirred for 30 min. The resultant solid was filtered, rinsed with water (100 ml), and dried under vacuum to afford 6,8-dimethyl-4,5-dihydro-1H-thieno[3,4-b]azepin-2(3H)-one (400 mg, 59.3% yield) as a white solid. $^1$H NMR (400 MHz, DMSO-d$_6$ δ: 1.86-1.94 (m, 2H), 2.04-2.12 (m, 2H), 2.17 (s, 3H), 2.24 (s, 3H), 2.43-2.48 (m, 2H), 9.16 (br s, 1H). MS (m/z) 195.9 [M+H]+.

Preparation 2

3-Iodo-6,8-dimethyl-4,5-dihydro-1H-thieno[3,4-b]azepin-2(3H)-one

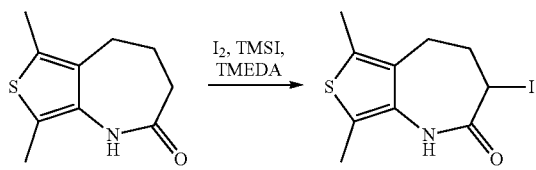

To a mixture of 6,8-dimethyl-4,5-dihydro-1H-thieno[3,4-b]azepin-2(3H)-one (400 mg, 2.05 mmol) in dichloromethane (10 mL) was added TMEDA (0.618 mL, 4.10 mmol) at 0° C. over a period of 10 min, followed by addition of TMSI (0.558 mL, 4.10 mmol). The mixture was stirred at 0° C. for 90 min then I2 (780 mg, 3.07 mmol) was added and stirred at 0° C.-25° C. for 3 hr. The reaction mixture was quenched with 5% aq. Na$_2$S$_2$O$_3$ (50 mL) and dichloromethane (150 mL) was added. The mixture was stirred for 15 min. The organic solution was separated and washed with water (2×100 mL) and brine, dried over sodium sulfate, filtered, and concentrated under reduced pressure to provide 3-iodo-6,8-dimethyl-4,5-dihydro-1H-thieno[3,4-b]azepin-2(3H)-one (600 mg, 80% yield) as a pale brown solid. $^1$H NMR (400 MHz, DMSO-d$_6$) δ: 2.20 (s, 3H), 2.26 (s, 3H), 2.39-2.48 (m, 3H), 2.57-2.65 (m, 1H), 4.55-4.64 (m, 1H), 9.59 (s, 1H). $^1$H NMR (400 MHz, DMSO-d$_6$, D$_2$O exchange) δ: 2.20 (s, 3H), 2.26 (s, 3H), 2.39-2.52 (m, 3H), 2.58-2.67 (m, 1H), 4.50-4.64 (m, 1H). MS (m/z) 321.9 [M+H]+.

The following intermediates, used in the preparation of titled example compounds, were synthesized using the method analogous to Preparation 1 and Preparation 2 described above.

| Structure | LCMS (m/z) [M + H]+ | Retention Time (min)[a] |
|---|---|---|
| 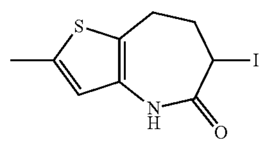 | 308.0 | 2.06 |
| 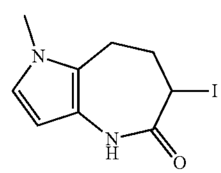 | 291.0 | 1.61 |
| 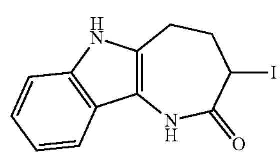 [SMILES: O=C1Nc2c([nH]c3ccccc23)CCC1I] | 327.0 | 2.18 |
| 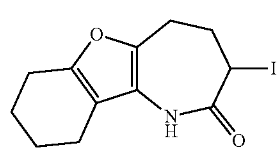 [SMILES: O=C1Nc2c(oc3c2CCCC3)CCC1I] | 332.1 | 2.65 |

[a]General condition for LCMS:

Acq. Method Conditions: RND-FA-4.5-MIN

Column: Acquity UPLC ® BEH C18 (50 mm × 2.1 mm, 1.7 um)

Mobile Phase: A: 0.1% Formic Acid in water; B: 0.1% Formic AcIin ACN

Time (min)/% B: 0/3, 0.4/3, 3.2/98, 3.8/98, 4.2/3, 4.5/3

Column Temp: 35° C., Flow Rate: 0.6 mL/min

Preparation 3

3-Azido-6,8-dimethyl-4,5-dihydro-1H-thieno[3,4-b]azepin-2(3H)-one

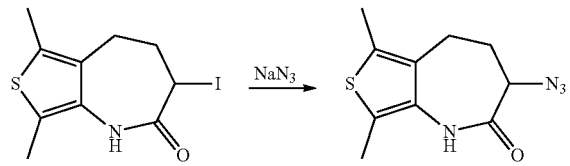 [SMILES: Cc1sc(C)c2c1CCC(I)C(=O)N2 ; Cc1sc(C)c2c1CCC(N=[N+]=[N-])C(=O)N2 ; "NaN3"]

To a stirred solution of 3-iodo-6,8-dimethyl-4,5-dihydro-1H-thieno[3,4-b]azepin-2(3H)-one (600 mg, 1.87 mmol) in DMF (10 mL) was added sodium azide (182 mg, 2.80 mmol). The mixture was stirred at 25° C. for 4 hr and was poured in water (20 ml). The resultant solid was filtered and rinsed with water (2×25 ml) and dried under vacuum to afford 3-azido-6,8-dimethyl-4,5-dihydro-1H-thieno[3,4-b]azepin-2(3H)-one (360 mg, 81% yield) as a white solid. $^1$H NMR (400 MHz, CDCl$_3$) δ: 2.29 (m, 8H), 2.45-2.61 (m, 1H), 2.73-2.86 (m, 1H), 3.87 (dd, J=11.18, 7.67 Hz, 1H), 7.11 (br s, 1H). MS (m/z) 237.1 [M+H]$^+$.

The following intermediates, used in the preparation of titled example compounds, were synthesized using the method analogous to Preparation 3 described above.

| Structure | LCMS (m/z) [M + H]$^+$ | Retention Time (min) |
|---|---|---|
| 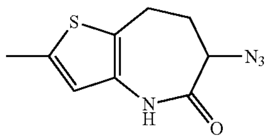 | 223.2 | 2.06[a] |
| 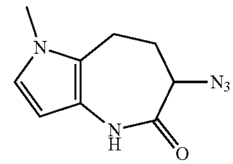 | 206.0 | 3.34[b] |
| 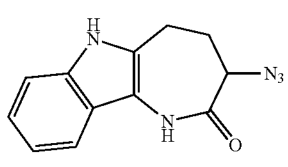 [SMILES: [N-]=[N+]=NC1CCc2[nH]c3ccccc3c2NC1=O] | 242.2 | 2.15[a] |
| 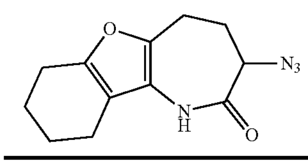 | 247.1 | 2.75[a] |

[a]General condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min
[b]Acq. Method Conditions: RND-ABC-6.5-MIN
column: XBridge BEH C18 (50 mm × 4.6 mm, 2.5 μm)
Mobile Phase: A: 5 mM Ammonium Bicarbonate in water (pH-10), I 100% ACN
Gradient: Time (min)/% B: 0/5, 0.5/5, 1.5/15, 3.3/98, 6.0/98, 6.1/5, 6.5/5
Column Temp: 35° C., Flow Rate: 1.3 mL/min

Preparation 4

3-Amino-6,8-dimethyl-4,5-dihydro-1H-thieno[3,4-b]azepin-2(3H)-one

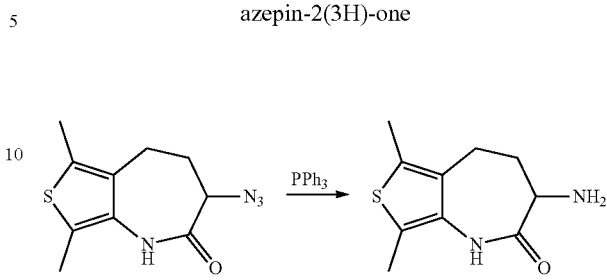

To a stirred solution of 3-azido-6,8-dimethyl-1H-thieno[3,4-b]azepin-2(3H)-one (360 mg, 1.52 mmol) in THF (10 mL) was added triphenylphosphine (599 mg, 2.285 mmol). The reaction mixture was stirred at 25° C. for 5 hr and was evaporated under reduced pressure. The residue was diluted with water (10 mL), acidified to pH=4 using 1N aq. HCl, and extracted with ethyl acetate (3×25 mL). The separated aqueous layer was basified with sodium carbonate (pH=10) and extracted with 10% MeOH in dichloromethane (3×50 mL). The combined organic solution was washed with brine (30 mL), dried over sodium sulfate, filtered, and concentrated under reduced pressure to afford 3-amino-6,8-dimethyl-4,5-dihydro-1H-thieno[3,4-b]azepin-2(3H)-one (178 mg, 54.4% yield) as a white solid. $^1$H NMR (400 MHz, DMSO-d$_6$) δ: 1.52-1.65 (m, 3H), 1.96-2.09 (m, 1H), 2.12-2.32 (m, 7H), 2.68 (dd, J=14.14, 6.69 Hz, 1H), 3.14 (dd, J=11.40, 7.23 Hz, 1H), 9.33 (s, 1H). $^1$H NMR (400 MHz, DMSO-d$_6$, D$_2$O exchange) δ: 1.61 (td, J=12.00, 7.34 Hz, 1H), 1.98-2.12 (m, 1H), 2.14-2.32 (m, 7H), 2.70 (dd, J=14.14, 6.69 Hz, 1H), 3.07-3.21 (m, 1H). MS (m/z) 211.1 [M+H]$^+$.

The following intermediates, used for the preparation of titled example compounds, were synthesized using the method analogous to Preparation 4 described above.

| Structure | LCMS (m/z) [M + H]$^+$ | Retention Time (min) |
|---|---|---|
| 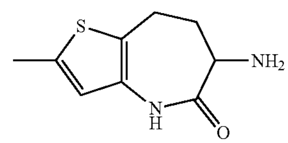 | 197.1 | 1.14[a] |
| 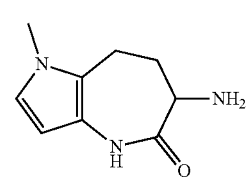 | 180.1 | 3.81[c] |
| 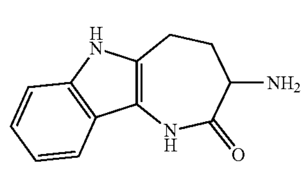 [SMILES: NC1CCc2[nH]c3ccccc3c2NC1=O] | 216.1 | 1.31[a] |

| Structure | LCMS (m/z) [M + H]+ | Retention Time (min) |
|---|---|---|
| (structure) | 221.2 | 2.21[a] |

[a]General condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min
[e]Method Conditions: RND-XBRIDGE-15-MIN-TFA-150
Column: Xbridge C18 (150 mm × 4.6 mm, 3.5 μm)
Mobile Phase: A: 0.05% TFA IIATER; B: ACN
Time (min)/% of ACN: 0/5, 0.5/5, 7/95, 14/95, 14.5/5, 15/5
Column temp: 35° C., Flow Rate = 1.0 mL/min.

Preparation 5

1-Methyl-6,7-dihydro-1H-indol-4(5H)-one oxime

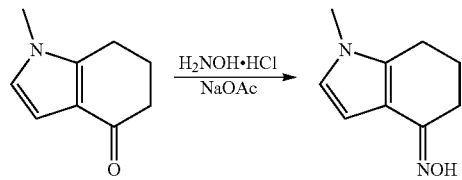

To a solution of 1-methyl-6,7-dihydro-1H-indol-4(5H)-one (7.2 g, 48.3 mmol) in ethanol (72 mL) and water (29 mL) were added sodium acetate (7.92 g, 97 mmol) and hydroxylamine hydrochloride (6.71 g, 97 mmol). The reaction mixture was stirred at 25° C. for 16 hr and was concentrated under reduced pressure. Additional water (30 ml) was added, and the mixture was stirred for 30 min. The resultant solid was collected by filtration and dried under reduced pressure to afford 1-methyl-6,7-dihydro-1H-indol-4(5H)-one oxime (as an E/Z mixture) (5.5 g, 66.6% yield) as a white solid. LCMS (m/z) 164.9 [M+H]+ (retention time: 1.10 and 1.23 min)[d].

The following intermediates, used for the preparation of titled example compounds, were synthesized using the method analogous to Preparation 5 described above.

| Structure | LCMS (m/z) [M + H]+ | Retention Time (min) |
|---|---|---|
| (structure) | 182.1 | 2.09[a] |
| (structure) | 201.2 | 1.63[a] |
| (structure) | 206.5 | 2.85[d] |

[a]General condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min
[d]Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 4/98,4.5/98, 5/3, 5.5/3
Column Temp: 35° C., Flow Rate: 0.45 mL/min Preparation 6

1-Methyl-6,7-dihydro-1H-indol-4(5H)-one O-tosyl oxime

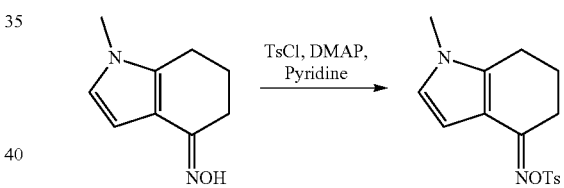

To a solution of 1-methyl-6,7-dihydro-1H-indol-4(5H)-one oxime (as a E/Z mixture of isomers) (5.5 g, 33.5 mmol) in pyridine (50 mL) was added DMAP (0.409 g, 3.35 mmol). Tosyl chloride (12.77 g, 67.0 mmol) was added portion-wise at 5 min intervals at 0° C. and the mixture was stirred at 25° C. for 16 hr. The reaction mixture was diluted with water (100 mL) and extracted with ethyl acetate (2×200 mL). The combined organic solution was washed with cold water (2×200 ml) and brine (100 mL). The organic solution was dried over sodium sulfate, filtered, and concentrated under reduced pressure. The crude compound was purified by normal phase column chromatography (silica gel: 60-120 mesh; eluent: 20% ethyl acetate in hexanes) to afford 1-methyl-6,7-dihydro-1H-indol-4(5H)-one O-tosyl oxime (4 g, 36.8% yield) as a pale brownish solid. $^1$H NMR (400 MHz, CDCl$_3$) δ: 1.87-1.97 (m, 2H), 2.42 (s, 3H), 2.56 (t, J=6.25 Hz, 2H), 2.67-2.76 (m, 2H), 3.48 (s, 3H), 6.33 (d, J=3.07 Hz, 1H), 6.47 (d, J=3.07 Hz, 1H), 7.30 (d, J=8.33 Hz, 2H), 7.90 (d, J=8.33 Hz, 2H). LCMS (m/z) 319.3 [M+H]+ (retention time: 2.45 min)[e].

The following intermediates, used for the preparation of titled example compounds, were synthesized using the method analogous to Preparation 6 described above.

| Structure | LCMS (m/z) [M + H]+ | Retention Time (min)e |
|---|---|---|
| (structure) | 336.1 | 2.79 |
| (structure) | 355.1 | 2.50 |
| (structure) | 360.2 | 3.40 | eGeneral condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min

| Structure | LCMS (m/z) [M + H]+ | Retention Time (min)g |
|---|---|---|
| (structure) | 182.0 | 3.23 |
| (structure) | 201.1 | 1.93 |
| (structure) | 206.2 | 1.96 | gGeneral condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min Preparation 7

1-Methyl-4,6,7,8-tetrahydropyrrolo[3,2-b]azepin-5(1H)-one

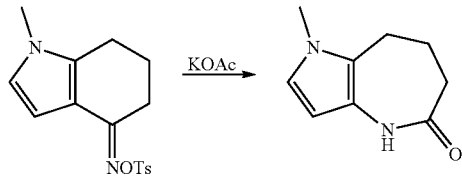

To a solution of 1-methyl-6,7-dihydro-1H-indol-4(5H)-one O-tosyl oxime (4 g, 12.56 mmol) in ethanol (136 mL) and water (272 mL) was added potassium acetate (1.233 g, 12.56 mmol). The reaction mixture was stirred at 100° C. for 3 hr and then was concentrated under reduced pressure. The resultant residue was diluted with water (20 ml) and extracted with ethyl acetate (2×50 ml). The combined organic solution was separated, dried over sodium sulfate, filtered, and concentrated under reduced pressure. The crude material was purified by normal phase column chromatography (silica gel: 60-120 mesh; eluent: 30% ethyl acetate in hexanes) to afford 1-methyl-4,6,7,8-tetrahydropyrrolo[3,2-b]azepin-5(1H)-one (2 g, 94% yield) as a pale yellow solid. 1H NMR (400 MHz, DMSO-$d_6$) δ: 1.84-1.98 (m, 2H), 2.30-2.42 (m, 2H), 2.70 (t, J=6.69 Hz, 2H), 3.40 (s, 3H), 5.63 (d, J=2.85 Hz, 1H), 6.51 (d, J=2.63 Hz, 1H), 9.02 (br s, 1H). LCMS (m/z) 165.0 [M+H]+ (retention time: 3.11 min).f f Method Conditions: RND-XBRIDGE-15-MIN-TFA-150 Column: Xbridge C18 (150 mm×4.6 mm, 3.5 μm) Mobile Phase: A: 0.05% TFA IN WATER; B: ACN Time (min)/% of ACN: 0/5, 0.5/5, 7/95, 14/95, 14.5/5, 15/5 Column temp: 35° C., Flow Rate=1.0 mL/min.

The following intermediates used for the preparation of titled example compounds were synthesized using the method analogous to Preparation 7 described above.

Preparation 8

2,6-Diiodo-1,3-dimethyl-4,6,7,8-tetrahydropyrrolo[3,2-b]azepin-5(1H)-one

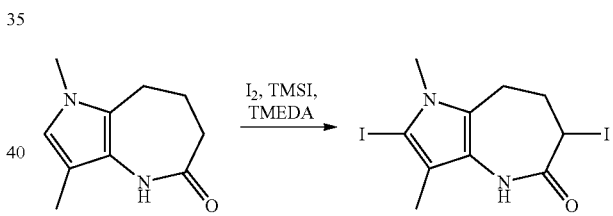

To a stirred solution of 1,3-dimethyl-4,6,7,8-tetrahydropyrrolo[3,2-b]azepin-5(1H)-one (350 mg, 1.94 mmol) in DCM (40.0 m')' as added N,N,N'N'-tetramethylethylenediamine (0.587 mL, 3.89 mmol). TMSI (0.529 mL, 3.89 mmol) was added dropwise at 0° C., and the resulting mixture was stirred for 90 min at 0° C. Iodine (740 mg, 2.92 mmol) was added to the reaction mixture at 0° C. The reaction mixture was stirred at 0° C. for 30 min and then stirred at 25° C. for 3 hr. The reaction mixture was partitioned between DCM (50 ml) and water (40 ml). The organic layer was separated, and the aqueous layer was extracted with DCM (2×30 ml). The combined organic solution was washed with brine (30 ml), dried over sodium sulfate, filtered, and concentrated under reduced pressure. The crude compound was purified by normal phase column chromatography (silica gel: 10 g of 100-200 mesh silica gel; eluent: a gradient of 5% ethyl acetate in hexanes to 10% ethyl acetate in hexanes) to afford 2,6-diiodo-1,3-dimethyl-4,6,7, 8-tetrahydropyrrolo[3,2-b]azepin-5(1H)-one (250 mg, 26.6% yield). 1H NMR (400 MHz, DMSO-$d_6$) δ: 1.76-1.84 (m, 1H), 1.90 (s, 3H), 2.10-2.21 (m, 1H), 2.77 (ddd, J=16.83, 11.13, 6.03 Hz, 1H), 3.01-3.10 (m, 1H), 3.40 (s, 3H), 4.81 (br d, J=7.67 Hz, 1H), 9.01 (s, 1H). MS (m/z) 430.9 [M+H]+.

Preparation 9

6-Azido-2-iodo-1,3-dimethyl-4,6,7,8-tetrahydropyrrolo[3,2-b]azepin-5(1H)-one

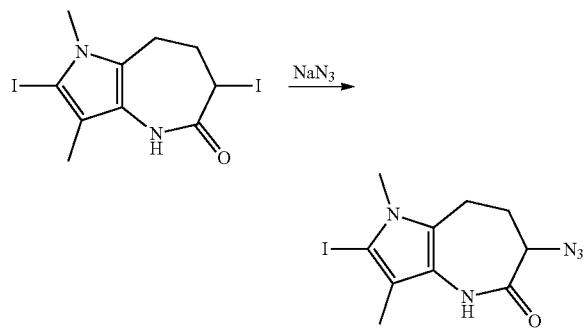

To a stirred solution of 2,6-diiodo-1,3-dimethyl-4,6,7,8-tetrahydropyrrolo[3,2-b]azepin-5(1H)-one (500.0 mg, 1.035 mmol) in DMF (10.0 mL) at 10° C. was added sodium azide (101 mg, 1.552 mmol). The reaction mixture was stirred at 25° C. for 2 hr. The reaction mixture was partitioned between ethyl acetate (100 ml) and cold water (50 ml). The organic layer was separated and washed with cold water (5×50 ml) and brine (50 ml), dried over sodium sulfate, filtered, and concentration under reduced pressure. The crude compound was purified by normal phase column chromatography (silica gel: 25 g of 100-200 mesh silica gel; eluent: a gradient of 100% hexanes to 5% ethyl acetate in hexanes) to afford 6-azido-2-iodo-1,3-dimethyl-4,6,7,8-tetrahydropyrrolo[3,2-b]azepin-5(1H)-one (160.0 mg, 40.8% yield) as a pale yellow solid. $^1$H NMR (400 MHz, DMSO-$d_6$) δ: 1.90 (s, 3H), 1.96-2.19 (m, 2H), 2.77-2.98 (m, 2H), 3.39 (s, 3H), 4.11 (dd, J=10.41, 2.30 Hz, 1H), 9.32 (s, 1H). MS (m/z) 346.0 [M+H]$^+$.

Preparation 10

6-Amino-1,3-dimethyl-4,6,7,8-tetrahydropyrrolo[3,2-b]azepin-5(1H)-one

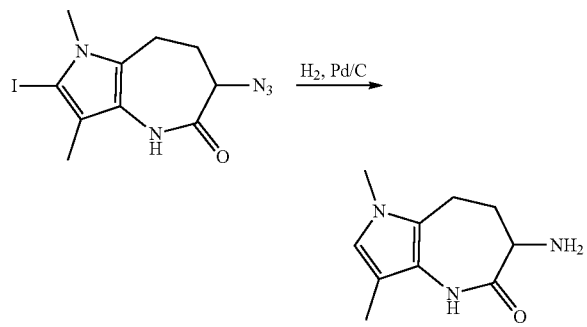

To a stirred solution of 6-azido-2-iodo-1,3-dimethyl-4,6,7,8-tetrahydropyrrolo[3,2-b]azepin-5(1H)-one (160 mg, 0.422 mmol) in methanol (10 mL) at rt was added 10% palladium on carbon (50% wet) (449 mg, 0.422 mmol). The reaction mixture was stirred for 4 hr under hydrogen atmosphere at rt. The reaction mixture was filtered over a celite bed and washed with ethanol (20 mL). The filtrate was concentrated under reduced pressure and purified by preparatory HPLC (eluent: 0.1% aqueous ammonium bicarbonate and acetonitrile) to afford 6-amino-1,3-dimethyl-4,6,7,8-tetrahydropyrrolo[3,2-b]azepin-5(1H)-one (19 mg, 22.30% yield) as a pale brown solid. $^1$H NMR (400 MHz, DMSO-$d_6$) δ: 1.75-1.84 (m, 1H), 1.87 (s, 3H), 1.93-2.07 (m, 1H), 2.58-2.86 (m, 4H), 3.26-3.36 (m, 4H), 6.33 (s, 1H), 8.81 (s, 1H). $^1$H NMR (400 MHz, DMSO-$d_6$, $D_2O$ exchange) δ: 1.77-1.84 (m, 1H), 1.87 (s, 3H), 1.98-2.05 (m, 1H), 2.65-2.77 (m, 2H), 3.26 (br d, J=8.55 Hz, 1H), 3.36 (s, 3H), 6.35 (s, 1H). MS (m/z) 194.2 [M+H]$^+$.

Preparation 11

(S)-2-((tert-Butoxycarbonyl)amino)-3-((3-methyl-4-nitroisothiazol-5-yl)amino)propanoic acid

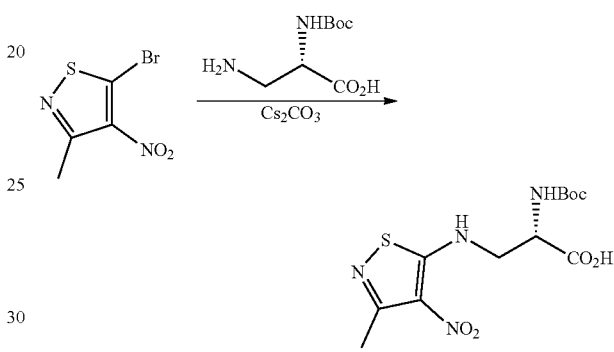

To a solution of commercially available 5-bromo-3-methyl-4-nitroisothiazole (2.8 g, 12.55 mmol) and (S)-3-amino-2-((tert-butoxycarbonyl)amino)propanoic acid (2.69 g, 13.18 mmol) in DMF (100 mL) was added $Cs_2CO_3$ (10.23 g, 31.4 mmol) at rt. The reaction mixture was stirred at 25° C. for 16 hr. Water (600 mL) was added to the reaction mixture. The reaction mixture was acidified with citric acid up to pH=4-5 and extracted with EtOAc (2×500 mL). The combined organic solution was washed with water (2×300 mL) and brine (300 mL), dried over sodium sulfate, filtered, and concentrated under reduced pressure to afford (S)-2-((tert-butoxycarbonyl)amino)-3-((3-methyl-4-nitroisothiazol-5-yl)amino)propanoic acid (4 g, 91% yield) as a pale yellow solid. $^1$H NMR (400 MHz, DMSO-$d_6$) δ: 1.36 (s, 9H), 2.51 (s, 3H), 3.44-3.59 (m, 1H), 3.68 (dt, J=13.81, 5.15 Hz, 1H), 4.18-4.38 (m, 1H), 7.37 (br d, J=7.89 Hz, 1H), 8.99 (br t, J=6.03 Hz, 1H), 12.95 (br s, 1H). $^1$H NMR (400 MHz, DMSO-$d_6$, $D_2O$ exchange) δ: 1.38 (s, 9H), 2.52 (s, 3H), 3.45-3.60 (m, 1H), 3.69 (dt, J=13.81, 5.15 Hz, 1H), 4.25-4.38 (m, 1H). MS (m/z) 347.2 [M+H]$^+$.

Preparation 12

(S)-3-((4-Amino-3-methylisothiazol-5-yl)amino)-2-((tertbutoxycarbonyl)amino)propanoic acid

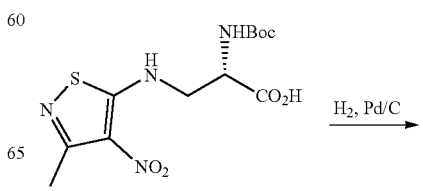

-continued

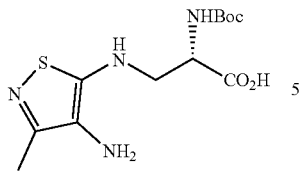

To (S)-2-((tert-butoxycarbonyl)amino)-3-((3-methyl-4-nitroisothiazol-5-yl)amino)propanoic acid (4 g, 11.55 mmol) in methanol (30 mL) was added and 10% palladium on carbon (18.44 g, 17.32 mmol). The reaction mixture was stirred under hydrogen pressure (80 psi) at rt for 48 hr. The reaction mixture was filtered over celite and washed with methanol (100 mL). The filtrate was concentrated under reduced pressure to afford crude (S)-3-((4-amino-3-methyl-isothiazol-5-yl)amino)-2-((tert-butoxycarbonyl)amino)propanoic acid (3.2 g, 20.76% yield) as a brown semi solid which was used in the next reaction without further purification. MS (m/z) 317.1 [M+H]$^+$.

Preparation 13

((S)-tert-Butyl (3-methyl-5-oxo-5,6,7,8-tetrahydro-4H-isothiazolo[4,5-b][1,4]diazepin-6-yl)carbamate

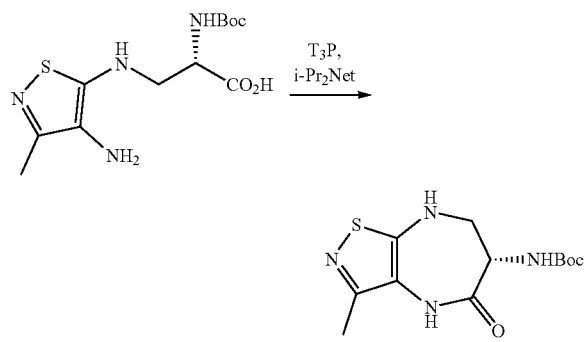

To a stirred suspension of (S)-3-((4-amino-3-methylisothiazol-5-yl)amino)-2-((tert-butoxycarbonyl)amino)propanoic acid (3.2 g, 2.397 mmol) and DIPEA (2.093 mL, 11.99 mmol) in dichloromethane (120 mL) under nitrogen at 20° C. was added a solution of T$_3$P (2.14 mL, 3.60 mmol) in ethyl acetate dropwise. The reaction mixture was stirred at 0-25° C. for 16 hr. The reaction was quenched with water (250 mL) and extracted with dichloromethane (300 mL). The organic solution was washed with brine (200 mL) and dried over sodium sulfate, filtered, and concentrated under reduced pressure. The resultant residue was purified by normal phase column chromatography (silica gel: 100-200 mesh; eluent: a gradient of 5% EtOAc in hexanes to 50% EtOAc in hexanes) to afford (S)-tert-butyl (3-methyl-5-oxo-5,6,7,8-tetrahydro-4H-isothiazolo[4,5-b][1,4]diazepin-6-yl)carbamate (640 mg, 89% yield) as an off-white solid. $^1$H NMR (400 MHz, DMSO-d$_6$) δ: 1.38 (s, 9H), 2.18 (s, 3H), 3.25-3.32 (m, 1H), 3.41-3.57 (m, 1 H), 4.04-4.27 (m, 1H), 6.80 (br d, J=7.45 Hz, 1H), 7.41 (br d, J=4.82 Hz, 1H), 9.57 (s, 1H). MS (m/z) 299.1 [M+H]$^+$.

Preparation 14

(S)-tert-Butyl (3,4-dimethyl-5-oxo-5,6,7,8-tetrahydro-4H-isothiazolo[4,5-b][1,4]diazepin-6-yl)carbamate

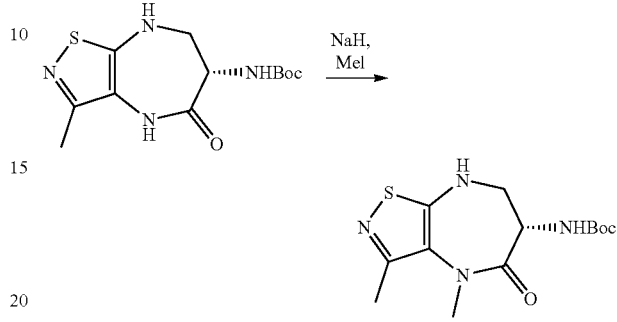

To a stirred solution of (S)-tert-butyl(3-methyl-5-oxo-5,6,7,8-tetrahydro-4H-isothiazolo[4,5-b][1,4]diazepin-6-yl) carbamate (1 g, 3.35 mmol) in THF (25 mL) were added sodium hydride (60% in mineral oil) (0.147 g, 3.69 mmol) and methyl iodide (0.231 mL, 3.69 mmol) at 0° C. The reaction mixture was stirred for 5 hr at 25° C., was poured into water (50 mL), and extracted with ethyl acetate (2×50 mL). The combined organic solution was dried over sodium sulfate, filtered, and concentrated under reduced pressure. The resultant residue was purified by normal phase column chromatography (silica gel: 100-200 mesh; eluent: a gradient of 5% EtOAc in hexanes to 40% EtOAc in hexanes) to afford (S)-tert-butyl (3,4-dimethyl-5-oxo-5,6,7,8-tetrahydro-4H-isothiazolo[4,5-b][1,4]diazepin-6-yl)carbamate (530 mg, 46.6% yield) as a pale yellow solid. $^1$H NMR (400 MHz, DMSO-d$_6$) δ: 1.29-1.41 (m, 9H), 2.27 (s, 3H), 3.12 (s, 3H), 3.36-3.40 (m, 1H), 3.44-3.59 (m, 1H), 4.25-4.40 (m, 1H), 6.90 (br d, J=7.67 Hz, 1H), 7.07 (br d, J=6.14 Hz, 1H). MS (m/z) 313.2 [M+H]$^+$.

Preparation 15

(S)-6-Amino-3,4-dimethyl-7,8-dihydro-4H-isothiazolo[4,5-b][1,4]diazepin-5(6H)-one hydrochloride salt

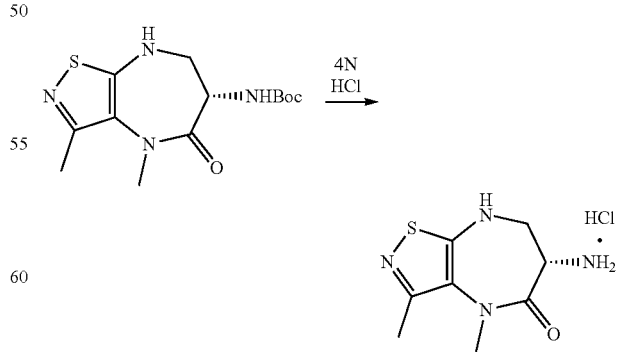

To a stirred solution of (S)-tert-butyl (3,4-dimethyl-5-oxo-5,6,7,8-tetrahydro-4H-isothiazolo[4,5-b][1,4]diazepin-6-yl)carbamate (520 mg, 1.665 mmol) in dichloromethane (10 mL) was added 4M HCl in 1,4-dioxane (2.081 mL, 8.32 mmol) at 0° C. The reaction mixture was stirred at 0-25° C. for 5 hr. The reaction mixture was concentrated under reduced pressure. The resultant solid was triturated with diethyl ether (2×50 ml) and pentane (50 ml) and dried under reduced pressure for 1 hr to afford (S)-6-amino-3,4-dimethyl-7,8-dihydro-4H-isothiazolo[4,5-b][1,4]diazepin-5(6H)-one, hydrochloride (360 mg, 71.8% yield) as a brown solid. $^1$H NMR (400 MHz, DMSO-d$_6$) δ: 2.27 (s, 3H), 3.19 (s, 3H), 3.48 (t, J=11.07 Hz, 1H), 3.79-3.92 (m, 1H), 4.19-4.37 (m, 1H), 7.57 (br s, 1H), 8.56 (br s, 3H). $^1$H NMR (400 MHz, DMSO-d$_6$, D$_2$O ex) δ: 2.29 (s, 3H), 3.20 (s, 3H), 3.51 (t, J=11.07 Hz, 1H), 3.80 (dd, J=11.29, 3.62 Hz, 1H), 4.31 (dd, J=10.96, 3.51 Hz, 1H). MS (m/z) 213.1 [M+H]$^+$.

Preparation 16

2-Methyl-6,7-dihydrobenzo[b]thiophen-4(5H)-one

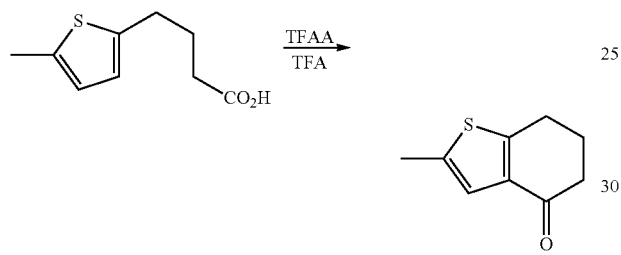

To a stirred solution of 4-(5-methylthiophen-2-yl)butanoic acid (9.5 g, 51.6 mmol) in TFA (210.0 mL) at 0° C. was added TFAA (13.11 mL, 93 mmol). The reaction mixture was stirred for 16 h at rt. The reaction mixture was quenched with ice, slowly basified with solid sodium bicarbonate (40 g), and extracted with DCM (2×500 ml). The combined organic solution was washed with water (2×250 ml) and brine (250 mL), dried over sodium sulfate, filtered, and concentrated under reduced pressure to afford crude 2-methyl-6,7-dihydrobenzo[b]thiophen-4(5H)-one (8 g, 90% yield) as reddish liquid, which was used in the next reaction without further purification. MS (m/z) 167.1 [M+H]$^+$.

Preparation 17

(S)-Benzyl (1-((1H-pyrrol-1-yl)amino)-3-hydroxy-1-oxopropan-2-yl)carbamate

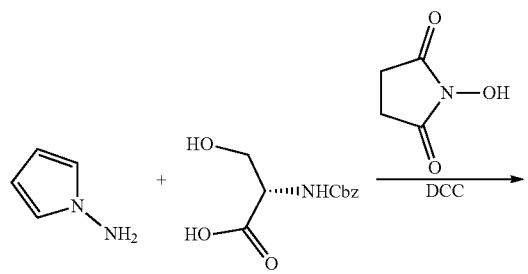

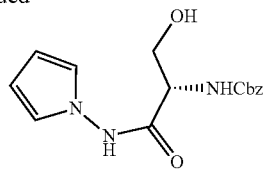

To a solution of (S)-2-(((benzyloxy)carbonyl)amino)-3-hydroxypropanoic acid (15 g, 62.7 mmol) and 1-hydroxypyrrolidine-2,5-dione (7.50 g, 65.2 mmol) in anhydrous THF (90 mL) was added a solution of DCC (12.94 g, 62.7 mmol) in anhydrous tetrahydrofuran (THF) (90 mL) at 0° C. dropwise over 5 min. The reaction mixture was stirred for 2 h at 0° C. and an additional 1 h at room temperature. The resulting precipitate was removed by filtration. A solution of 1H-pyrrol-1-amine (5.15 g, 62.7 mmol) in THF (20 mL) was added, and the mixture was stirred for 12 hr. The solvent was evaporated under reduced pressure, and the residue was dissolved in refluxing EtOAc (10 mL) and filtered immediately. The filtrate was cooled to 25° C., and the resulting solids were collected by filtration, washed with a minimum amount of EtOAc (5 mL) and pentane (100 mL), and dried under vacuum for 12 hr to afford (S)-benzyl (1-((1H-pyrrol-1-yl)amino)-3-hydroxy-1-oxopropan-2-yl)carbamate (11 g, 57.8% yield) as a white solid. LCMS (m/z) 304.2 [M+H]$^+$.

Preparation 18

(R)-Benzyl (1-((1H-pyrrol-1-yl)amino)-3-chloro-1-oxopropan-2-yl)carbamate

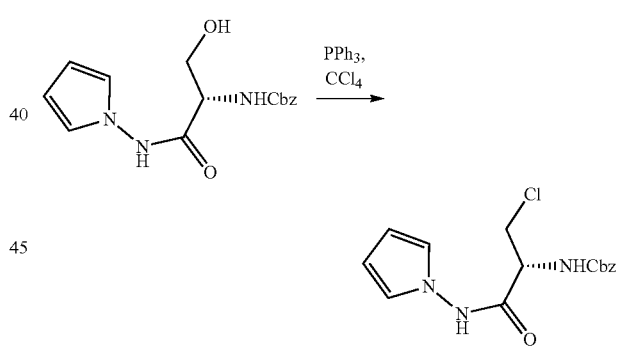

To a stirred solution of (S)-benzyl (1-((1H-pyrrol-1-yl)amino)-3-hydroxy-1-oxopropan-2-yl)carbamate (11 g, 30.1 mmol) in carbon tetrachloride (110 mL) and DMF (78 mL) was added triphenylphosphine (7.90 g, 30.1 mmol) at 25° C. under argon. The reaction mixture was stirred for 3 hr. The reaction mixture was diluted with water (50 mL) and extracted with EtOAc (2×50 mL). The combined organic solution was washed with brine (50 mL), dried over anhydrous sodium sulfate, filtered, and then concentrated under reduced pressure. The crude product was purified by normal phase column chromatography (silica gel: 100 g 100-200 mesh silica gel; eluent: 5-10% EtOAc in hexanes (500 mL) to remove non-polar impurities, and then 20-25% EtOAc in hexanes (2×500 mL))l to provide (R)-benzyl (1-((1H-pyrrol-1-yl)amino)-3-chloro-1-oxopropan-2-yl)carbamate (4.5 g, 45.7% yield) as a white solid. MS (m/z)=322.2 and 324.2 [M+H]$^+$

Preparation 19

(R)-Benzyl (1-((1H-pyrrol-1-yl)amino)-3-iodo-1-oxopropan-2-yl)carbamate

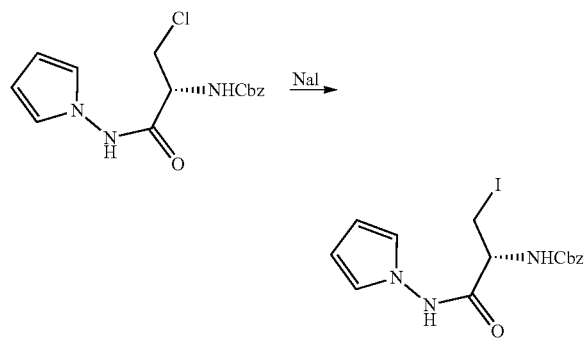

A mixture of (R)-benzyl (1-((1H-pyrrol-1-yl)amino)-3-chloro-1-oxopropan-2-yl)carbamate (4.5 g, 13.75 mmol) and sodium iodide (11.54 g, 77 mmol) in acetone (140 mL) was heated to reflux at 60° C. for 48 hr. The reaction mixture was concentrated to half of the initial volume (75 mL), and water (150 mL) was cautiously added. The resulting precipitate was collected by filtration, washed with 1:2 acetone-water (10-15 mL), and dried under vacuum for 12 hr to afford (R)-benzyl (1-((1H-pyrrol-1-yl)amino)-3-iodo-1-oxopropan-2-yl)carbamate (3.5 g, 51.8% yield). LCMS (m/z) 414.09 [M+H]$^+$

Preparation 20

(R)-Benzyl (3-iodo-1-oxo-1-((2-thiocyanato-1H-pyrrol-1-yl)amino)propa n-2-yl)carbamate

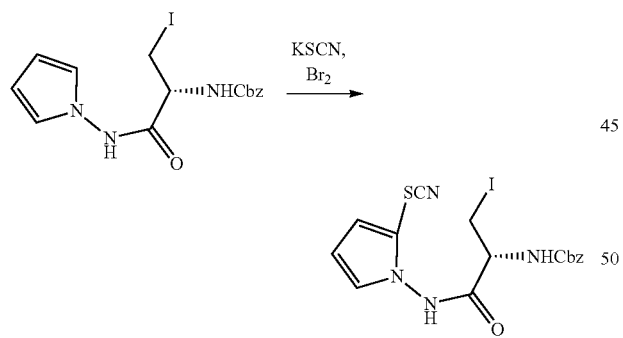

To a suspension of potassium thiocyanate (400 mg, 4.12 mmol) in methanol (2 mL) at −78° C. under nitrogen was added a solution of bromine (0.094 mL, 1.830 mmol) in methanol (2 mL) dropwise. The mixture was stirred at −78° C. for 15 min A solution of (R)-benzyl (1-((1H-pyrrol-1-yl)amino)-3-iodo-1-oxopropan-2-yl)carbamate (900 mg, 1.830 mmol) in methanol (10 mL) was added at −78° C. The reaction mixture was stirred at −78° C. for 2 hr. The reaction mixture was poured into cold water (25 mL) and extracted with DCM (2×75 mL). The combined organic extracts were washed with brine (25 mL), dried over anhydrous sodium sulfate, filtered, and then concentrated under reduced pressure. The crude product was purified by normal phase column chromatography (silica gel: 8 g of 100-200 mesh silica gel; eluent: 5-10% EtOAc in hexanes (200 mL) to remove non-polar impurities, and then 20% EtOAc in hexaneI400 mL)) to afford (R)-benzyl (3-iodo-1-oxo-1-((2-thiocyanato-1H-pyrrol-1-yl)amino)propan-2-yl)carbamate (600 mg, 50.9% yield) as a pale yellow solid. LCMS (m/z) 468.9 (ES$^-$)

Preparation 21

(R)-Benzyl (4-oxo-2,3,4,5-tetrahydropyrrolo[2,1-b][1,3,4]thiadiazepin-3-yl)carbamate

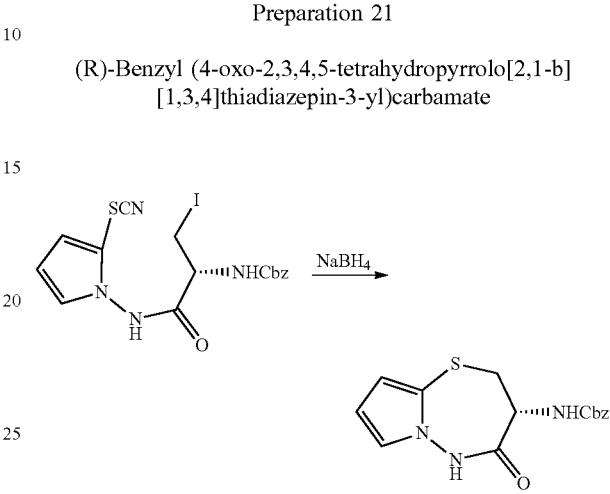

To a stirred solution of (R)-benzyl (3-iodo-1-oxo-1-((2-thiocyanato-1H-pyrrol-1-yl)amino)propan-2-yl)carbamate (600 mg, 0.944 mmol) in ethanol (50 mL) was added NaBH$_4$ (89 mg, 2.360 mmol) at −10° C. under argon. The reaction mixture was allowed to warm to room temperature (25° C.) and stirred for 2 hr. The reaction mixture was poured into water (5 mL) and acidified to pH 5-6 with 1N aq. HCl (~1 mL), and extracted with DCM (2×50 mL). The organic layer was washed with brine (10 mL), dried over anhydrous sodium sulfate, filtered, and then concentrated under reduced pressure. The crude product was purified by normal phase column chromatography (silica gel: 5 g of 100-200 mesh silica gel; eluent: a gradient of 5-10% EtOAc in hexanes (100 mL) to remove non-polar impurities, and then of 20% EtOAc in hInes (300 mL) to afford (R)-benzyl (4-oxo-2,3,4,5-tetrahydropyrrolo[2,1-b][1,3,4]thiadiazepin-3-yl)carbamate (180 mg, 59.2% yield) as a white solid. LCMS (m/z) 318.17 [M+H]$^+$.

Preparation 22

(R)-Benzyl (5-methyl-4-oxo-2,3,4,5-tetrahydropyrrolo[2,1-b][1,3,4]thiadiazepin-3-yl)carbamate

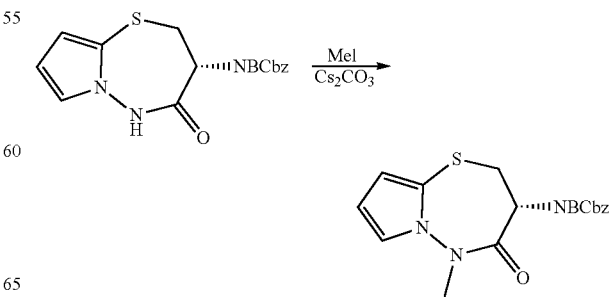

To a solution of (R)-benzyl (4-oxo-2,3,4,5-tetrahydropyrrolo[2,1-b][1,3,4]thiadiazepin-3-yl)carbamate (160 mg, 0.489 mmol) in DMF (6 mL) was added cesium carbonate (319 mg, 0.978 mmol) under nitrogen at 0° C. After 15 min, iodomethane (0.034 mL, 0.538 mmol) was added at 0° C. The reaction mixture was stirred at 0° C. for 1 hr, diluted with cold water (10 mL), and extracted with EtOAc (2×25 mL). The combined organic extracts were washed with brine (10 mL), dried over anhydrous sodium sulfate, filtered, and then concentrated under reduced pressure. The resultant residue was purified by normal phase column chromatography (silica gel: 2 g of 100-200 mesh silica gel; eluent: a gradient of 5-10% EtOAc in hexanes (100 mL) to removed non-polar impurities, and then 15% EtOAc in hexanes (2×100 mL) to afford (R)-benzyl (5-methyl-4-oxo-2,3,4,5-tetrahydropyrrolo [2,1-b][1,3,4]thiadiazepin-3-yl)carbamate (160 mg, 99% yield) as a thick brownish oil. LCMS (m/z) 332.0 [M+H]$^+$.

Preparation 23

(R)-3-Amino-2,3-dihydropyrrolo[2,1-b][1,3,4]thiadiazepin-4(5H)-one

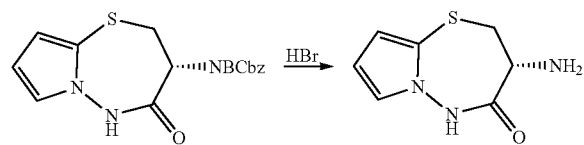

A mixture of (R)-benzyl (4-oxo-2,3,4,5-tetrahydropyrrolo [2,1-b][1,3,4]thiadiazepin-3-yl)carbamate (160 mg, 0.494 mmol) and HBr (33 wt. % in AcOH, 4 mL, 24.31 mmol) was stirred at 25° C. for 16 hr under argon. The solvent was evaporated under reduced pressure. The reaction mixture was basified with aqueous saturated NaHCO$_3$ solution (~5 mL) and extracted with EtOAc (2×100 mL). The combined organic extracts were washed with brine (10 mL), dried over anhydrous sodium sulfate, filtered, and then concentrated under reduced pressure. The crude product was purified by preparatory HPLC (eluent: a gradient of 5-98% of acetonitrile in 0.1% ammonium bicarbonate in water to afford (R)-3-amino-2,3-dihydropyrrolo[2,1-b][1,3,4]thiadiazepin-4(5H)-one (18 mg, 0.095 mmol, 19.29% yield) as a white solid. $^1$H NMR (400 MHz, DMSO-d$_6$) δ: 2.01 (br s, 2H), 2.54 (m, 1H), 3.02 (dd, J=11.18, 6.80 Hz, 1H), 3.26 (m, 1H), 6.12 (dd, J=3.95, 3.07 Hz, 1H), 6.32 (dd, J=3.95, 1.75 Hz, 1H), 7.09 (dd, J=3.07, 1.75 Hz, 1H), 11.03 (br s, 1H). LCMS (m/z) 184.2 [M+H]$^+$ The following intermediate, used for the preparation of the titled example compound, was synthesized from the product of Preparation 22 using the method analogous to Preparation 23 described above.

| Structure | LCMS (m/z) [M + H]$^+$ | Retention Time (min)$^h$ |
|---|---|---|
| 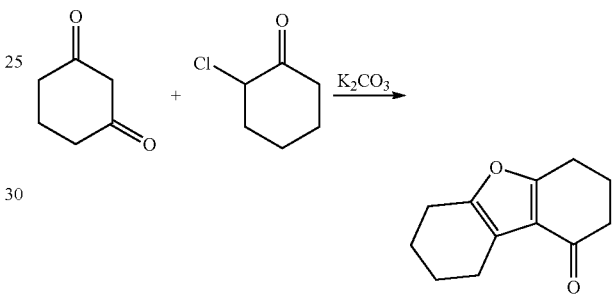 | 198.1 | 1.08 |

$^h$General condition for LCMS:
Acq. Method Conditions: RND-FA-4.5-MIN
Column: Acquity UPLC ® BEH C18 (50 mm × 2.1 mm, 1.7 um)
Mobile Phase: A: 0.1% Formic Acid in water; B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min Preparation 24

3,4,6,7,8,9-Hexahydrodibenzo[b,d]furan-1(2H)-one

To a solution of cyclohexane-1,3-dione (5 g, 44.6 mmol) in acetone (10 mL) in a sealed tube were added 2-chlorocyclohexanone (1.1 g, 8.30 mmol) and K2CO$_3$ (132 mg, 0.955 mmol). The reaction mixture was stirred at 150° C. for 5 hr. The reaction mixture was acidified with 6N HCl (~25 mL) and extracted with EtOAc (2×100 mL). The combined organic solution was washed with water (50 mL), dried over Na$_2$SO$_4$, filtered, and concentrated under reduced pressure. The crude compound was pre-adsorbed with silica gel (5 g) and purified by normal phase column chromatography (silica gel: 50 g 100-200 mesh silica gel; eluent: 10% ethyl acetate in hexanes (300 mL) to remove non-polar impurities and then with 15% EtOAc in hexanes (500 mL)) to afford 3,4,6,7,8,9-hexahydrodibenzo[b,d]furan-1(2H)-one (2.5 g, 28.9% yield) as an off-white solid. LCMS (m/z) 191.2 [M+H]$^+$.

Preparation 25

1-(2-Bromoethyl)-2-nitrobenzene

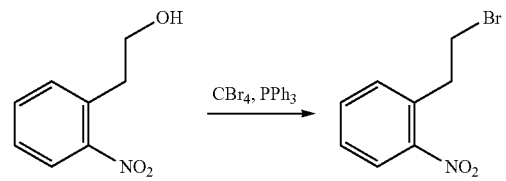 [SMILES: O=[N+]([O-])c1ccccc1CCO ; O=[N+]([O-])c1ccccc1CCBr]

To a stirred solution of triphenylphosphine (9.41 g, 35.9 mmol) in dichloromethane (50 mL) was added commercially available 2-(2-nitrophenyl)ethanol (5 g, 29.9 mmol) under nitrogen and a solution of carbon tetrabromide (11.90 g, 35.9 mmol) in dichloromethane (20 mL). The resulting mixture was stirred at 25° C. for 6 hr. The reaction was quenched with water (50 mL) and extracted with dichloromethane (2×100 ml). The combined organic extracts were washed with brine, dried over $Na_2SO_4$, filtered, and concentrated under reduced pressure. The resultant residue was purified by normal phase column chromatography (silica gel; eluent: 5% EtOAc in hexanes (300 mL) to remove non-polar impurities, and then 10% EtOAc in hexanes (800 mL)) to afford 1-(2-bromoethyl)-2-nitrobenzene (5 g, 67.1% yield) as a pale yellow liquid. GCMS (m/z)=229.0 & 230.9 (retention time: 6.42 min) (Column: ZB-5MS (30 m×0.32 mm×1 μm), He=2.0 mL/min, Inj=230° C., Split=50:1, I.V=1.0 μL, Programme: 100° C./1 min, 20° C./1 min, 310° C./5.5 min, Solvent delay: 2.5 min, MSD Scan range: 50-900).

Preparation 26 tert-Butyl 2-(2-nitrophenethyl)hydrazinecarboxylate

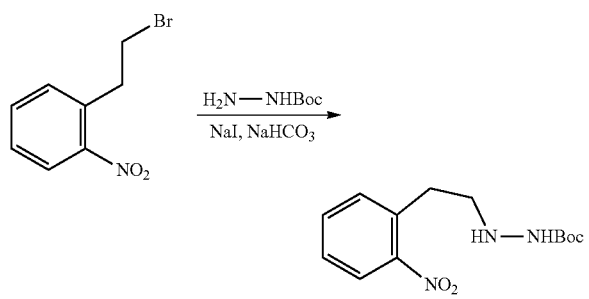

To a stirred solution of 1-(2-bromoethyl)-2-nitrobenzene (3 g, 11.74 mmol) in acetonitrile (60 mL) were added tert-butyl hydrazinecarboxylate (2.327 g, 17.60 mmol), sodium bicarbonate (1.972 g, 23.47 mmol), and sodium iodide (0.176 g, 1.174 mmol). The reaction mixture was stirred at 90° C. for 18 hr. The reaction mixture was concentrated under reduced pressure, quenched with water, and extracted with EtOAc (2×130 mL). The combined organic extracts were washed with water (80 mL), dried over $Na_2SO_4$, filtered, and concentrated under reduced pressure. The resultant residue was purified by normal phase column chromatography (silica gel: 100-200 mesh; eluent: 10% ethyl acetate in hexanes (700 mL) to remove non-polar impurities, and then 40% ethyl acetate in hexanes (1000 mL)) to afford tert-butyl 2-(2-nitrophenethyl)hydrazinecarboxylate (1.6 g, 42.7% yield) as a pale yellow liquid. MS (m/z) 282.3 $[M+H]^+$.

Preparation 27 tert-Butyl 2-(2-aminophenethyl)hydrazinecarboxylate

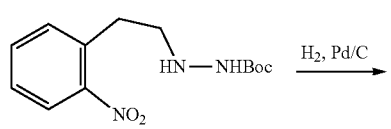

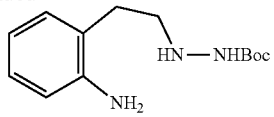

A stirred solution of tert-butyl 2-(2-nitrophenethyl)hydrazinecarboxylate (1.6 g, 5.01 mmol) and 10% Pd/C (1.066 g, 1.001 mmol) in ethanol (20 mL) was hydrogenated (40 psi) at 25° C. for 18 hr. The reaction mixture was filtered over celite and washed with ethanol (2×50 mL). The filtrate was concentrated under reduced pressure. The resultant residue was triturated with n-pentane (2×20 mL) and dried under reduced pressure to afford tert-butyl 2-(2-aminophenethyl)hydrazinecarboxylate (700 mg, 48.8% yield) as a grey colored solid. MS (m/z) 252.3 $[M+H]^+$.

Preparation 28 tert-Butyl (2-oxo-4,5-dihydro-1H-benzo[d][1,3]diazepin-3(2H)-yl)carbamate

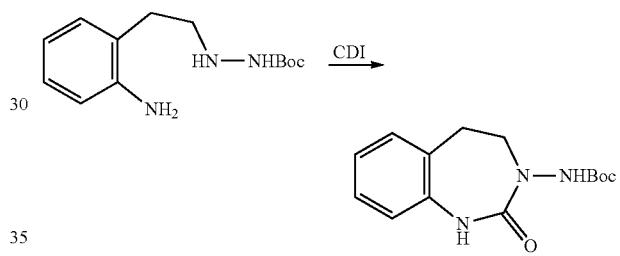

To a stirred solution of tert-butyl 2-(2-aminophenethyl)hydrazinecarboxylate (50 mg, 0.199 mmol) in THF (5 mL) was added CDI (48.4 mg, 0.298 mmol). The reaction mixture was stirred at 25° C. for 18 hr, diluted with water (25 mL), and extracted with ethyl acetate (2×45 mL). The combined organic extracts were washed with water (25 mL) and brine (20 mL), T dried over $Na_2SO_4$, filtered, and concentrated under reduced pressure. The resultant residue was purified by normal phase column chromatography (silica gel: 6 g of 100-200 mesh silica gel; eluent: a gradient of 10-20% ethyl acetate in hexanes (150 mL) to remove non-polar impurities, and then 40% ethyl acetate in hexanes (350 mL)) to afford tert-butyl (2-oxo-4,5-dihydro-1H-benzo[d][1,3]diazepin-3(2H)-yl)carbamate (230 mg, 46.7% yield) as a white solid. MS (m/z) 278.2 $[M+H]^+$.

Preparation 29

3-Amino-4,5-dihydro-1H-benzo[d][1,3]diazepin-2(3H)-one hydrochloride

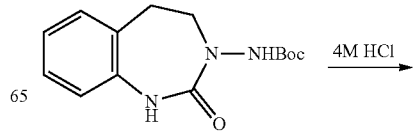

-continued

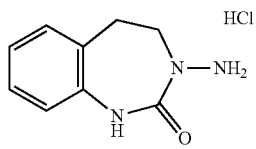

To a stirred solution of tert-butyl (2-oxo-4,5-dihydro-1H-benzo[d][1,3]diazepin-3(2H)-yl)carbamate (230 mg, 0.791 mmol) in dichloromethane (2 mL) at 0° C. was added HCl (4M in 1,4-dioxane) (0.989 mL, 3.96 mmol). The reaction mixture was stirred for 5 hr and concentrated under reduced pressure. The resultant solid was triturated with n-pentane (30 mL) and dried under vacuum at 50° C. to afford 3-amino-4,5-dihydro-1H-benzo[d][1,3]diazepin-2(3H)-one hydrochloride (160 mg, 94% yield) as a pale brown solid. $^1$H NMR (400 MHz, DMSO-$d_6$): δ 2.97-3.10 (m, 2H), 3.69-3.83 (m, 2H), 6.96-7.09 (m, 2H), 7.14-7.30 (m, 2H), 9.69 (s, 1H), 9.72-10.79 (br s, 3H). MS (m/z) 178.1 [M+H]$^+$ Example 1

5-Benzyl-N-(6,8-dimethyl-2-oxo-2,3,4,5-tetrahydro-1H-thieno[3,4-b]azepin-3-yl)-4H-1,2,4-triazole-3-carboxamide

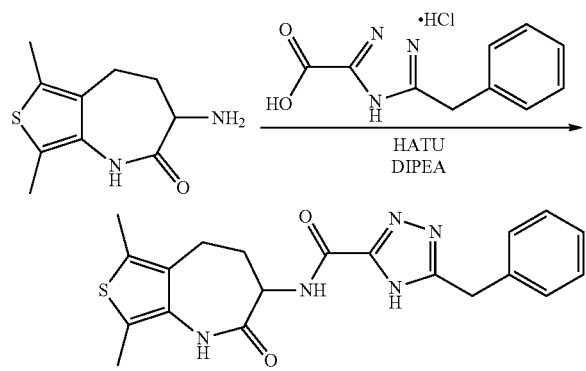

To a solution of 3-amino-6,8-dimethyl-4,5-dihydro-1H-thieno[3,4-b]azepin-2(3H)-one (65 mg, 0.309 mmol), 5-benzyl-4H-1,2,4-triazole-3-carboxylic acid, hydrochloride (69.1 mg, 0.340 mmol), and HATU (129 mg, 0.340 mmol) in DMSO (1.2 ml) was added Hunig's base (0.135 ml, 0.773 mmol) at rt. The reaction mixture was stirred for 1 hr at rt and diluted with MeOH (1.2 mL). After filtration through Acrodisc CR 25 mm syringe filter with 0.2 uM PTFE membrane, the solution was purified by preparatory HPLC (Waters Sunfire, 30×150 mm, eluent: a gradient of 20-60% acetonitrile (containing 0.1% TFA):water (containing 0.1% TFA)) to afford 5-benzyl-N-(6,8-dimethyl-2-oxo-2,3,4,5-tetrahydro-1H-thieno[3,4-b]azepin-3-yl)-4H-1,2,4-triazole-3-carboxamide (62.7 mg, 0.159 mmol, 51.3% yield). $^1$H NMR (DMSO-$d_6$) δ: 14.45 (br s., 1H), 9.78 (s, 1H), 8.22 (br s., 1H), 7.21-7.37 (m, 5H), 4.34 (dt, J=11.3, 7.5 Hz, 1H), 4.11 (s, 2H), 2.72-2.87 (m, 1H), 2.31 (s, 3H), 2.25-2.39 (m, 2H), 2.23 (s, 3H), 1.94-2.07 (m, 1H). MS (m/z) 396.2 [M+H]$^+$.

Example 2

5-Benzyl-N-(5-oxo-5,6,7,8-tetrahydro-4H-thieno[3,2-b]azepin-6-yl)-4H-1,2,4-triazole-3-carboxamide

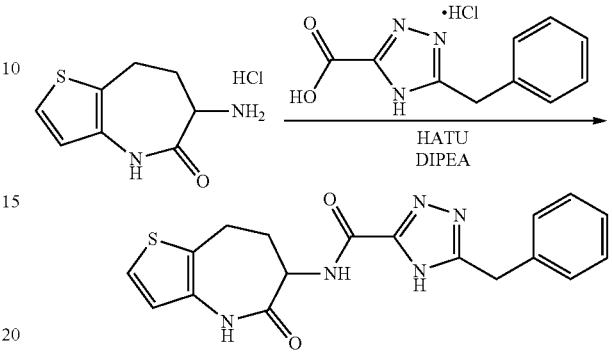

To a solution of 6-amino-7,8-dihydro-4H-thieno[3,2-b]azepin-5(6H)-one hydrochloride (0.080 g, 0.366 mmol), 5-benzyl-4H-1,2,4-triazole-3-carboxylic acid, hydrochloride (0.105 g, 0.439 mmol), and HATU (0.153 g, 0.402 mmol) in DMSO (1.46 ml) was added Hunig's base (0.319 ml, 1.829 mmol). The reaction mixture was stirred for 1 hr at rt and was diluted with MeOH (1 mL). After filtration through Acrodisc CR 25 mm syringe filter with 0.2 uM PTFE membrane, the solution was purified by preparatory HPLC (Waters Sunfire, 30×150 mm, eluent: a gradient of 20-60% acetonitrile (containing 0.1% TFA):water (containing 0.1% TFA)) to afford 5-benzyl-N-(5-oxo-5,6,7,8-tetrahydro-4H-thieno[3,2-b]azepin-6-yl)-4H-1,2,4-triazole-3-carboxamide (69.4 mg, 0.185 mmol, 50.6% yield). $^1$H NMR (DMSO-$d_6$) δ: 14.33 (br s., 1-), 10.12 (s, 1H), 8.32 (d, J=4.5 Hz, 1H), 7.16-7.44 (m, 6H), 6.75 (d, J=5.5 Hz, 1H), 4.45 (ddd, J=10.7, 6.8, 3.9 Hz, 1H), 3.99-4.22 (m, 2H), 2.88-3.08 (m, 2H), 2.10-2.44 (m, 2H). MS (m/z) 368.1 [M+H]$^+$.

Example 3

5-Benzyl-N-(2-methyl-5-oxo-5,6,7,8-tetrahydro-4H-thieno[3,2-b]azepin-6-yl)-4H-1,2,4-triazole-3-carboxamide

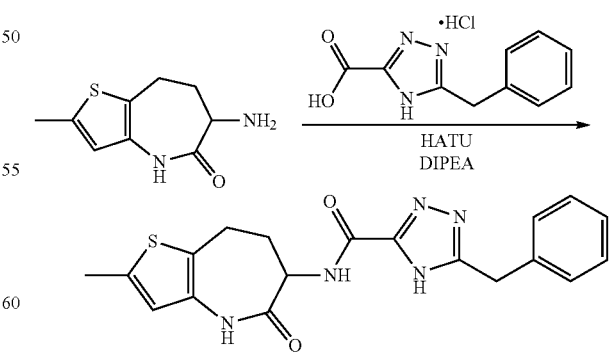

To a solution of 6-amino-2-methyl-7,8-dihydro-4H-thieno[3,2-b]azepin-5(6H)-one (63 mg, 0.321 mmol), 5-benzyl-4H-1,2,4-triazole-3-carboxylic acid, hydrochloride (71.7 mg, 0.353 mmol), and HATU (134 mg, 0.353 mmol)

in DMSO (1.2 ml) was added Hunig's base (0.140 ml, 0.802 mmol) at rt. The reaction mixture was stirred for 1 hr at rt and diluted with MeOH (1.2 mL). After filtration through Acrodisc CR 25 mm syringe filter with 0.2 uM PTFE membrane, the solution was purified by preparatory HPLC (Waters Sunfire, 30×150 mm, a gradient of 20-60% acetonitrile (containing 0.1% TFA):water (containing 0.1% TFA)) to afford 5-benzyl-V-(2-methyl-5-oxo-5,6,7,8-tetrahydro-4H-thieno[3,2-b]azepin-6-yl)-4H-1,2,4-triazole-3-carboxamide (5.1 mg, 0.013 mmol, 4.08% yield). $^1$H NMR (DMSO-$d_6$) δ: 10.04 (s, 1H), 8.33 (d, J=6.8 Hz, 1H), 7.18-7.36 (m, 6H), 6.45 (d, J=1.0 Hz, 1H), 4.43 (ddd, J=10.6, 6.9, 3.5 Hz, 1H), 4.07 (s, 2H), 2.86-2.95 (m, 2H), 2.34 (s, 3H), 2.28-2.34 (m, 1H), 2.04-2.16 (m, 1H). MS (m/z) 382.1[M+H]$^+$.

Example 4

5-Benzyl-N-(1-methyl-5-oxo-1,4,5,6,7,8-hexahydropyrrolo[3,2-b]azepin-6-yl)-4H-1,2,4-triazole-3-carboxamide

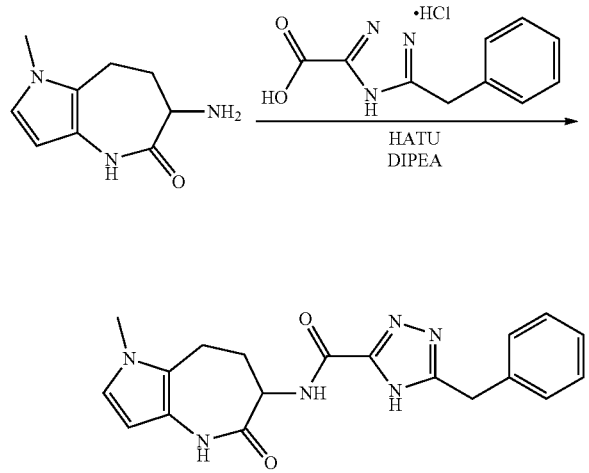

To a solution of 6-amino-1-methyl-4,6,7,8-tetrahydropyrrolo[3,2-b]azepin-5(1H)-one (63 mg, 0.352 mmol), 5-benzyl-4H-1,2,4-triazole-3-carboxylic acid, hydrochloride (79 mg, 0.387 mmol), and HATU (14' mg, 0.387 mmol) in DMSO (1.2 ml) was added Hunig's base (0.153 ml, 0.879 mmol) at rt. The reaction mixture was stirred for 1 hr at rt and diluted with MeOH (1.2 mL). After filtration through Acrodisc CR 25 mm syringe filter with 0.2 uM PTFE membrane, the solution was purified by prepartory HPLC (Waters Sunfire, 30×150 mm, eluent: a gradient of 20-60% acetonitrile (containing 0.1% TFA):water (containing 0.1% TFA)) to afford 5-benzyl-N-(1-methyl-5-oxo-1,4,5,6,7,8-hexahydropyrrolo[3,2-b]azepin-6-yl)-4H-1,2,4-triazole-3-carboxamide (54.1 mg, 42%). $^1$H NMR (DMSO-$d_6$) δ: 14.50 (br s., 1H), 9.71 (s, 1H), 8.43 (d, J=6.0 Hz, 1H), 7.17-7.41 (m, 5H), 6.61 (d, J=2.8 Hz, 1H), 5.69 (d, J=3.0 Hz, 1H), 4.29 (dd, J=9.4, 6.1 Hz, 1H), 4.12 (s, 2H), 3.47 (s, 3H), 2.77-2.96 (m, 2H), 2.19-2.32 (m, 1H), 1.87-2.03 (m, 1H). MS (m/z) 365.2 [M+H]$^+$.

Example 5

5-Benzyl-N-(1,3-dimethyl-5-oxo-1,4,5,6,7,8-hexahydropyrrolo[3,2-b]azepin-6-yl)-4H-1,2,4-triazole-3-carboxamide

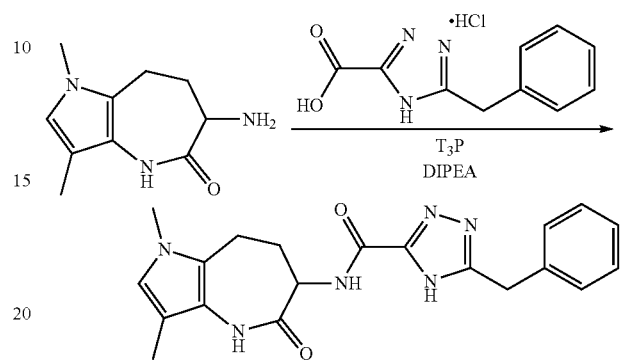

To a mixture of 6-amino-1,3-dimethyl-4,6,7,8-tetrahydropyrrolo[3,2-b]azepin-5(1H)-one (19 mg, 0.093 mmol) and 5-benzyl-4H-1,2,4-triazole-3-carboxylic acid, hydrochloride (24.74 mg, 0.098 mmol) in DCM (1 mL) were added DIPEA (0.049 mL, 0.280 mmol) and T$_3$P (50% by wt. in ethyl acetate) (0.084 mL, 0.140 mmol). The reaction mixture was stirred at rt for 30 minutes and concentrated under reduced pressure. The resulting residue was diluted with ethyl acetate and washed with 10% aq. citric acid, saturated aq. NaHCO$_3$, water, and brine. The organic layer was concentrated under reduced pressure and dried to give 5-benzyl-N-(1,3-dimethyl-5-oxo-1,4,5,6,7,8-hexahydropyrrolo[3,2-b]azepin-6-yl)-4H-1,2,4-triazole-3-carboxamide (17.5 mg, 47.5%) as a tan solid. $^1$H NMR (DMSO-$d_6$) δ: 14.83 (br s., 0.3H), 14.38 (br s., 0.7H), 9.33 (s, 1H), 8.53 (br s, 0.3H), 8.35 (br s., 0.7H), 7.21-7.39 (m, 5H), 6.41 (s, 1H), 4.32 (m, 1H), 4.03-4.19 (br m., 2H), 3.41 (s, 3H), 2.74-2.92 (m, 2H), 2.26 (br s., 1H), 1.97 (br s., 1H), 1.90 (s, 3H). MS (m/z) 379.3 [M+H]$^+$.

Example 6

5-Benzyl-N-(2-oxo-1,2,3,4,5,6-hexahydroazepino[3,2-b]indol-3-yl)-4H-1,2,4-triazole-3-carboxamide

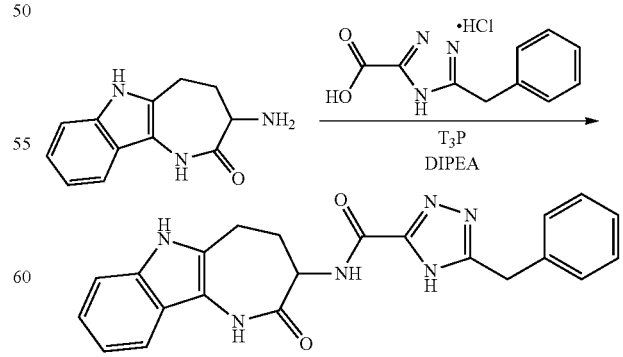

To a mixture of 3-amino-3,4,5,6-tetrahydroazepino[3,2-b]indol-2(1H)-one (50 mg, 0.228 mmol) and 5-benzyl-4H-1,2,4-triazole-3-carboxylic acid, hydrochloride (60.3 mg, 0.239 mmol) in DCM (2 mL) were added DIPEA (0.119 mL, 0.683 mmol) and T$_3$P (50% by wt. in ethyl acetate) (0.204 mL, 0.341 mmol). The reaction mixture was stirred at rt for 30 min and concentrated under reduced pressure. The resulting residue was diluted with ethyl acetate and 10% citric acid. The mixture was stirred vigorously to afford a solid. The resulting solid was collected. The filtrate was washed with saturated aq. NaHCO$_3$, water, and brine. The filtrate contained 5-benzyl-N-(2-oxo-1,2,3,4,5,6-hexahydroazepino [3,2-b]indol-3-yl)-4H-1,2,4-triazole-3-carboxamide and an impurity. The isolated solid was dried to give 53 mg (58%) of 5-benzyl-/V-(2-oxo-1,2,3,4,5,6-hexahydroazepino[3,2-b] indol-3-yl)-4H-1,2,4-triazole-3-carboxamide as a white solid. $^1$H NMR (DMSO-d$_6$) δ: 10.89 (s, 1H), 10.08 (s, 1H), 8.46 (br s., 1H), 7.67 (d, J=7.9 Hz, 1H), 7.23-7.37 (m, 6H), 7.06 (m, 1H), 6.96 (m, 1H), 4.46 (dd, J=9.1, 6.6 Hz, 1H), 4.14 (br s., 2H), 3.05-3.16 (m, 2H), 2.29-2.37 (m, 1H), 2.08-2.20 (m, 1H). MS (m/z) 401.3 [M+H]$^+$.

Example 7

(S)-5-Benzyl-N-(3,4-dimethyl-5-oxo-5,6,7,8-tetra-hydro-4H-isothiazolo[4,5-b][1,4]diazepin-6-yl)-4H-1,2,4-triazole-3-carboxamide

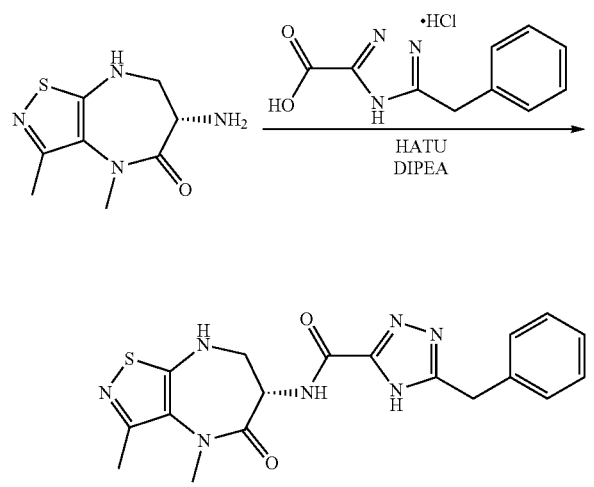

To a solution of (S)-6-amino-3,4-dimethyl-7,8-dihydro-4H-isothiazolo[4,5-b][1,4]diazepin-5(6H)-one, 2 hydrochloride (75 mg, 0.263 mmol), 5-benzyl-4H-1,2,4-triazole-3-(carboxylic acid, hydrochloride (58.8 mg, 0.289 mmol), and HATU (110 mg, 0.289 mmol) in DMSO (1.1 ml) was added Hunig's base (0.207 ml, 1.183 mmol) at rt. The reaction mixture was stirred for 1 hr at rt and diluted with MeOH (1.2 mL). After filtration through Acrodisc CR 25 mm syringe filter with 0.2 uM PTFE membrane, the solution was purified by preparatory HPLC (Waters Sunfire, 30×150 mm, eluent: a gradient of 20-60% acetonitrile (containing 0.1% TFA):water (containing 0.1% TFA)) to provide (S)-5-benzyl-N-(3,4-dimethyl-5-oxo-5,6,7,8-tetrahydro-4H-iso-thiazolo[4,5-b][1,4]diazepin-6-yl)-4H-1,2,4-triazole-3-carboxamide (29.4 mg, 0.072 mmol, 27.6% yield). $^1$H NMR (DMSO-d$_6$) δ: 14.47 (br s., 1H), 8.26 (d, J=4.8 Hz, 1H), 7.21-7.41 (m, 6H), 4.77 (ddd, J=10.2, 6.8, 3.3 Hz, 1H), 4.13 (s, 2H), 3.65-3.75 (m, 1H), 3.37-3.48 (m, 1H), 3.19 (s, 3H), 2.28 (s, 3H). MS (m/z) 398.1 [M+H]$^+$.

Example 8

(R)-5-Benzyl-N-(4-oxo-2,3,4,5-tetrahydropyrrolo[2,1-b][1,3,4]thiadiazepin-3-yl)-4H-1,2,4-triazole-3-carboxamide

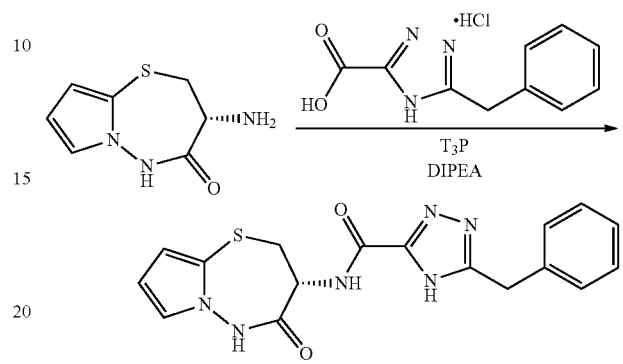

To a mixture of (R)-3-amino-2,3-dihydropyrrolo[2,1-b] [1,3,4]thiadiazepin-4(5H)-one (18.58 mg, 0.101 mmol) and 5-benzyl-4H-1,2,4-triazole-3-carboxylic acid, hydrochloride (25.5 mg, 0.106 mmol) in DCM (1 mL) was added DIPEA (0.053 mL, 0.304 mmol) and T$_3$P (50% by wt. in ethyl acetate) (0.091 mL, 0.152 mmol). The reaction mixture was stirred at room temperature for 30 min and concentrated under reduced pressure. The residue was dissolved in ethyl acetate and washed with 1M aq. HCl, saturated NaHCO$_3$, water, and brine. The organic layer was concentrated under reduced pressure and dried to give 27 mg (68%) of (R)-5-benzyl-N-(4-oxo-2,3,4,5-tetrahydropyrrolo[2,1-b][1,3,4] thiadiazepin-3-yl)-4H-1,2,4-triazole-3-carboxamide. $^1$H NMR (DMSO-d$_6$) δ: 8.55 (br s, 1H), 7.19-7.35 (m, 7H), 6.42 (dd, J=3.8, 1.8 Hz, 1H), 6.20 (dd, J=3.9, 3.2 Hz, 1H), 4.24 (dt, J=11.4, 7.6 Hz, 1H), 4.12 (s, 2H), 3.42 (dd, J=11.5, 7.2 Hz, 1H), 3.14 (t, J=11.5 Hz, 1H). MS (m/z) 369.3 [M+H]$^+$.

Example 9

(R)-5-Benzyl-N-(5-methyl-4-oxo-2,3,4,5-tetrahydro-pyrrolo[2,1-b][1,3,4]thiadiazepin-3-yl)-4H-1,2,4-triazole-3-carboxamide

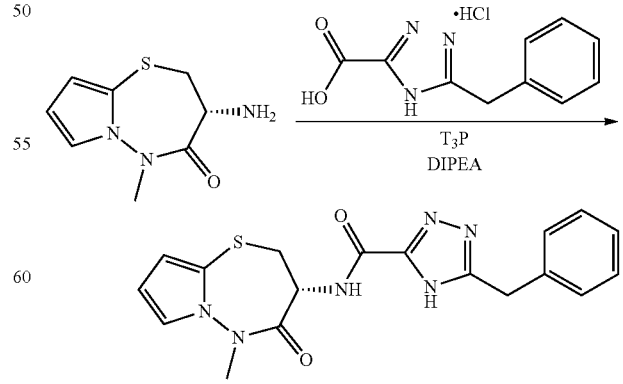

To a mixture of (R)-3-amino-5-methyl-2,3-dihydropyr-rolo[2,1-b][1,3,4]thiadiazepin-4(5H)-one (20 mg, 0.101 mmol) and 5-benzyl-4H-1,2,4-triazole-3-carboxylic acid, hydrochloride (25.5 mg, 0.106 mmol) in DCM (1 mL) was added DIPEA (0.053 mL, 0.304 mmol) and T$_3$P (50% by wt. in ethyl acetate) (0.091 mL, 0.152 mmol). The reaction mixture was stirred at room temperature for 30 min and concentrated under reduced pressure. The resulting residue was dissolved in ethyl acetate and washed with 1M aq. HCl, saturated NaHCO$_3$, water, and brine. The organics were concentrated and dried to give 25 mg (61%) of (R)-5-benzyl-N-(5-methyl-4-oxo-2,3,4,5-tetrahydropyrrolo[2,1-b][1,3,4]thiadiazepin-3-yl)-4H-1,2,4-triazole-3-carboxamide. $^1$H NMR (DMSO-d$_6$) δ: 8.62 (br s., 1H), 7.47 (dd, J=3.3, 1.8 Hz, 1H), 7.21-7.36 (m, 6H), 6.43 (dd, J=4.1, 1.8 Hz, 1H), 6.27-6.31 (m, 1H), 4.23 (dt, J=11.5, 7.6 Hz, 1H), 4.12 (s, 2H), 3.39 (m, 1H) (partially obscured by water and —CH$_3$ peaks), 3.35 (s, 3H) (partially obscured by water peak), 3.16 (m, 1H). MS (m/z) 383.3 [M+H]$^+$.

Example 10

5-benzyl-N-(2-oxo-2,3,4,5,7,8,9,10-octahydro-1H-benzofuro[3,2-b]azepin-3-yl)-4H-1,2,4-triazole-3-carboxamide

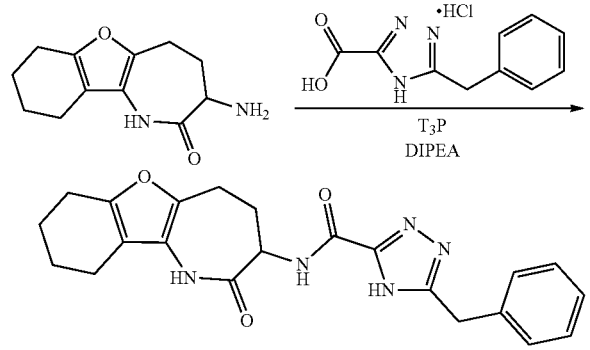

To a solution of 3-amino-4,5,7,8,9,10-hexahydro-1H-benzofuro[3,2-b]azepin-2(3H)-one (30 mg, 0.136 mmol) and 5-benzyl-4H-1,2,4-triazole-3-carboxylic acid, hydrochloride (34.3 mg, 0.143 mmol) in DCM (1 mL) were added DIPEA (0.071 mL, 0.409 mmol) and T$_3$P (50% by wt. in ethyl acetate) (0.122 mL, 0.204 mmol). The reaction was stirred at room temperature for 30 minutes and concentrated under reduced pressure. The resulting residue was dissolved in ethyl acetate and washed with 1M HCl, saturated NaHCO$_3$, water, and brine. The organic layer was concentrated under reduced pressure to afford a solid, which was triturated in diethyl ether (1.5 mL). The solid was filtered, rinsed with diethyl ether, and dried to give 24 mg (40%) of 5-benzyl-N-(2-oxo-2,3,4,5,7,8,9,10-octahydro-1H-benzofuro[3,2-b]azepin-3-yl)-4H-1,2,4-triazole-3-carboxamide as a light orange solid. $^1$H NMR (DMSO-d$_6$) δ: 14.36 (br s., 1H), 9.66 (s, 1H), 8.47 (br s., 1H), 7.21-7.37 (m, 5H), 4.36 (dd, J=9.8, 6.5 Hz, 1H), 4.14 (br s., 2H), 2.80-2.98 (m, 2H), 2.47 (m, 3H), 2.11-2.25 (m, 2H), 1.90-2.03 (m, 1H), 1.73 (br d., J=4.1 Hz, 2H), 1.63 (br d., J=4.1 Hz, 2H). MS (m/z) 406.3 [M+H]$^+$.

Pharmaceutical Compositions

EXAMPLE A-An ointment is prepared by combining 20% (w/w) of the compound of any of Examples 1-10, and 80% (w/w) of petrolatum. The mixture is passed through a roller mill until a uniform consistency is obtained.

EXAMPLE B-Aerosol Spray: A solution is prepared from the following components: [Ingredient (Amount (w/w))]: Compound of any one of Examples 1-10 (1.00), propylene glycol (5.00), golysorbate 80 (1.00), ethanol (78.00), purified water (15.00). The solution is placed in a conventional aerosol container, a valve mechanism is attached, and the container is charged with nitrogen to 100 psig.

EXAMPLE C-Tablets are prepared using conventional methods and are formulated as follows: [Ingredient (Amount per tablet)]: Compound of any one of Examples 1-10 (5 mg), microcrystalline cellulose (100 mg), lactose (100 mg), sodium starch glycollate (30 mg), magnesium stearate (2 mg).

EXAMPLE D-Capsules are prepared using conventional methods and are formulated as follows: [Ingredient (Amount per tablet)]: Compound of any one of Examples 1-10 (15 mg), dried starch (178 mg), magnesium stearate (2 mg).

Biological In Vitro Assay

A fluorescent polarization based binding assay was developed to quantitate interaction of novel test compounds at the ATP binding pocket of RIP 1, by competition with a fluorescently labeled ATP competitive ligand. GST-RipK1(1-375) was purified from a Baculovirus expression system and was used at a final assay concentration of 10 nM. A fluorescent labeled ligand (14-(2-{[3-({2-{[4-(cyanomethyl)phenyl]amino}-6-[(5-20 cyclopropyl-1H-pyrazol-3-yl)amino]-4-pyrimidinyl}amino)propyl]amino}-2-oxoethyl)16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate (prepared as described in WO2014125444, the disclosure of which is incorporated by reference herein) was used at a final assay concentration of 5 nM. Both the enzyme and ligand were prepared in solutions in 50 mM HEPES pH7.5, 10 mM 25 NaCl, 50 mM MgCl$_2$, 0.5 mM DTT, and 0.02% CHAPS. Test compounds were prepared in neat DMSO and 100 nL was dispensed to individual wells of a multiwell plate. Next, 5 ul GST-RipK1 (1-375) was added to the test compounds at twice the final assay concentration, and incubated at room temperature for 10 minutes. Following the incubation, 5 ul of the fluorescent labeled ligand solution, was added to each reaction, at twice the final assay concentration, and incubated at room temperature for at least 15 minutes. Finally, samples were read on an instrument capable of measuring fluorescent polarization. Test compound inhibition was expressed as percent (%) inhibition of internal assay controls. For concentration response experiments, normalized data were fit and pIC$_{50}$s determined using conventional techniques. The pIC$_{50}$s are averaged to determine a mean value, for a minimum of 2 experiments.

As determined using the above method, the compound of Example 1 exhibited a pIC$_{50}$ of 7.0, the compound of Example 2 exhibited a pIC$_{50}$ of 6.6, the compound of Example 3 exhibited a pIC$_{50}$ of 7.1, the compound of Example 4 exhibited a pIC$_{50}$ of 6.1, the compound of Example 5 exhibited a pIC$_{50}$ of 6.2, the compound of Example 6 exhibited a pIC$_{50}$ of 7.4, the compound of Example 7 exhibited a pIC$_{50}$ of 7.7, the compound of Example 8 exhibited a pIC$_{50}$ of 7.6, the compound of Example 9 exhibited a pIC$_{50}$ of 8.0, and the compound of Example 10 exhibited a pIC$_{50}$ of 6.1.

GST-RipK1 Preparation: His.GST.TEV.RIPK1 1-375

The RIPK 1 gene [receptor (TNFRSF)-interacting serine-threonine kinase 1] was cloned from human adrenal gland cDNA. Primers were designed from the reference sequence NM_003804.3 with an added CACC Kozak directional tag for cloning into pENTR/TEV/D-TOPO. Gateway® LR cloning was used to site-specifically recombine RIPK1 downstream to an N-terminal HisGST contained within the destination vector pDEST8-His.GST according to the protocol described by Invitrogen. A stop codon was inserted after amino acid 375 using Quikchange Stratagene mutagenesis kit according to manufacturer's protocol and resulted in pDEST8.His.GST.TEV.human RIPK1 1-375.

His.GST.TEV.human RIPK1 1-375 baculovirus was generated using the bac to bac system (Invitrogen) according to manufacturer's specifications. Transfection of *Spodoptera frugiperda* (Sf9) insect cells was performed using Fugene 6 (Roche), according to the manufacturer's protocol. His.GST.TEV.human RIPK1 1-375 baculovirus infected insect cells (BIICs) were prepared during the baculovirus generation according to David Wasilko and S Edward Lee, TIPS: Titerless Infected Cells Preservation and Scale up, BioProcessing Journal Fall 2006 p 29-32. 20L Sf9 cells were grown in serum free Hyclone, SFX media (HyClone Laboratories, 925 West 1800 South Logan, Utah 84321) at 27° C. in wave bags seeded at a density of 8×10^6cell/ml with a rock rate of 25 rpm, airflow of 0.18 to 0.22. in wave reactor (WAVE Bioreactor, System 20/50EH). Cells were grown ON at 27° C.

His.GST.TEV.human RIPK1 1-375 baculovirus infected insect cells (BIICs) were used to infect Sf9s at a cell density of 1.7 to 2.4×10^6. 2 ml of BIIC (1×10^7cells/mL) were added to 20L cells. Rock rate is increased to 25rom at infection. Harvest 72 hrs post infection using the Viafuge. Weigh pellets, seal wave bags and freeze at −80° C.

A 50 g cell pellet was re-suspended in 250 ml lysis buffer (50 mM Tris pH 7.5, 250 mM NaCl, 1 mM DTT and Complete Protease Inhibitor tablets (1/50 ml, from Roche Diagnostics). The cells were lysed by sonication on ice, 3×30" at power level 4 using the large probe on a Branson Sonicator. The suspension was then clarified by centrifugation at 15,000 g for 30 minutes, at 4° C. The lysate was decanted from the insoluble pellet and batch bound to 10 ml of Glutathione Agarose (Pierce) for 2 h at 4° C. with gentle end over end rotation. The beads were then packed into a column and washed to baseline with lysis buffer (no protease inhibitors) and then eluted with 20 mM reduced glutathione in 50 mM Tris, pH8.

Fractions identified by SDS-PAGE as containing protein of interest were pooled (10 ml total volume), concentrated to about 5 ml and loaded onto a 300 ml SDX200 SEC column (GE Healthcare) which had been equilibrated in 50 mM Tris, pH7.5, 150 mM NaCl, 1 mM DTT and 10% Glycerol. The Rip1 protein eluted as a dimer off the SEC column.

The protein concentration was determined by Bradford assay using BSA as a standard. The yield was 12.5 mg at 0.63 mg/ml. The purity was >95% as determined by scanning a Coomassie stained SDS-PAGE gel.

LCMS analysis showed that the major species had lost the N-terminal methionine, was acetylated and had one phosphorylated site. The protein was aliquoted and frozen at −80° C. for use as needed.

Biological In Vitro Cell Assay

The efficacy of RIP1 inhibitors can be tested in mice in vitro using a human monocytic leukemia U937 cells in a necroptosis assay (He, S. et al. 2009. Cell 137(6): 1100-1111). Cells were maintained in RPMI supplemented with 10% fetal bovine serum 100 U/ml penicillin, 100 ug/ml streptomycin. For the assay, cells were suspended at 5e5 cells/ml in phenol red free RPMI supplemented with 1% fetal bovine serum, 100 U/ml penicillin, 100 ug/ml streptomycin. Thirty-five (35) ul of the cell suspension was aliquotted into a white, half area assay plate. Five (5) ul each of QVD (final concentration 50 uM) or compound was added to the cells and incubated at 37° C. for 30 min to 1 h. Following the incubation, 5 ul TNFα (final concentration 100 ng/ml) was added to the cells and the samples were incubated overnight. The next day, cellular levels of ATP was determined using the Cell Titer-Glo Luminescent Cell Viability kit (available from Promega Corporation, Madison, Wis., USA). Viability was measured by quantitating cellular levels of ATP using the Cell Titer-Glo kit. All data are shown as means±standard deviation of the mean.

As determined using the above method, the compound of Example 1 exhibited a $pIC_{50}$ of 6.4, the compound of Example 2 exhibited a $pIC_{50}$ of 6.1, the compound of Example 3 exhibited a $pIC_{50}$ of 6.2, the compound of Example 4 exhibited a $pIC_{50}$ of 5.9, the compound of Example 5 exhibited a $pIC_{50}$ of <5.0, the compound of Example 6 exhibited a $pIC_{50}$ of 6.6, the compound of Example 7 exhibited a $pIC_{50}$ of 7.8, the compound of Example 8 exhibited a $pIC_{50}$ of 7.1, and the compound of Example 9 exhibited a $pIC_{50}$ of 8.3.

What is claimed is:

1. A compound according to Formula (I):

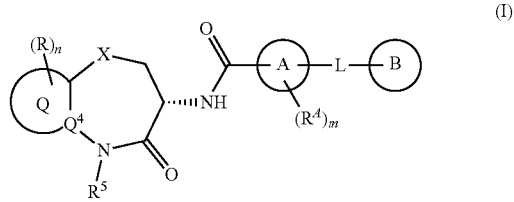

wherein:

X is $CH_2$;

Q is a 5-membered heteroaryl ring moiety, wherein the heteroaryl ring moiety contains one heteroatom, which heteroatom is a sulfur ring heteroatom;

$Q^4$ is C;

each R is independently selected from $(C_1-C_6)$alkyl;

n is 0, 1, 2 or 3;

$R^5$ is H;

A is a 5-6 membered heteroaryl ring comprising one to three heteroatoms, wherein the heteroatom is nitrogen, and wherein the carbonyl moiety and L are substituted 1,3 on ring A;

L is $CH_2$; and

B is phenyl;

or a pharmaceutically acceptable salt, or a tautomer, thereof.

2. The compound according to claim 1 which is

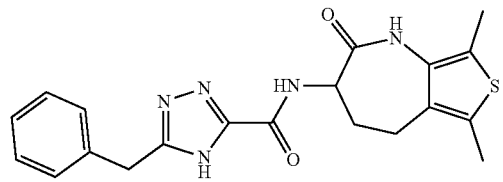 [SMILES: Cc1sc(C)c2c1CCC(NC(=O)c1nnc(Cc3ccccc3)[nH]1)C(=O)N2]

or a pharmaceutically acceptable salt, or a tautomer, thereof.

3. The compound or pharmaceutically acceptable salt thereof, according to claim 1, wherein the compound is selected from the group consisting of:
- 5-benzyl-N-(6,8-dimethyl-2-oxo-2,3,4,5-tetrahydro-1H-thieno[3,4-b]azepin-3-yl)-4H-1,2, 4-triazole-3-carboxamide;
- 5-benzyl-N-(5-oxo-5,6,7,8-tetrahydro-4H-thieno[3,2-b]azepin-6-yl)-4H-1,2, 4-triazole-3-carboxamide; and
- 5-benzyl-N-(2-methyl-5-oxo-5,6,7,8-tetrahydro-4H-thieno[3,2-b]azepin-6-yl)-4H-1,2, 4-triazole- 3-carboxamide;

or a tautomer thereof.

\* \* \* \* \*